US008987462B2

(12) United States Patent
Kim et al.

(10) Patent No.: US 8,987,462 B2

(45) Date of Patent: Mar. 24, 2015

(54) COMPOUND AND ORGANIC LIGHT-EMITTING DEVICE COMPRISING THE SAME

(71) Applicants: Samsung Display Co., Ltd., Yongin, Gyeonggi-do (KR); Pusan National University Industry—University Cooperation Foundation, Busan (KR)

(72) Inventors: Soung-Wook Kim, Yongin (KR); Myeong-Suk Kim, Yongin (KR); Jae-Hong Kim, Yongin (KR); Jin-Soo Hwang, Yongin (KR); Hong-Suk Suh, Busan (KR)

(73) Assignees: Samsung Display Co., Ltd., Giheung-Gu, Yongin, Gyeonggi-Do (KR); Pusan National University Industry—University Cooperation Foundation, Geumjeong, Busan (KR)

( * ) Notice: Subject to any disclaimer, the term of this patent is extended or adjusted under 35 U.S.C. 154(b) by 0 days.

(21) Appl. No.: 14/036,574

(22) Filed: Sep. 25, 2013

(65) Prior Publication Data

US 2014/0306197 A1 Oct. 16, 2014

(30) Foreign Application Priority Data

Apr. 10, 2013 (KR) ........................ 10-2013-0039510

(51) Int. Cl.

| | |
|---|---|
| ***C07D 487/04*** | (2006.01) |
| ***C07D 401/14*** | (2006.01) |
| ***H01L 51/00*** | (2006.01) |
| ***H01L 51/50*** | (2006.01) |

(52) U.S. Cl.

CPC .......... *H01L 51/006* (2013.01); *H01L 51/0061* (2013.01); *H01L 51/5056* (2013.01); *H01L 51/5072* (2013.01); *H01L 51/5088* (2013.01); *H01L 51/5092* (2013.01)

USPC ........................................ 546/276.7; 548/421

(58) Field of Classification Search

None

See application file for complete search history.

(56) References Cited

U.S. PATENT DOCUMENTS

| | | | | |
|---|---|---|---|---|
| 2008/0242871 | A1 | 10/2008 | Kawakami et al. | |
| 2011/0037062 | A1 | 2/2011 | Fukumatsu et al. | |
| 2012/0018717 | A1 | 1/2012 | Kim et al. | |
| 2012/0080670 | A1 | 4/2012 | Park et al. | |
| 2013/0200350 | A1 * | 8/2013 | Sawada et al. .................. | 257/40 |

FOREIGN PATENT DOCUMENTS

| | | | |
|---|---|---|---|
| KR | 10-2008-0096733 | A | 11/2008 |
| KR | 10-2010-0121378 | A | 11/2010 |
| KR | 10-2011-0007124 | A | 1/2011 |
| KR | 10-2011-0021487 | A | 3/2011 |
| KR | 10-2012-0006000 | A | 1/2012 |
| KR | 10-2012-0089223 | A | 8/2012 |
| WO | 2011/025282 | A2 | 3/2011 |

* cited by examiner

*Primary Examiner* — Michael Barker

(74) *Attorney, Agent, or Firm* — Robert E. Bushnell, Esq.

(57) ABSTRACT

Provided are a compound of Formula 1 and an organic light-emitting device including the compound of Formula 1:

<Formula 1>

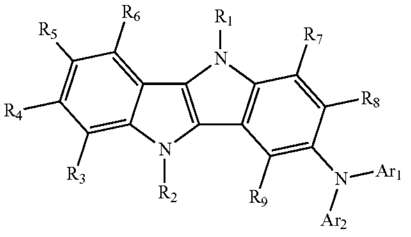

The compounds of Formula 1 are particularly useful as fluorescent dopants in the emission layer of the organic light-emitting device.

20 Claims, 1 Drawing Sheet

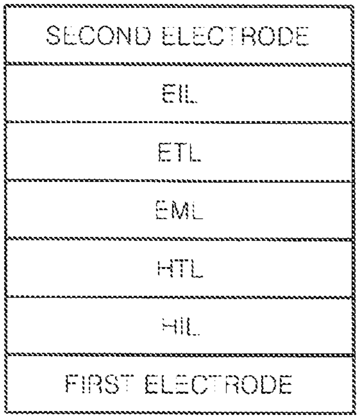
SECOND ELECTRODE
EIL
ETL
EML
HTL
HIL
FIRST ELECTRODE

COMPOUND AND ORGANIC LIGHT-EMITTING DEVICE COMPRISING THE SAME

CLAIM OF PRIORITY

This application makes reference to, incorporates the same herein, and claims all benefits accruing under 35 U.S.C. §119 from an application for COMPOUND AND ORGANIC LIGHT-EMITTING DEVICE COMPRISING THE SAME, earlier filed in the Korean Intellectual Property Office on Apr. 10, 2013, and there duly assigned Serial No. 10-2013-0039510.

BACKGROUND OF THE INVENTION

1. Field of the Inventive Concept

The present inventive concept relates to compounds of Formula 1 and an organic light-emitting device (OLED) comprising a compound of Formula 1.

2. Description of the Related Art

Organic light-emitting diodes (organic light-emitting devices), which are self-emitting diodes, have advantages, such as wide viewing angles, excellent contrast, quick responses, high brightness, excellent driving voltage characteristics, and providing multicolored images.

A typical organic light-emitting device may have a structure including a substrate, and an anode, a hole transport layer, an emission layer, an electron transport layer, and a cathode, which are sequentially stacked on the substrate. In this regard, the hole transport layer, the emission layer, and the electron transport layer may be organic thin films formed of organic compounds.

An operating principle of an organic light-emitting device having the above-described structure may be as follows:

When a voltage is applied between the anode and the cathode, holes injected from the anode move to the emission layer via the hole transport layer, and electrons injected from the cathode move to the emission layer via the electron transport layer. Charge carriers such as holes and electrons recombine in an emission region to generate excitons. When the excitons drop from an excited state to a ground state, light is emitted.

Materials known for the organic light-emitting device include emission materials, such as chelate complexes, for example, a tris(8-quinolinolato)aluminum complex, coumarin derivatives, tetraphenyl butadiene derivatives, bis-styryl arylene derivatives, and oxadiazole derivatives, and it has been reported that emission from a visible range from blue to red may be obtained from the emission materials. Accordingly, materialization of a color display device is anticipated. Also, phenylanthracene derivatives have been reported as blue emission materials. However, improvements of color purity, efficiency, and lifespan are still needed.

SUMMARY OF THE INVENTION

Provided are materials for organic light-emitting devices having high color purity, high efficiency, and a long lifespan.

According to an embodiment of the present inventive concept, there is provided a compound represented by Formula 1:

<Formula 1>

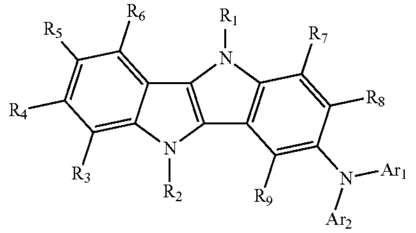

In Formula 1, $R_1$ to $R_9$ are each independently one of a hydrogen atom, a deuterium atom, a substituted or unsubstituted C5-C60 alkyl group, a substituted or unsubstituted C5-C60 aryl group, a substituted or unsubstituted C3-C60 heteroaryl group, an amine group substituted with a C5-C60 aryl group or a C3-C60 heteroaryl group, a substituted or unsubstituted C6-C60 condensed polycyclic group, a halogen group, a cyano group, a nitro group, a hydroxy group and a carboxy group; and $Ar_1$ and $Ar_2$ are each independently one of a substituted or unsubstituted C5-C60 aryl group, a substituted or unsubstituted C3-C60 heteroaryl group and a substituted or unsubstituted C6-C60 condensed polycyclic group.

According to another aspect of the present inventive concept, there is provided an organic light-emitting device including a first electrode; a second electrode; and an organic layer interposed between the first electrode and the second electrode, the organic layer including a compound of Formula 1.

According to another embodiment of the present inventive concept, there is provided a flat display device including an organic light-emitting device, a first electrode of the organic light-emitting device being electrically connected to one of a source electrode and a drain electrode of a thin film transistor.

BRIEF DESCRIPTION OF THE DRAWINGS

A more complete appreciation of the invention and many of the attendant advantages thereof will be readily apparent as the same becomes better understood by reference to the following detailed description when considered in conjunction with the accompanying drawings in which like reference symbols indicate the same or similar components, wherein:

FIG. 1 schematically illustrates a structure of an organic light-emitting device according to an embodiment of the present invention.

DETAILED DESCRIPTION OF THE INVENTION

A compound according to an embodiment of the present inventive concept may be represented by Formula 1:

<Formula 1>

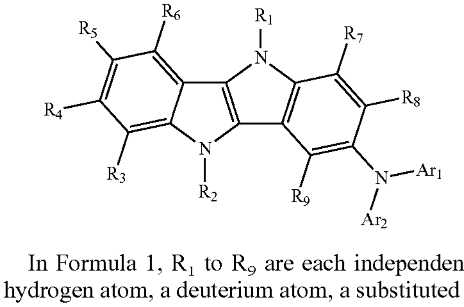

In Formula 1, $R_1$ to $R_9$ are each independently one of a hydrogen atom, a deuterium atom, a substituted or unsubstituted C5-C60 alkyl group, a substituted or unsubstituted C5-C60 aryl group, a substituted or unsubstituted C3-C60 heteroaryl group, or an amine group substituted with a C5-C60 aryl group or a C3-C60 heteroaryl group, a substituted or unsubstituted C6-C60 condensed polycyclic group, a halogen group, a cyano group, a nitro group, a hydroxy group and a carboxy group, and $Ar_1$ and $Ar_2$ are each independently one of a substituted or unsubstituted C5-C60 aryl group, a substituted or unsubstituted C3-C60 heteroaryl group and a substituted or unsubstituted C6-C60 condensed polycyclic group.

According to an embodiment of the present inventive concept, $R_3$, $R_4$, $R_6$, $R_7$, $R_8$, and $R_9$ of Formula 1 are each independently one of a hydrogen atom and a deuterium atom.

According to another embodiment of the present inventive concept, $R_1$ and $R_2$ of Formula 1 are each independently represented as one of Formulae 2a to 2c.

2a

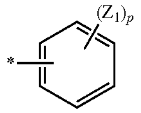

2b

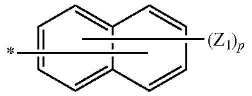

2c

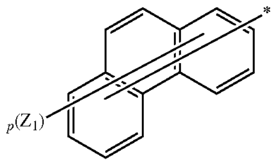

In Formulae 2a to 2c, $Z_1$ is one of a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen group, a cyano group, a nitro group, a hydroxy group and a carboxy group, p is an integer of 1 to 9; and * represents a bond.

According to another embodiment of the present inventive concept, $R_5$ of Formula 1 may be a substituted or unsubstituted C1-C20 alkyl group or represented by one of Formulae 3a to 3d.

3a

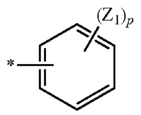

3b

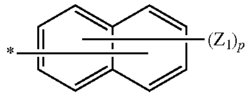

3c $*—N(R_{50})(R_{51})$

-continued

3d

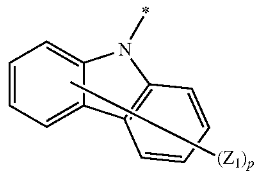

In Formula 3a to 3d, $Z_1$, $R_{50}$, and $R_{51}$ are each independently one of a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, an amino group substituted with a C5-C20 aryl group or a C3-C20 heteroaryl group, a halogen group, a cyano group, a nitro group, a hydroxy group and a carboxy group; p is an integer of 1 to 7; and * represents a bond.

According to another embodiment of the present inventive concept, $Ar_1$ and $Ar_2$ of Formula 1 may be each independently represented by Formulae 4a and 4b.

4a

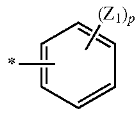

4b

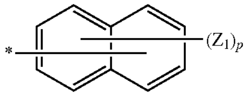

In Formulae 4a and 4b, $Z_1$ is one of a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, an amino group substituted with a C5-C20 aryl group or a C3-C20 heteroaryl group, a halogen group, a cyano group, a nitro group, a hydroxy group and a carboxy group; p is an integer of 1 to 7; and * represents a bond.

An organic light-emitting device according to another embodiment of the present inventive concept includes a first electrode; a second electrode; and an organic layer interposed between the first electrode and the second electrode, the organic layer including a compound represented by Formula 1.

According to an embodiment of the present inventive concept, the organic layer may further include a compound represented by Formula 2.

<Formula 2>

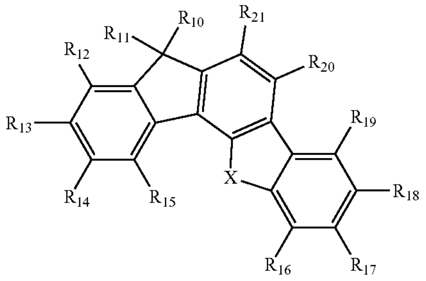

In Formula 2, $R_{10}$ to $R_{21}$ are each independently one of a hydrogen atom, a deuterium atom, a substituted or unsubstituted C5-C60 alkyl group, a substituted or unsubstituted C5-C60 aryl group, a substituted or unsubstituted C3-C60 heteroaryl group, an amine group substituted with a C5-C60 aryl group or a C3-C60 heteroaryl group, a substituted or unsubstituted C6-C60 condensed polycyclic group, a halogen group, a cyano group, a nitro group, a hydroxy group and a carboxy group, X is a connecting group represented by one of —$C(R_{100})(R_{101})$—, —$N(R_{102})$—, —S— and —O—, and $R_{100}$, $R_{101}$, and $R_{102}$ are each independently one of a substituted or unsubstituted C5-C30 aryl group, a substituted or unsubstituted C3-C30 heteroaryl group and a substituted or unsubstituted C6-C30 condensed polycyclic group.

A compound of Formula 1 may be a host and a compound of Formula 2 may be, for example, a dopant. In some embodiments, a compound of Formula 2 may be the host, and a compound of Formula 1 may be, for example, the dopant.

An organic light-emitting device according to an embodiment of the present inventive concept has high efficiency and a long lifespan and, thus, may be used in a full color display or a (laminated) white organic light-emitting device.

According to another embodiment of the present inventive concept, $R_{10}$ and $R_{11}$ of Formula 2 may be bonded to each other to form a 9,9'-spirobifluorene moiety [hence,

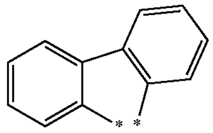 [SMILES: *c1ccccc1-c1ccccc1*]

] or (for example, compounds 55-63, 97-99, 103-105, or the like of Formula 2, represented below), or $R_{10}$ and $R_{11}$ may be each independently a substituted or unsubstituted C1-C20 alkyl group, and * represents a bond.

According to another embodiment of the present inventive concept, $R_{13}$ of Formula 2 may be one of Formulae 5a to 5c.

5a

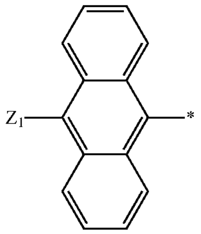

5b

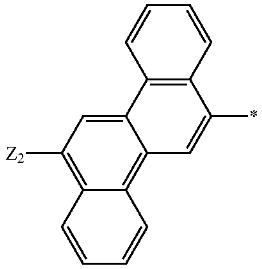

-continued

5c

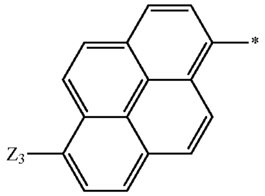

In Formulae 5a to 5c, $Z_1$, $Z_2$, and $Z_3$ may be each independently one of a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, an amino group substituted with a C5-C20 aryl group or a C3-C20 heteroaryl group, a halogen group, a cyano group, a nitro group, a hydroxy group and a carboxy group; and * represents a bond.

Hereinafter, representative substituents of the substituents used in the present specification are as follows. (Carbon numbers limiting the substituents are non-limiting and do not limit the characteristics of the substituents. Substituents that are not specifically described in the present specification are found in general definitions of the generic substituents and may be considered to be equivalents of those described herein.)

An unsubstituted C1-C60 alkyl group may be linear or branched, and non-limiting examples of the unsubstituted C1-C60 alkyl group include methyl, ethyl, propyl, isobutyl, sec-butyl, pentyl, isoamyl, hexyl, heptyl, octyl, nonanyl, dodecyl, and the like, and at least one hydrogen atom of the unsubstituted C1-C60 alkyl group may be substituted with one of a deuterium atom, a halogen atom, a hydroxy group, a nitro group, a cyano group, an amino group, an amidino group, hydrazine, hydrazone, a carboxyl group or a salt thereof, a sulfonic acid group or a salt thereof, a phosphoric acid or a salt thereof, a C1-C10 alkyl group, a C1-C10 alkoxy group, a C2-C10 alkenyl group, a C2-C10 alkynyl group, a C6-C16 aryl group and a C4-C16 heteroaryl group. Hereinafter, the substituents may be substituted with the above-described substituents of the unsubstituted C1-C60 alkyl group.

As used herein, an unsubstituted C2-C60 alkenyl group is a hydrocarbon chain having at least one of a carbon-carbon double bond in the center and a carbon-carbon double bond at a terminal of an unsubstituted alkyl group. Examples of the alkenyl group are an ethenyl group, a propenyl group, a butenyl group, and the like. At least one hydrogen atom in the unsubstituted C2-C60 alkenyl group may be substituted with the substituents described above in conjunction with the substituted C1-C60 alkyl group.

An unsubstituted C2-C60 alkynyl group is a C2-C60 alkyl group having at least one carbon-carbon triple bond in the center or at a terminal of the unsubstituted alkynyl group. Examples of the unsubstituted C2-C60 alkynyl group are acetylene, propylene, phenylacetylene, naphthylacetylene, isopropyl acetylene, t-butyl acetylene, diphenyl acetylene, and the like. At least one hydrogen atom in the alkynyl group may be substituted with those substituents described above in conjunction with the substituted C1-C60 alkyl group.

An unsubstituted C3-C60 cycloalkyl group is a C3-C60 cyclic alkyl group, and at least one hydrogen atom of the unsubstituted C3-C60 cycloalkyl group may be substituted with those substituents described above in conjunction with the substituted C1-C60 group.

An unsubstituted C1-C60 alkoxy group may be a group represented by —OA, wherein A is the unsubstituted C1-C60 alkyl group. Non-limiting examples of the unsubstituted C1-C60 alkoxy group are a methoxy group, an ethoxy group, a propoxy group, an isopropyloxy group, a butoxy group, and a pentoxy group. At least one hydrogen atom of the unsubstituted C1-C60 alkoxy group may be substituted with those substituents described above in conjunction with the substituted C1-C60 group.

A C7-C60 aralkyl group represents a substituent in which an alkyl group is connected to an aryl group, and examples of a substituted or unsubstituted aralkyl group include, a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthyl isopropyl group, a 2-α-naphthyl isopropyl group, a β-naphthylmethyl group, 1-a β-naphthylethyl group, a 2-β-naphthylethyl group, a 1-β-naphthyl isopropyl group, a 2-β-naphthyl isopropyl group, a 1-pyrrolyl methyl group, a 2-(1-pyrrolyl)ethyl group, a p-methyl benzyl group, an m-methyl benzyl group, an o-methyl benzyl group, a p-chloro benzyl group, an m-chloro benzyl group, an o-chloro benzyl group, a p-bromo benzyl group, an m-bromo benzyl group, an o-bromo benzyl group, a p-iodo benzyl group, an m-iodo benzyl group, an o-iodo benzyl group, a p-hydroxy benzyl group, an m-hydroxy benzyl group, an o-hydroxy benzyl group, a p-amino benzyl group, an m-amino benzyl group, an o-amino benzyl group, a p-nitro benzyl group, an m-nitro benzyl group, an o-nitro benzyl group, a p-cyano benzyl group, an m-cyano benzyl group, an o-cyano benzyl group, a 1-hydroxy-2-phenyl isopropyl group, a 1-chloro-2-phenyl isopropyl group, and the like.

A C1-C60 alkoxycarbonyl group is represented as —COOZ, and examples of Z include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxy isobutyl group, a 1,2-dihydroxy ethyl group, a 1,3-dihydroxy isopropyl group, a 2,3-dihydroxy-t-butyl group, a 1,2,3-trihydroxy propyl group, a chloromethyl group, a 1-chloroethyl group, a 2-chloroethyl group, a 2-chloroisobutyl group, a 1,2-dichloroethyl group, a 1,3-dichloro isopropyl group, a 2,3-dichloro-t-butyl group, a 1,2,3-trichloropropyl group, a bromomethyl group, a 1-bromoethyl group, 2-bromoethyl group, a 2-bromoisobutyl group, a 1,2-dibromoethyl group, a 1,3-dibromo isopropyl group, a 2,3-dibromo-t-butyl group, a 1,2,3-tribromo propyl group, an iodomethyl group, a 1-iodoethyl group, a 2-iodoethyl group, a 2-iodoisobutyl group, a 1,2-diiodoethyl group, a 1,3-diiodo isopropyl group, a 2,3-diiodo-t-butyl group, a 1,2,3-triiodo propyl group, an aminomethyl group, a 1-aminoethyl group, a 2-aminoethyl group, a 2-aminoisobutyl group, a 1,2-diamino ethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, and the like.

An unsubstituted C6-C60 aryl group is a carbocyclic aromatic system including at least one aromatic ring, and when the unsubstituted C6-C60 aryl group has at least two rings, they may be fused or may be connected via a single bond. The term "aryl" as used herein includes an aromatic system, such as phenyl, naphthyl, or anthracenyl. At least one hydrogen atom in the unsubstituted C6-C60 aryl group may be substituted with those substituents described above in conjunction with the unsubstituted C1-C60 alkyl group.

Examples of a substituted or unsubstituted C6-C60 aryl group include a phenyl group, a C1-C10 alkyl phenyl group (for example, an ethyl phenyl group), a halophenyl group (for example, an o-, m-, and p-fluorophenyl group and a dichlorophenyl group), a cyanophenyl group, a dicyanophenyl group, a trifluoromethoxy phenyl group, a biphenyl group, a halobiphenyl group, a cyanobiphenyl group, a C1-C10 alkylbiphenyl group, a C1-C10 alkoxybiphenyl group, an o-, m-, and p-tolyl group, an o-, m-, and p-cumenyl group, a mesityl group, a phenoxyphenyl group, an (α,α-dimethyl benzene) phenyl group, an (N,N'-dimethyl) amino phenyl group, an (N,N'-diphenyl) amino phenyl group, a pentalenyl group, an indenyl group, a naphthyl group, a halonaphthyl group (for example, a fluoronaphthyl group), a C1-C10 alkyl naphthyl group (for example, a methyl naphthyl group), a C1-C10 alkoxy naphthyl group (for example, a methoxy naphthyl group), a cyanonaphthyl group, an anthracenyl group, an azulenyl group, a heptalenyl group, an acenaphthylenyl group, a phenalenyl group, a fluorenyl group, an anthraquinolyl group, a methyl anthryl group, a phenanthryl group, a triphenylene group, a pyrenyl group, a chrysenyl group, an ethyl-chrysenyl group, a picenyl group, a phenylenyl group, a chlorophenylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl group, a pyranthrenyl group, an ovalenyl group, and the like.

The unsubstituted C3-C60 heteroaryl group includes one, two, or three heteroatoms selected from N, O, P, and S, and when the unsubstituted C3-C60 heteroaryl group has at least two rings, they may be fused or connected to each other via a single bond. Examples of the unsubstituted C3-C60 heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolyl group, an isoquinolyl group, a dibenzothiophene group, and the like. Also, at least one hydrogen atom of the unsubstituted C3-C60 heteroaryl group may be substituted with those substituents described in conjunction with the unsubstituted C1-C60 alkyl group.

An unsubstituted C6-C60 aryloxy group is represented by $—OA_1$ (where $A_1$ is the substituted or unsubstituted C6-C60 aryl group). Examples of the unsubstituted C6-C60 aryloxy group include a phenoxy group and the like. At least one hydrogen atom in the aryloxy group may be substituted with those substituents described in conjunction with the substituted C1-C60 alkyl group.

An unsubstituted C6-C60 arylthio group is represented by $—SA_1$ (where $A_1$ is the substituted or unsubstituted C6-C60 aryl group). Examples of the unsubstituted C6-C60 arylthio group include a benzenethio group, a naphthylthio group, and the like. At least one hydrogen atom in the unsubstituted C6-C60 arylthio group may be substituted with those substituents described in conjunction with the substituted C1-C60 alkyl group.

The expression "the unsubstituted C6-C60 condensed polycyclic group" as used herein refers to a substituent including two or more rings, at least one aromatic ring and at least one non-aromatic ring being fused, or a substituent having an unsaturated group but that is incapable of having a conjugated structure. The unsubstituted C6-C60 condensed polycyclic group is distinguished from the aryl group or the heteroaryl group in that the condensed polycyclic group does not have an overall aromaticity.

The expression "the condensed polycyclic group including N, O, or S" as used herein refers to a polycyclic ring system including two or more rings and incorporating N, O, or S, at least one aromatic ring and at least one non-aromatic ring of the polycyclic ring system being fused, or a polycyclic ring system having two or more rings and incorporating N, O, or S and having an unsaturated group that is incapable of participating in a conjugated structure. Thus, the condensed polycyclic group refers to a compound that does not have an overall aromaticity.

At least one hydrogen atom of the condensed polycyclic group or a condensed polycyclic group including N, O, or S may be substituted with those substituents described in conjunction with the substituted C1-C60 alkyl group.

Examples of compounds represented by Formula 1 are as follows, but they are not limited thereto:

1

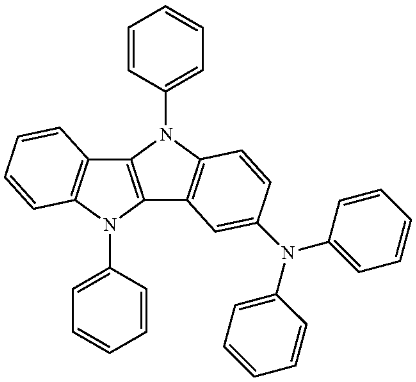

2

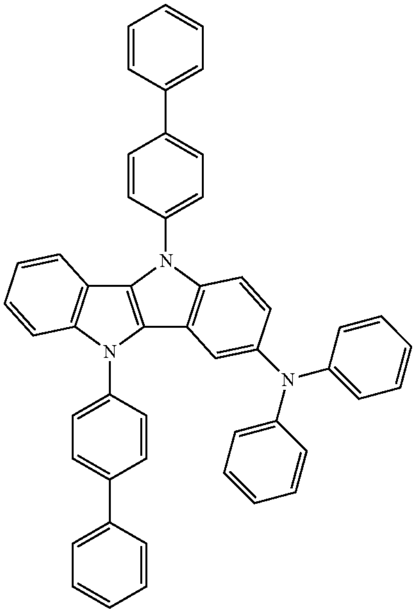

-continued

3

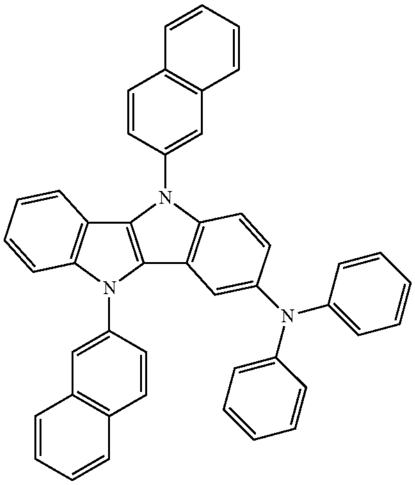

4

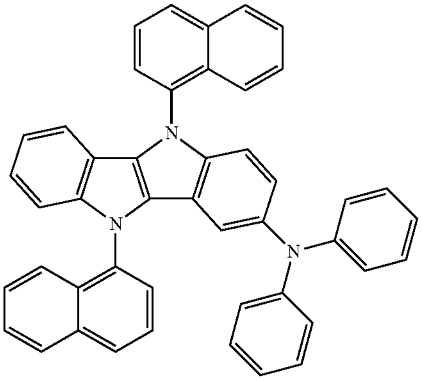

5

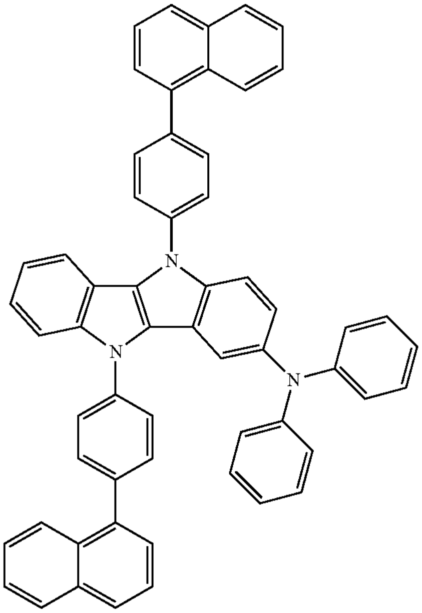

-continued
6
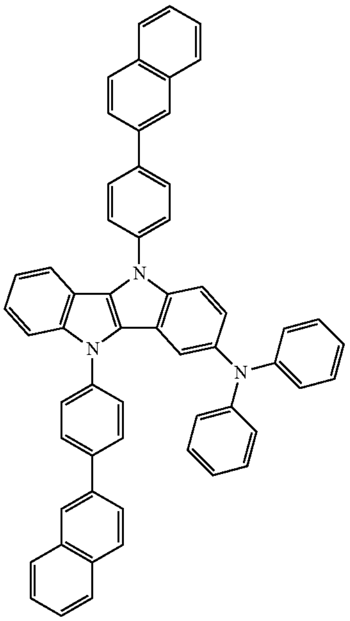
7
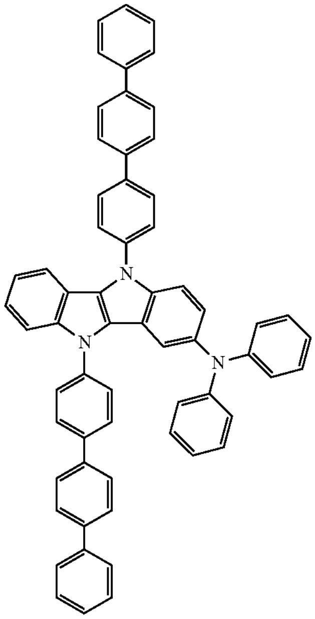
-continued
8
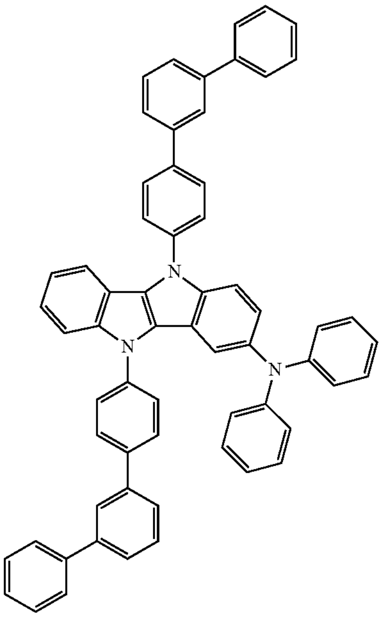
9
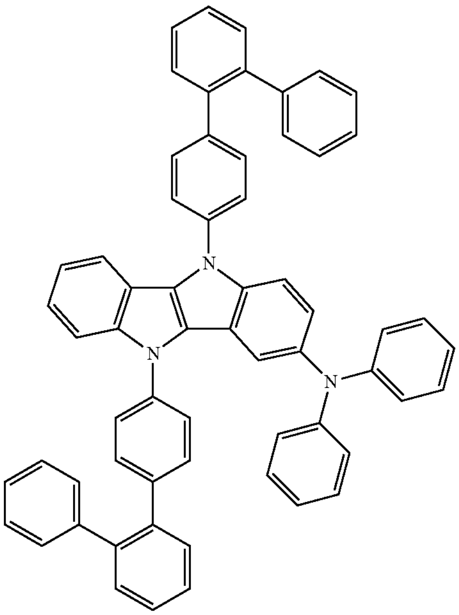

10
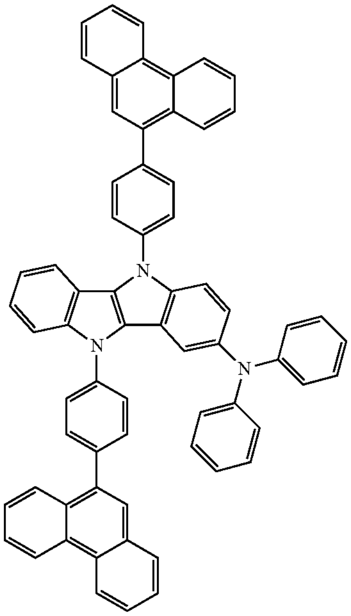
11
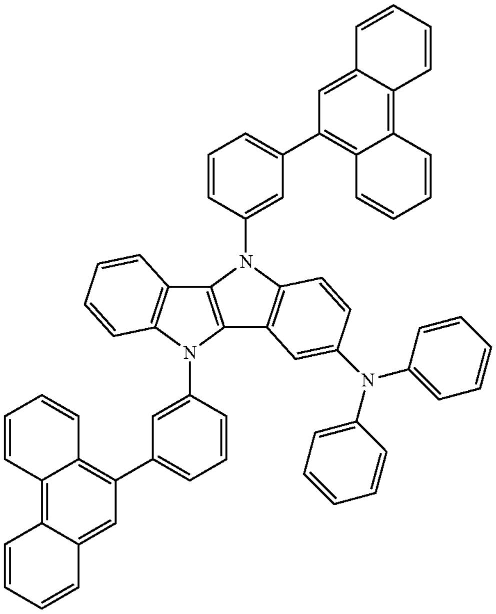
12
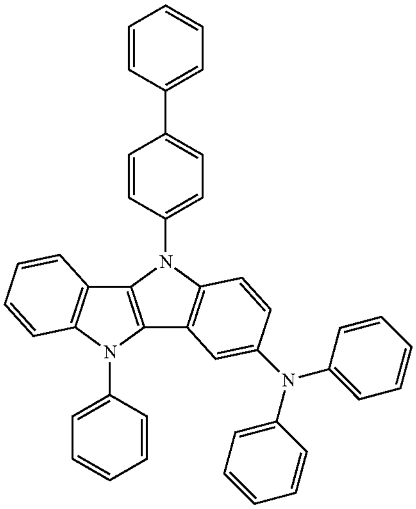
13
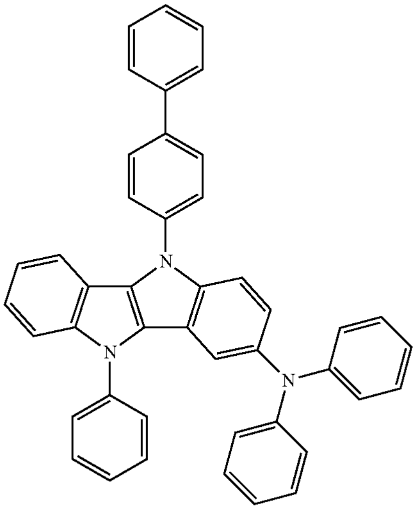
14
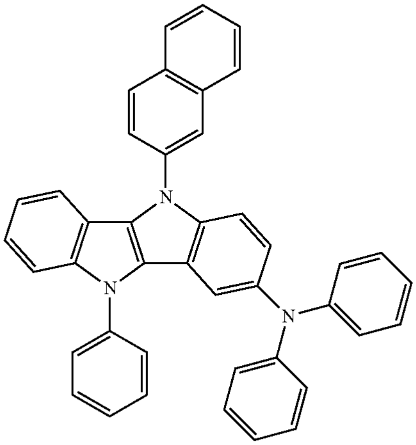

-continued
15
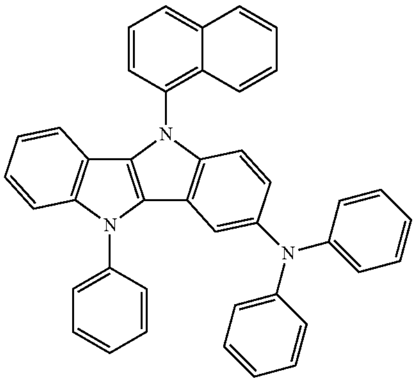
16
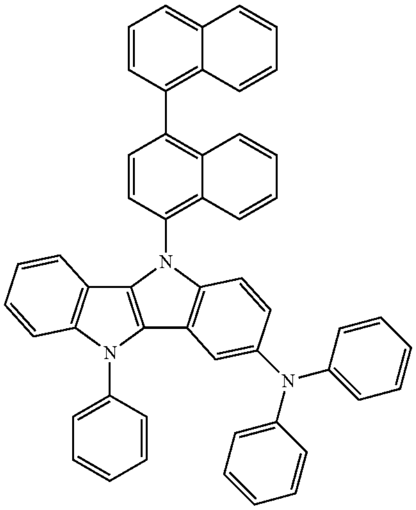
17
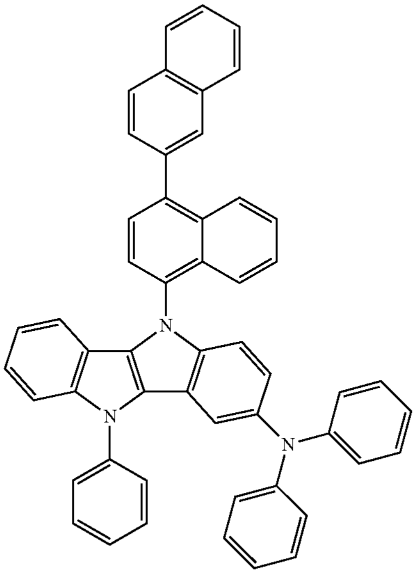
-continued
18
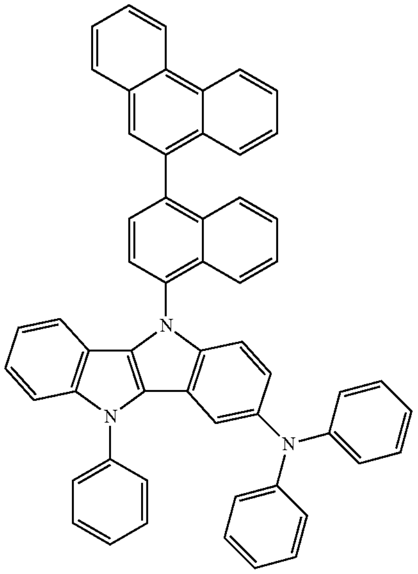
19
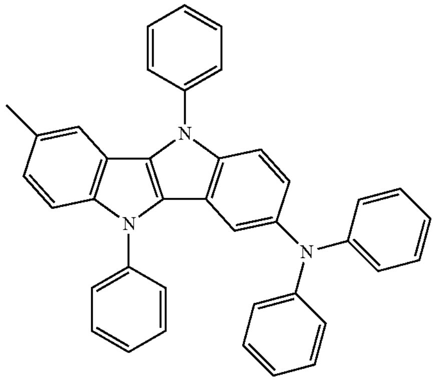
20
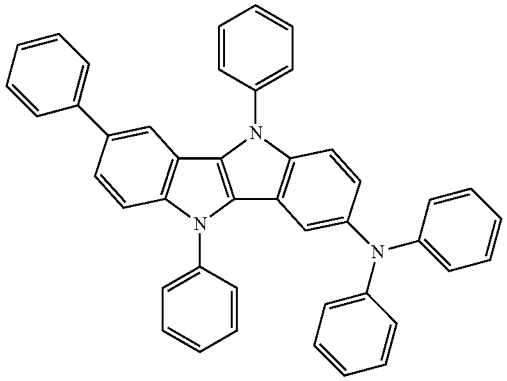

-continued
21
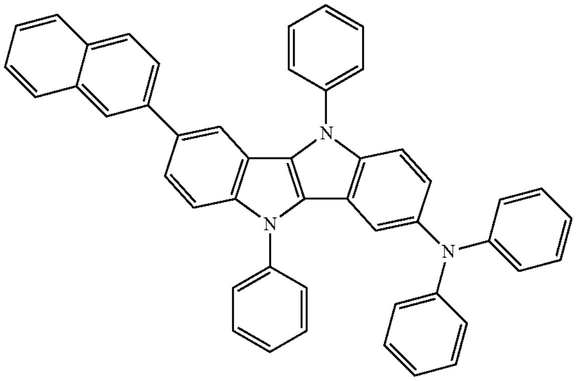
22
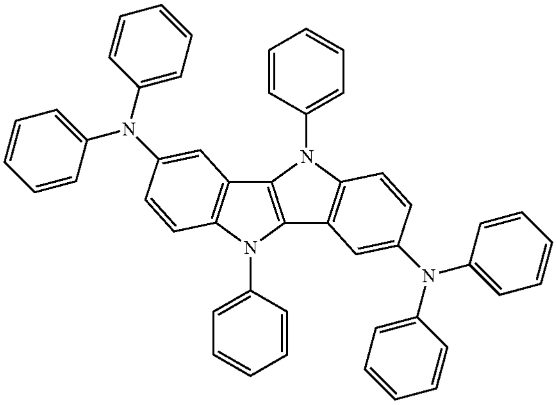
23
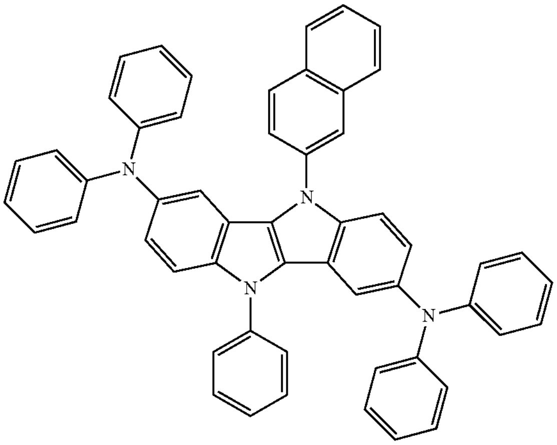
-continued
24
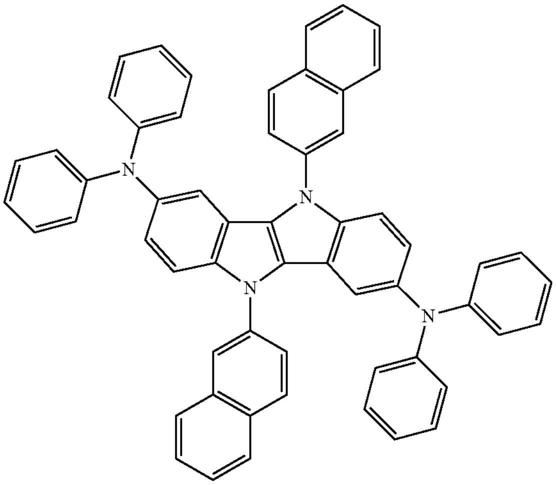
25
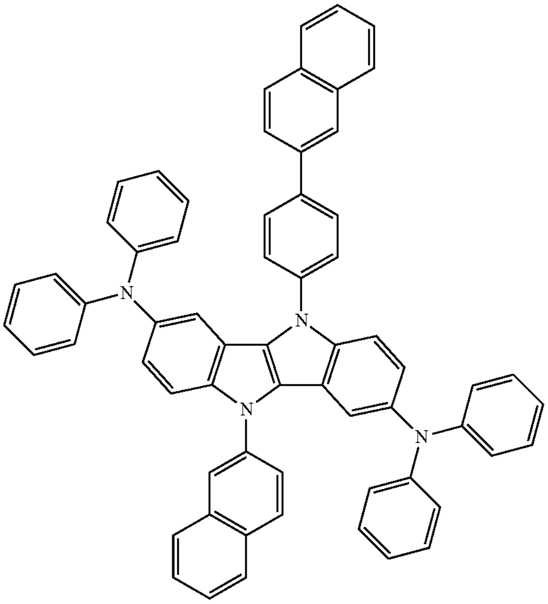

-continued
26
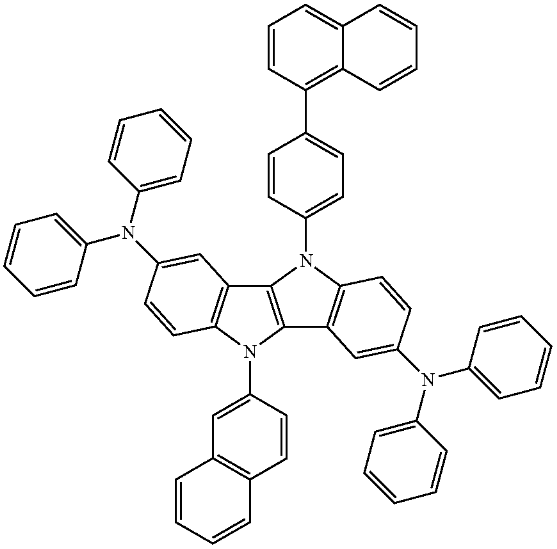
27
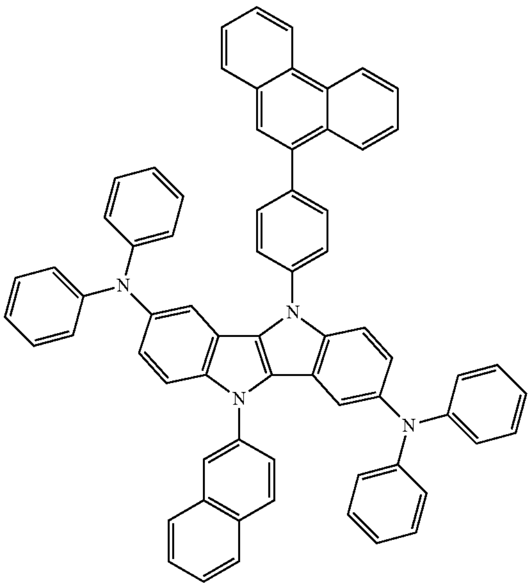
28
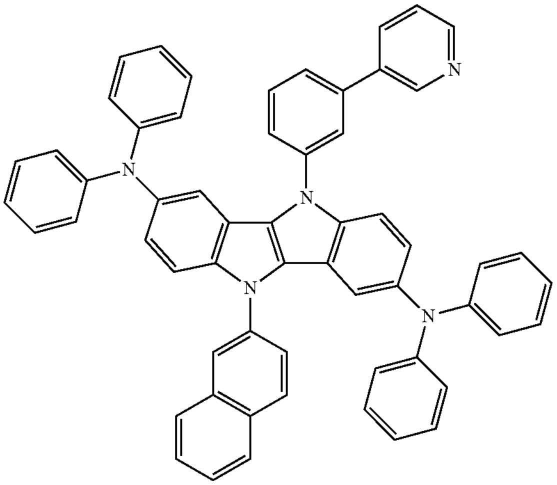
-continued
29
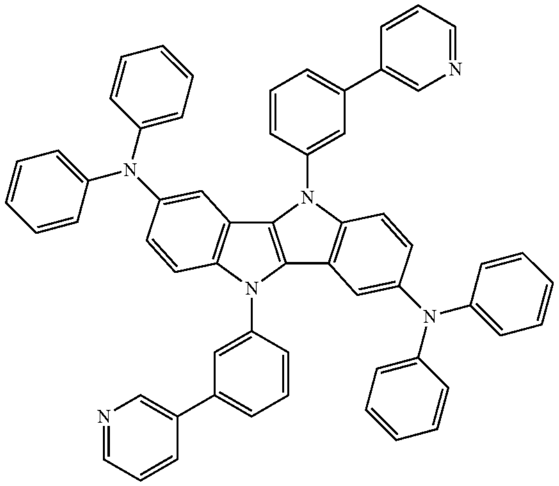
30
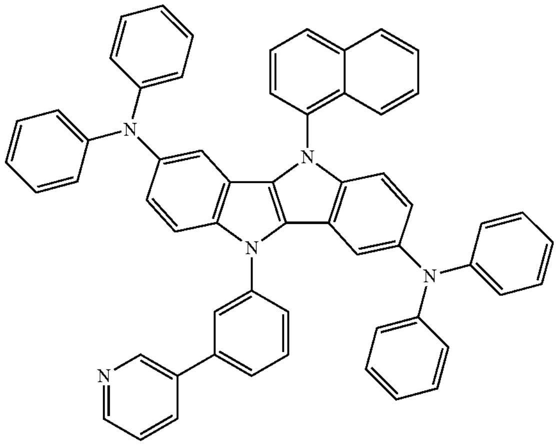
31
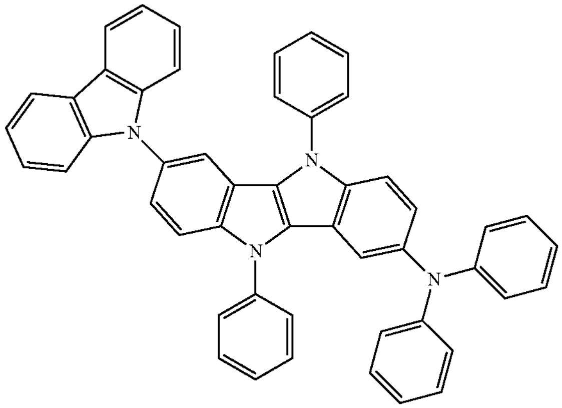

-continued
32
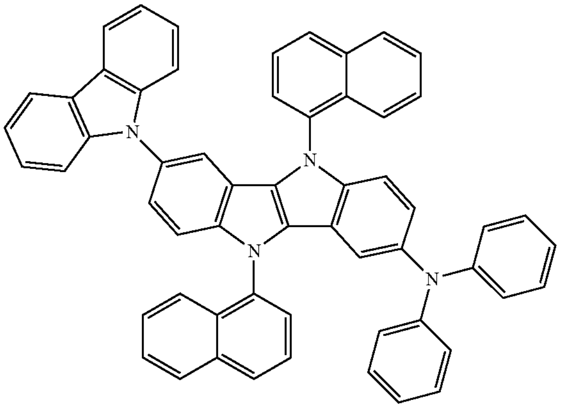
33
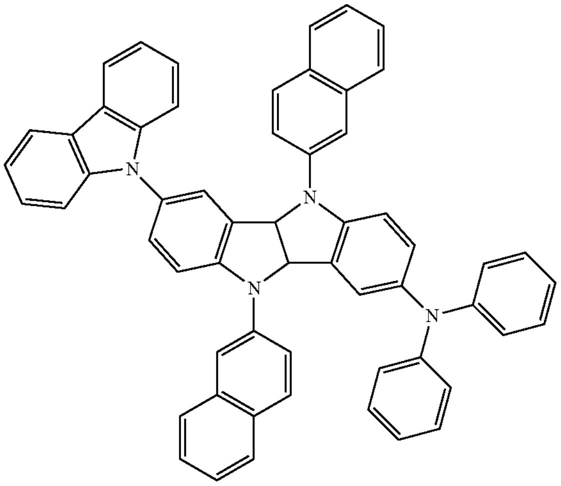
34
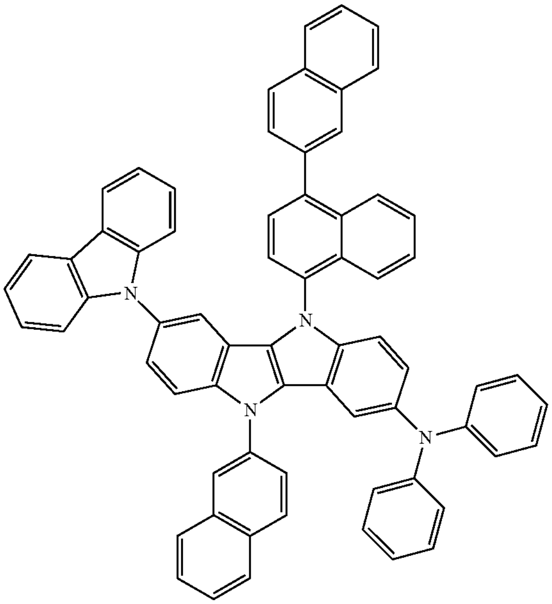
-continued
35
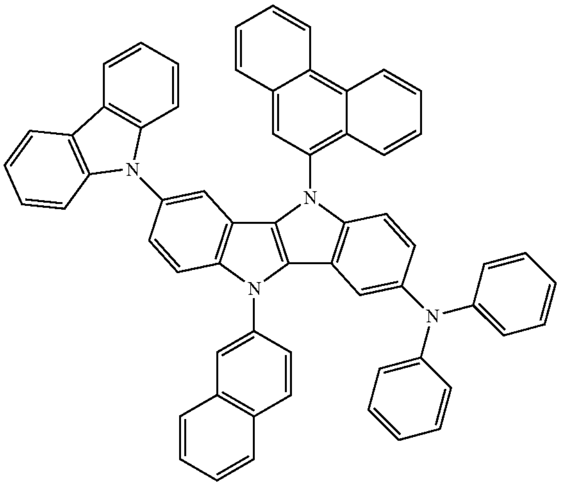
36
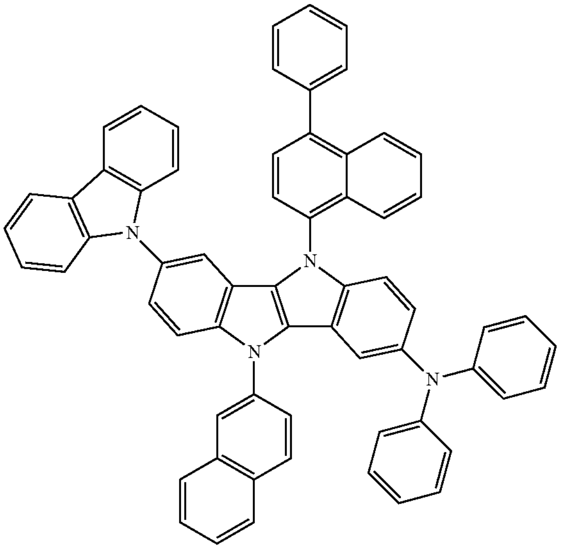
37
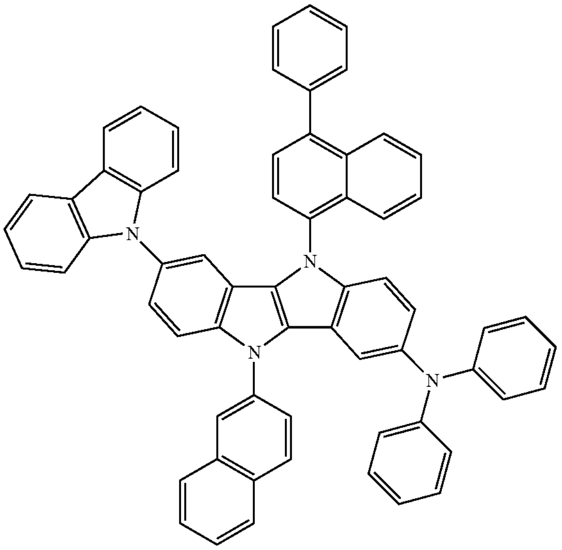

-continued
38
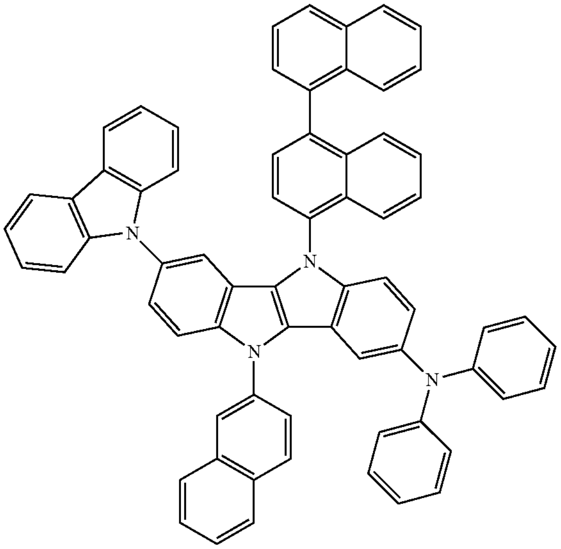
39
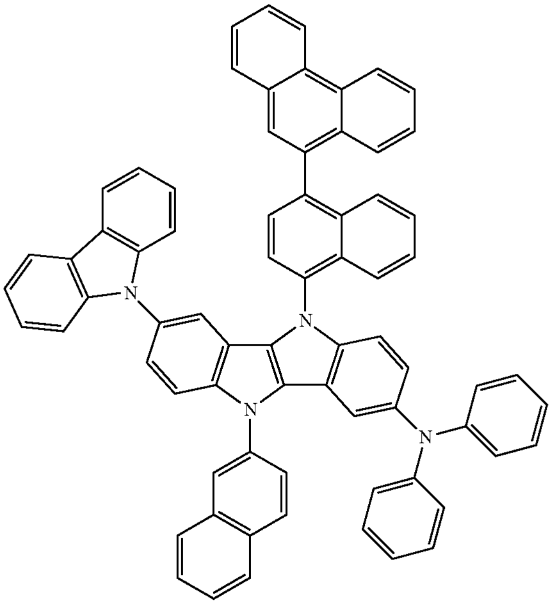
-continued
40
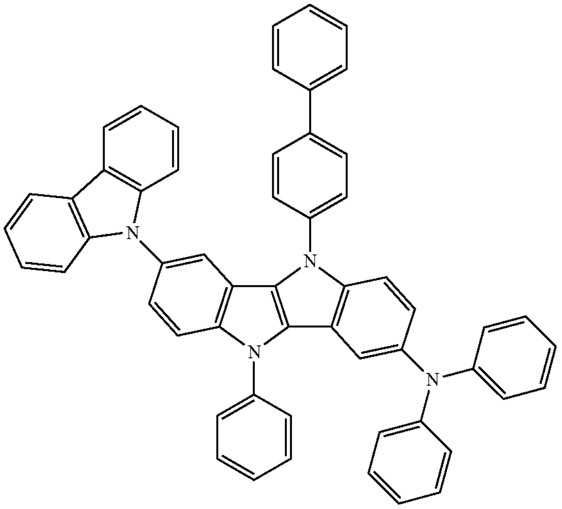
41
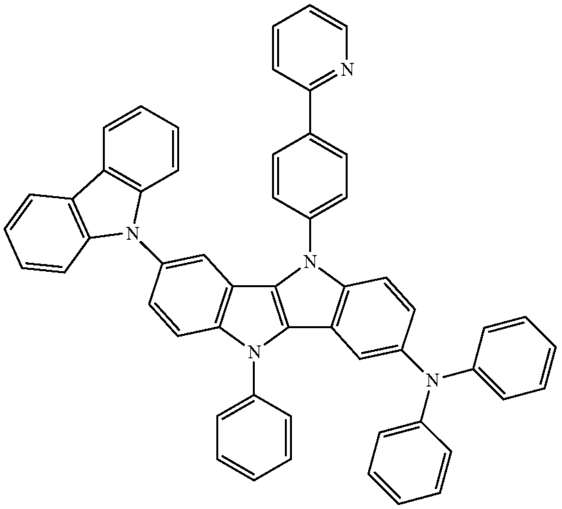
42
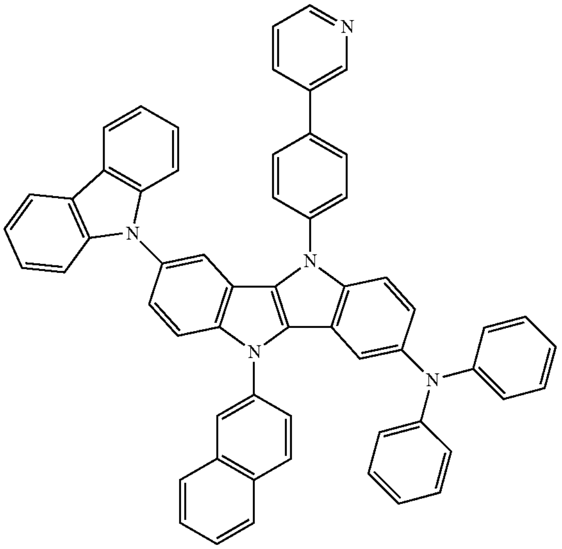

-continued
43
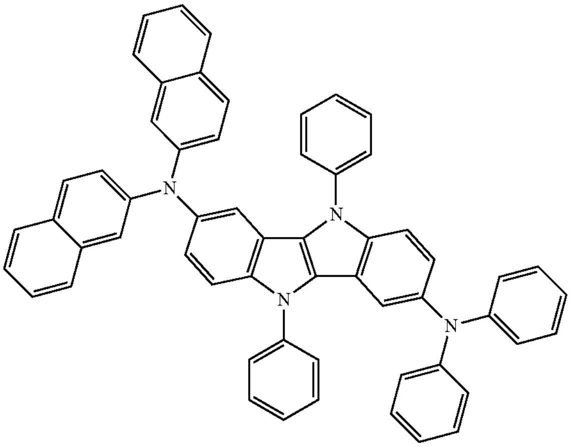
44
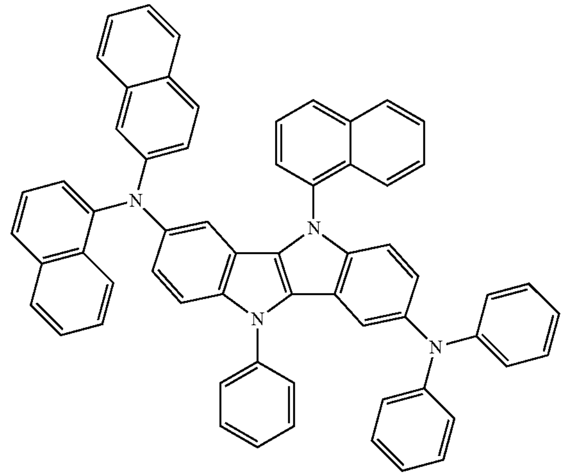
45
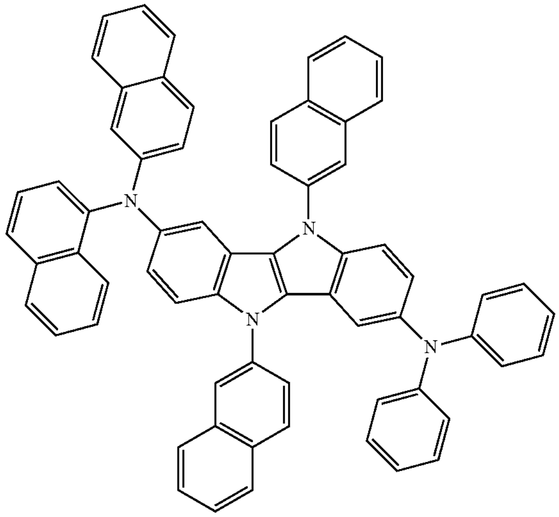
-continued
46
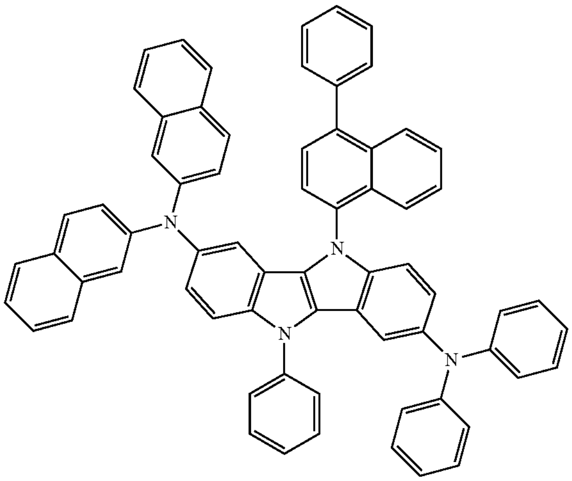
47
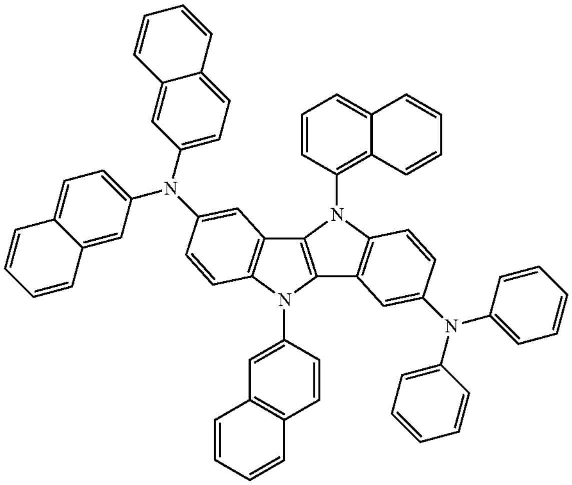
48
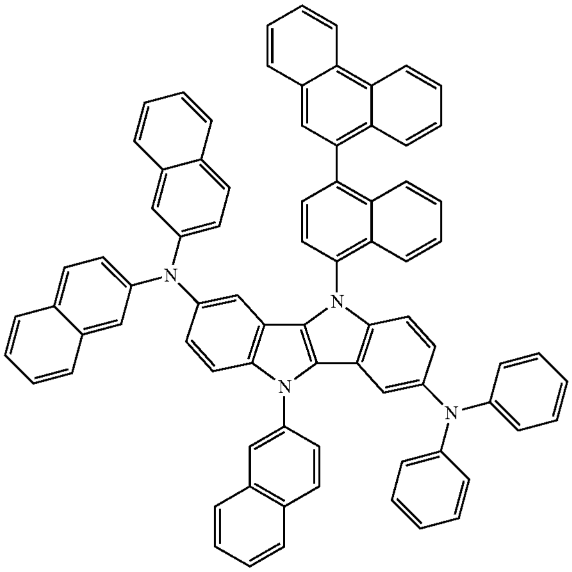

-continued
49
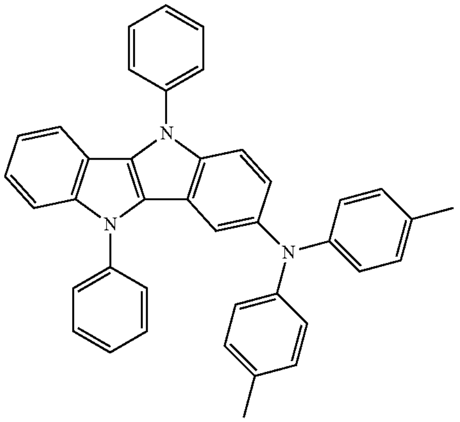
50
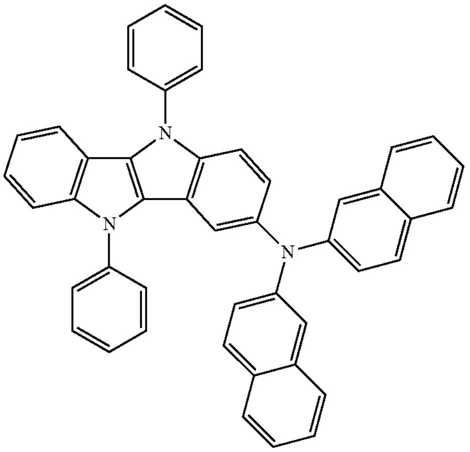
51
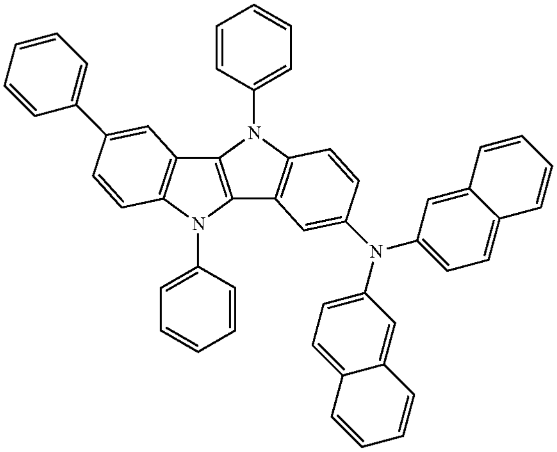
-continued
52
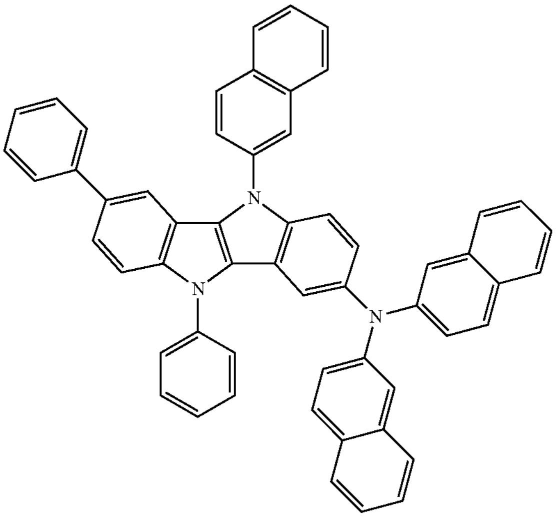
53
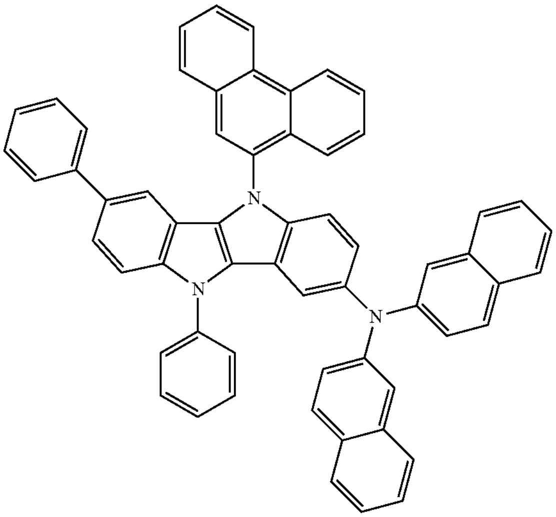

-continued
54
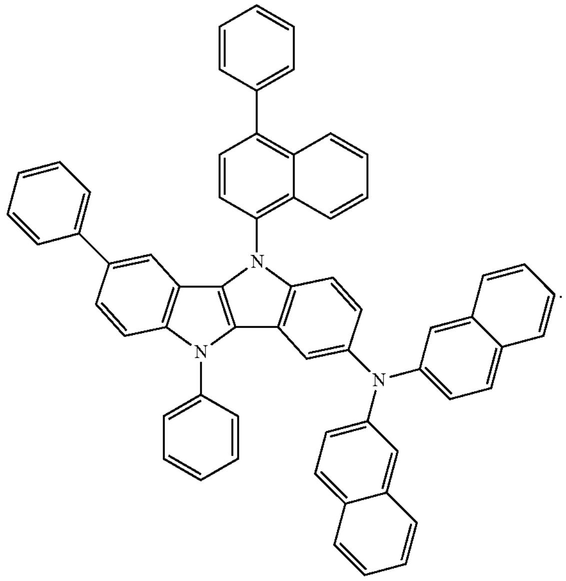
Examples of compounds represented by Formula 2 are as follows, but they are not limited thereto:
55
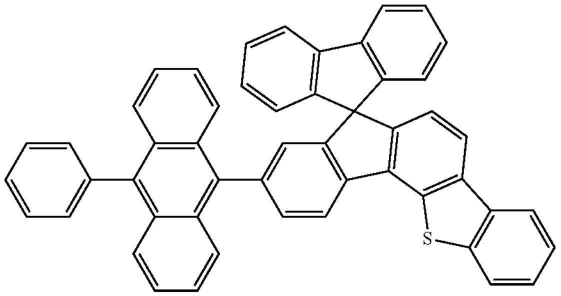
56
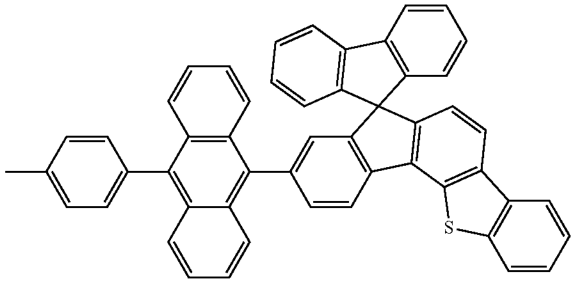
-continued
57
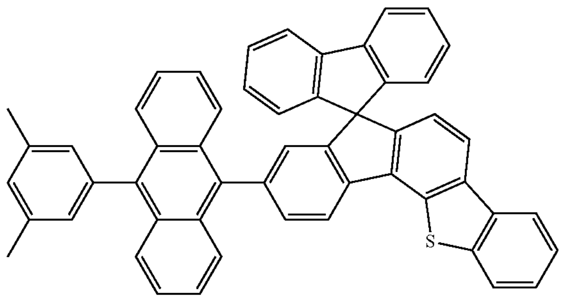
58
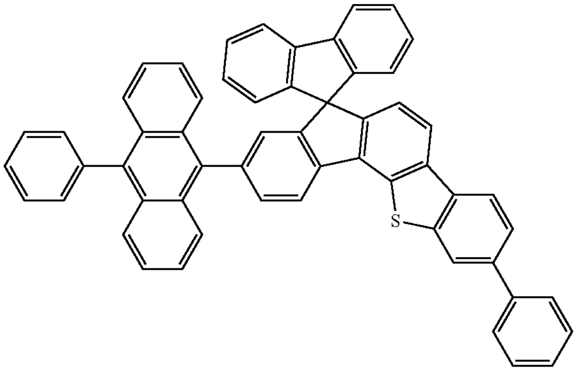
59
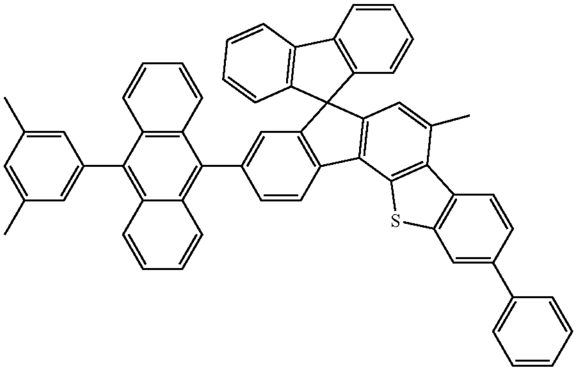
60
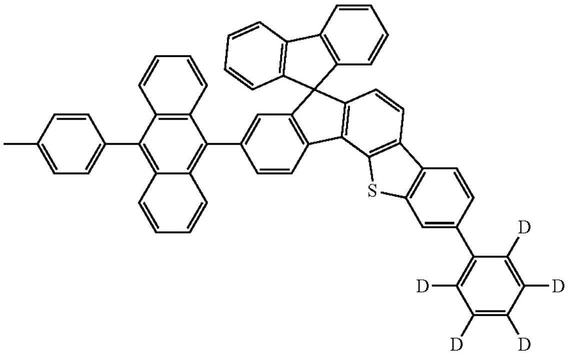

-continued
61
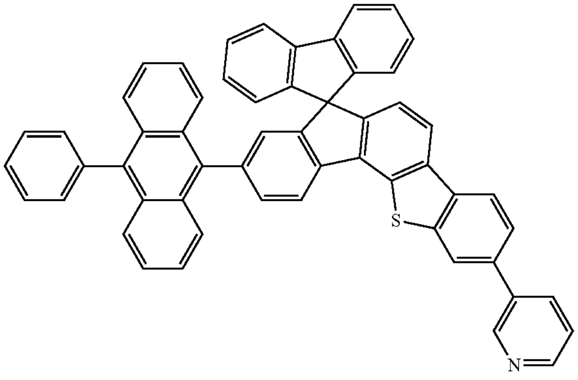
62
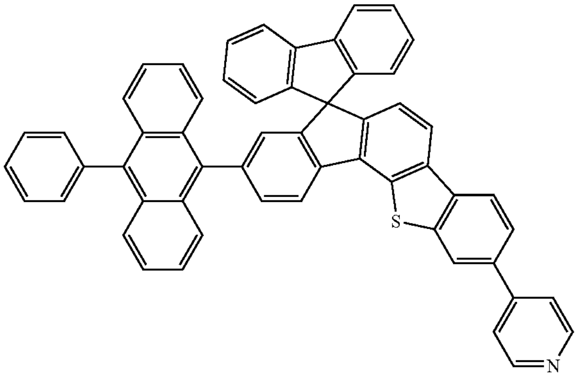
63
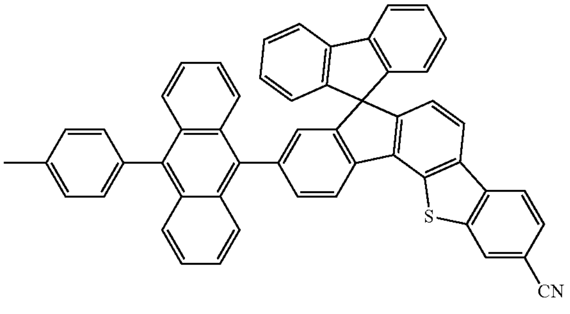
64
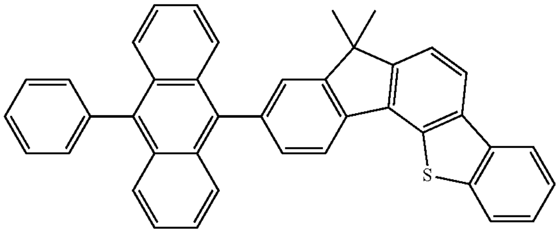
-continued
65
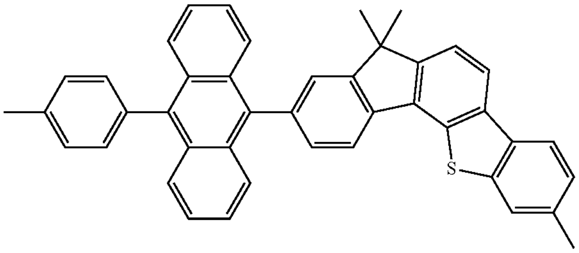
66
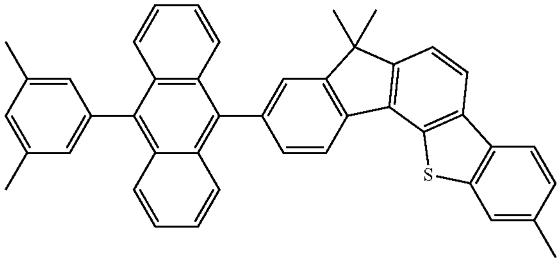
67
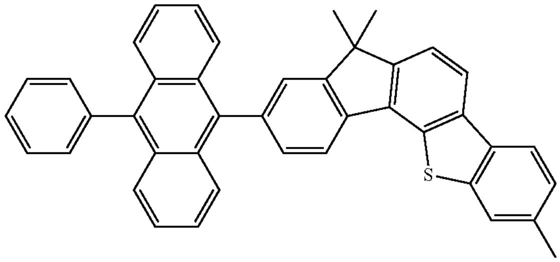
68
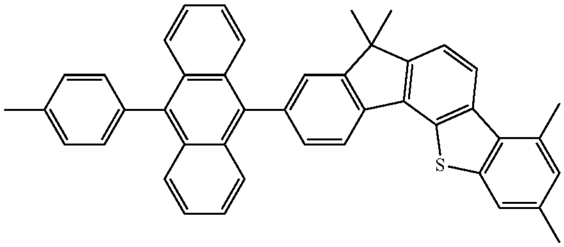
69
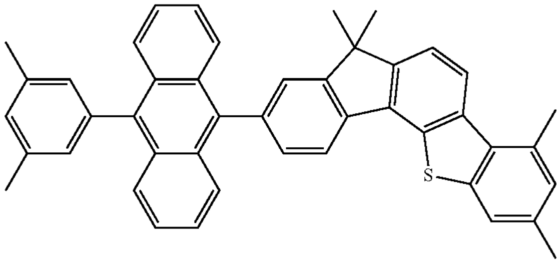

-continued
70
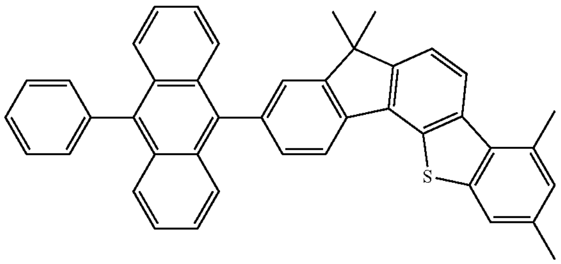
71
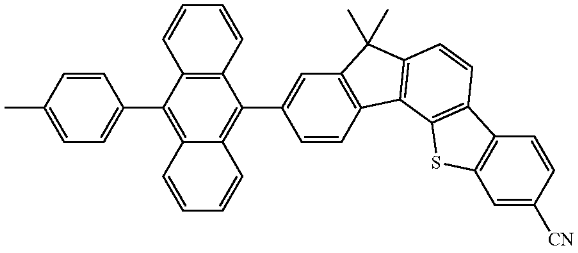
72
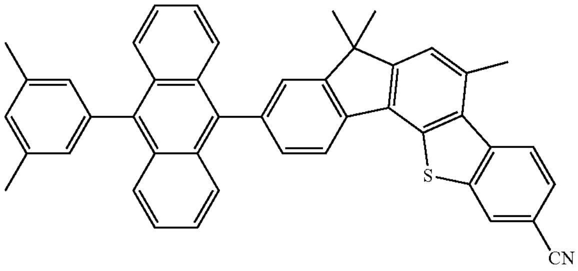
73
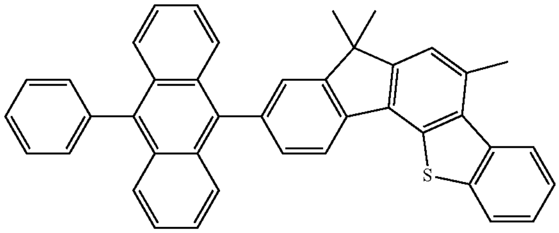
74
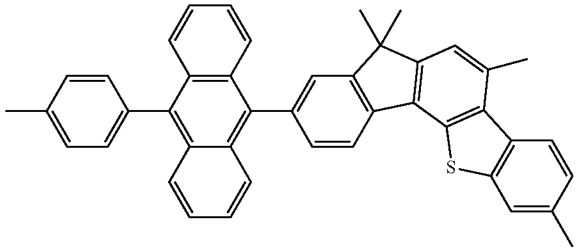
-continued
75
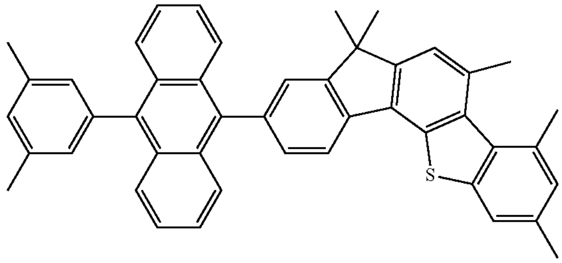
76
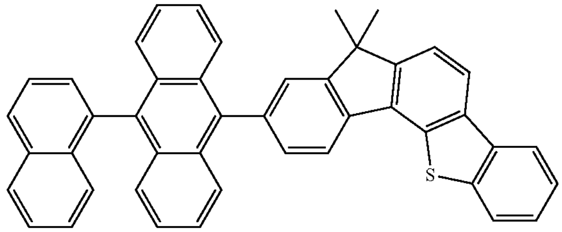
77
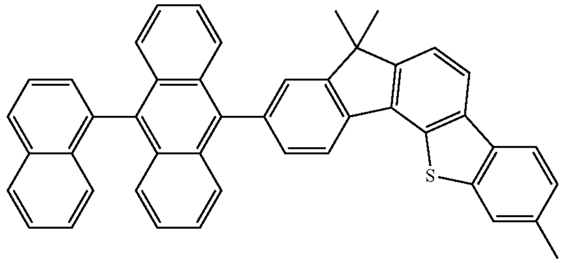
78
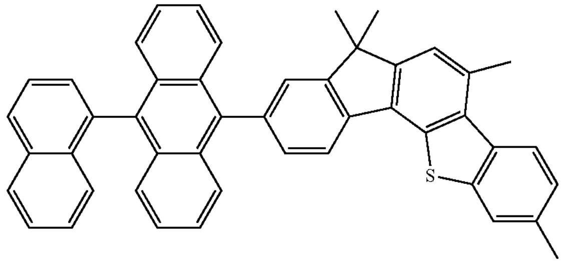
79
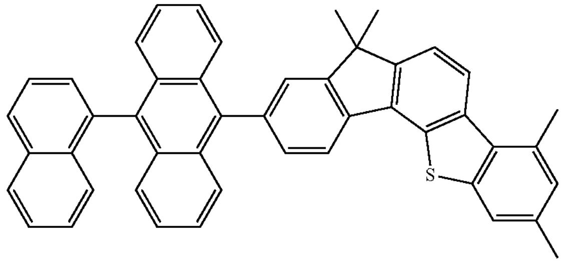

-continued
80
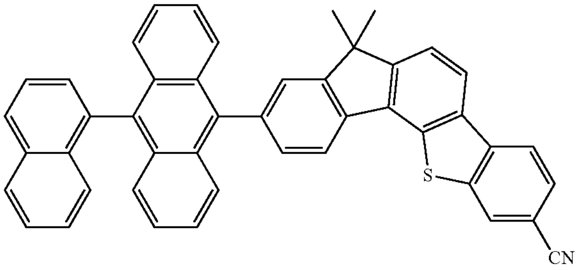
81
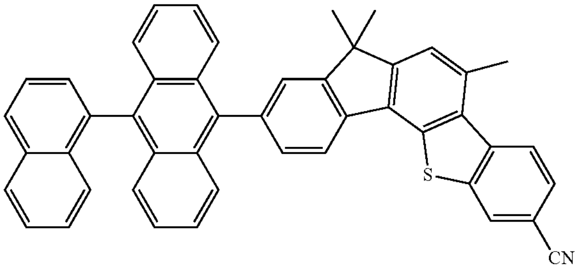
82
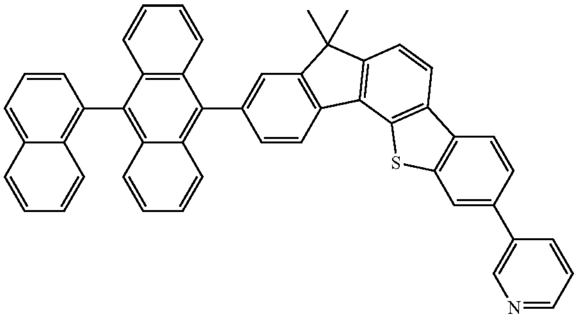
83
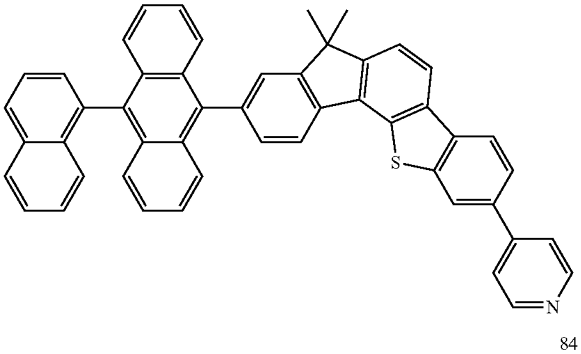
84
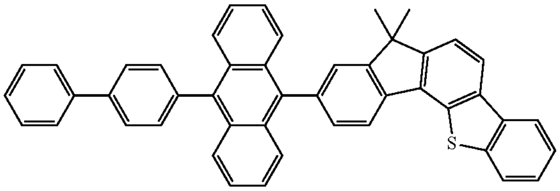
-continued
85
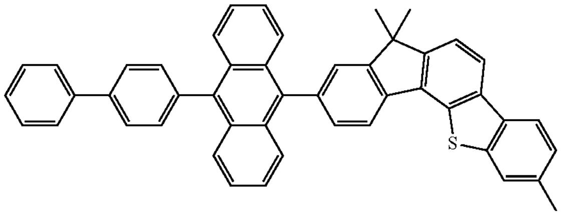
86
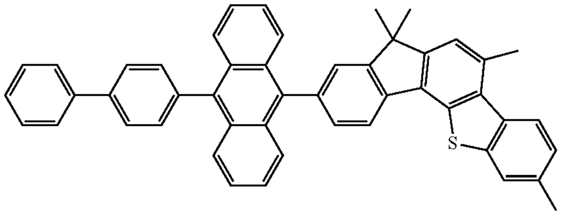
87
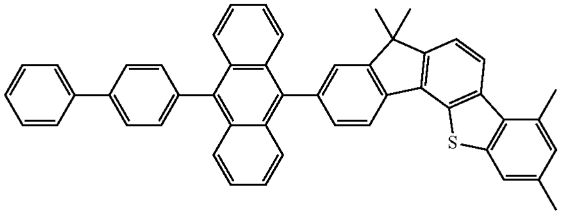
88
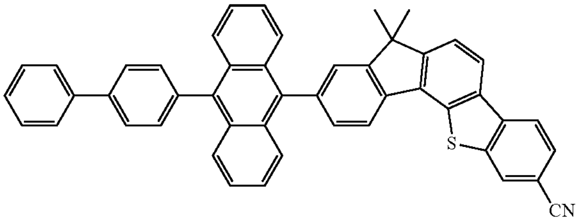
89
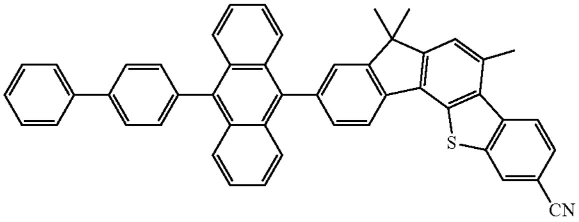
90
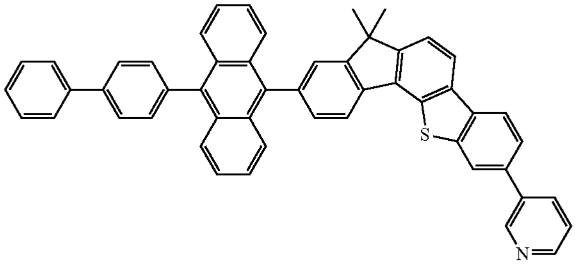

-continued
91
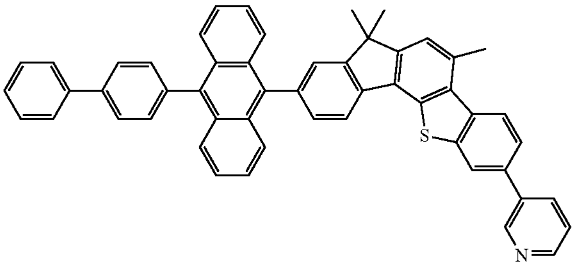
92
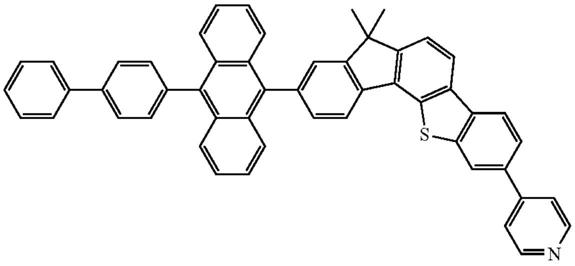
93
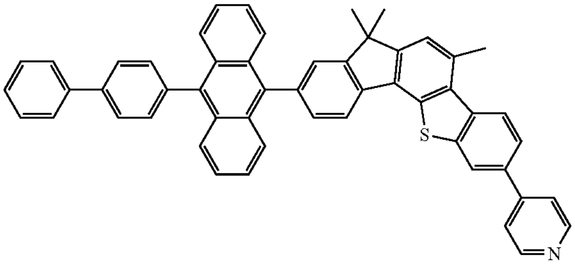
94
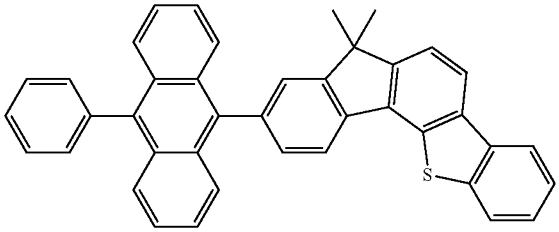
95
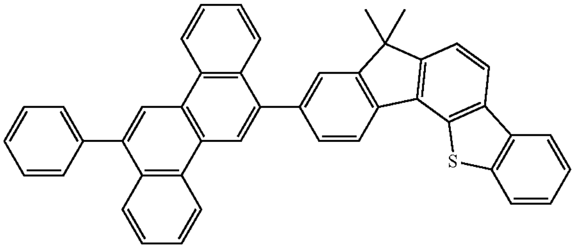
-continued
96
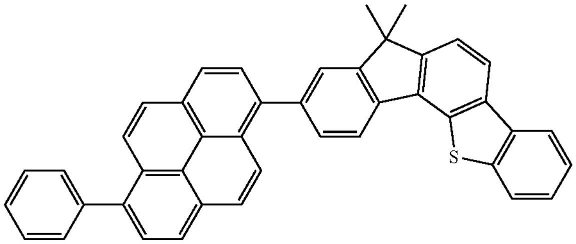
97
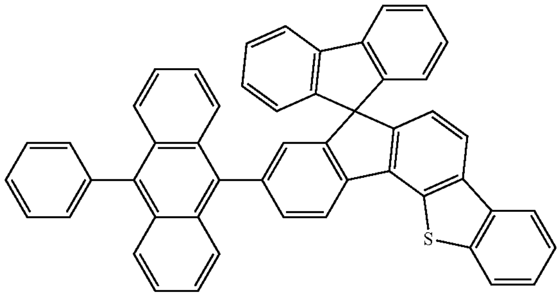
98
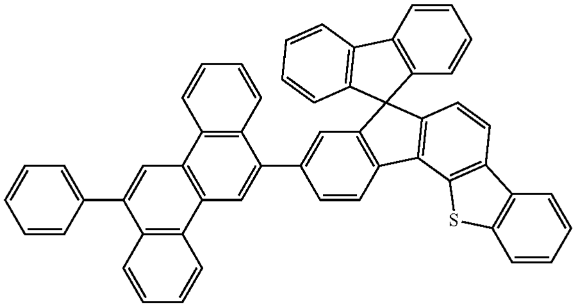
99
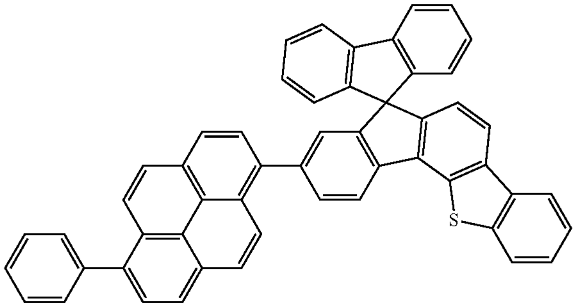
100
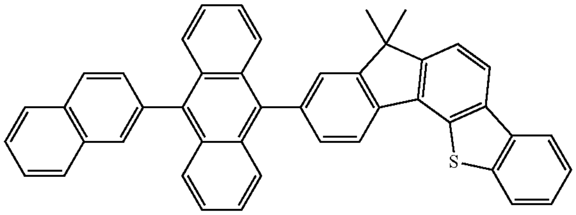

-continued

101

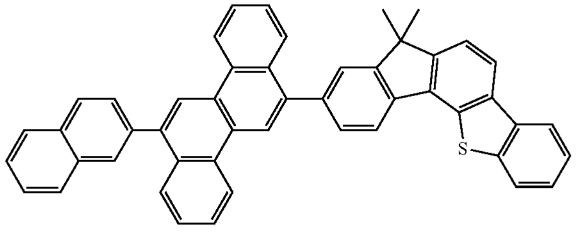

102

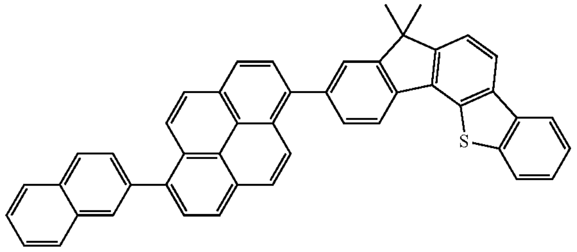

103

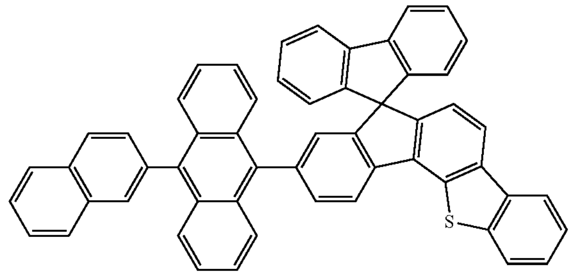

104

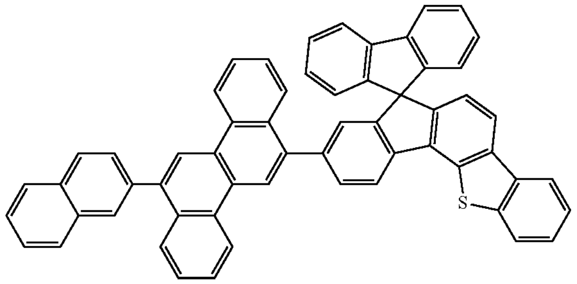

105

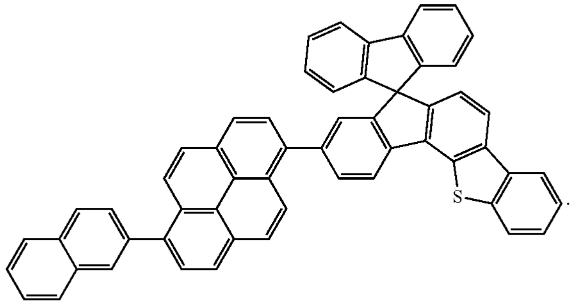

According to an embodiment of the present inventive concept, an organic layer of an organic light-emitting device includes at least one of a hole injection layer, a hole transport layer, a functional layer having both hole injection and hole transport capabilities (hereinafter, "H-functional layer"), a buffer layer, an electron blocking layer, a hole blocking layer, an electron transport layer, an electron injection layer, and a functional layer having both electron injection and electron transport capabilities (hereinafter, "E-functional layer").

In greater detail, the organic layer may be the emission layer. Specifically, the organic layer may be a blue emission layer.

According to an embodiment of the present inventive concept, the organic light-emitting device includes an electron injection layer, an electron transport layer, an emission layer, a hole injection layer, a hole transport layer, or an E-functional layer, and the E-functional layer includes a compound having electron injection and/or electron transport capabilities according to an embodiment of the present inventive concept, and the emission layer may include a compound according to an embodiment of the present inventive concept, one of an anthracene-based compound, an arylamine-based compound and a styryl-based compound.

According to another embodiment of the present inventive concept, the organic light-emitting device includes an electron injection layer, an electron transport layer, an emission layer, a hole injection layer, a hole transport layer, or an H-functional layer, and any one of a red layer, a green layer, a blue layer, and a white layer may include a phosphorescent compound, and the hole injection layer, the hole transport layer, or the H-functional layer may include a charge-generating material. The charge-generating material may be, for example, a p-dopant, and the p-dopant may be one of a quinone derivative, a metal oxide and a cyano group-containing compound.

According to another embodiment of the present inventive concept, the organic layer includes an electron transport layer, and the electron transport layer may include a metal complex. The metal complex may be a lithium (Li) complex.

The term "organic layer" as used herein refers to a single and/or multiple layers interposed between the first electrode and the second electrode of the organic light-emitting device.

FIG. 1 schematically illustrates a cross-section of an organic light-emitting device according to an embodiment of the present inventive concept. Hereinafter, a structure and a method of manufacturing the organic light-emitting device, according to an embodiment of the present inventive concept, will be described in detail with reference to FIG. 1.

A substrate (not shown) may be any substrate that is used in existing organic light-emitting devices. In some embodiments, the substrate may be a glass substrate or a transparent plastic substrate with strong mechanical strength, thermal stability, transparency, surface smoothness, ease of handling and water resistance.

A first electrode may be formed by depositing or sputtering a first electrode material onto a surface of the substrate. When the first electrode is an anode, a material having a high work function may be used as the first electrode material to facilitate hole injection. The first electrode may be a reflective electrode or a transmission electrode. Any of indium tin oxide (ITO), indium zinc oxide (IZO), $SnO_2$, ZnO and the like, which is transparent and has excellent conductivity, may be used as the first electrode material. The first electrode may be formed as a reflective electrode by using one of magnesium (Mg), aluminum (Al), aluminum-lithium (Al—Li), calcium (Ca), magnesium-indium (Mg—In), magnesium-silver (Mg—Ag) and the like.

The first electrode may have a single-layer structure or a multi-layer structure including at least two layers. For example, the first electrode may have a three-layered structure of ITO/Ag/ITO, but it is not limited thereto.

An organic layer may be disposed on the first electrode.

The organic layer may include a hole injection layer, a hole transport layer, a buffer layer (not shown), an emission layer, an electron transport layer, an electron injection layer, and the like.

The hole injection layer may be formed on the first electrode by using various methods, such as vacuum deposition, spin coating, casting, Langmuir-Blodgett (LB) deposition, and the like.

When the hole injection layer is formed using vacuum deposition, vacuum deposition conditions may vary according to the compound that is used to form the hole injection layer and the desired structure and thermal properties of the hole injection layer to be formed. For example, the vacuum deposition may be performed at a temperature of about 100° C. to about 500° C., a pressure of about $10^{-8}$ torr to about $10^{-3}$ torr, and a deposition rate of about 0.01 Å/sec to about 100 Å/sec. However, the deposition conditions are not limited thereto.

When the hole injection layer is formed using spin coating, the coating conditions may vary according to the compound that is used to form the hole injection layer and the desired structure and thermal properties of the hole injection layer to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The hole injection layer may be formed of any hole injection material including those that are commonly used. Non-limiting examples of the hole injection material are N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl-N,N'-diphenylbenzidine) (NPB), 4,4',4"-tris(N,N-diphenylamino)triphenylamine (TDATA), 4,4',4"-tris-(N-(naphthylen-2-yl)-N-phenylamino)triphenylamine (2-TNATA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and (polyaniline)/poly(4-styrenesulfonate) (PANI/PSS):

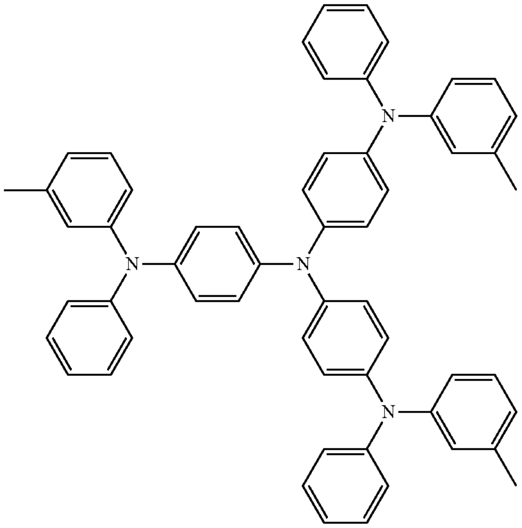

m-MTDATA

-continued

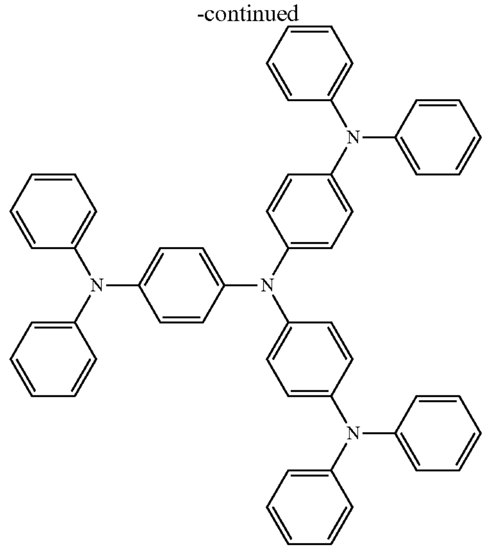

TDATA

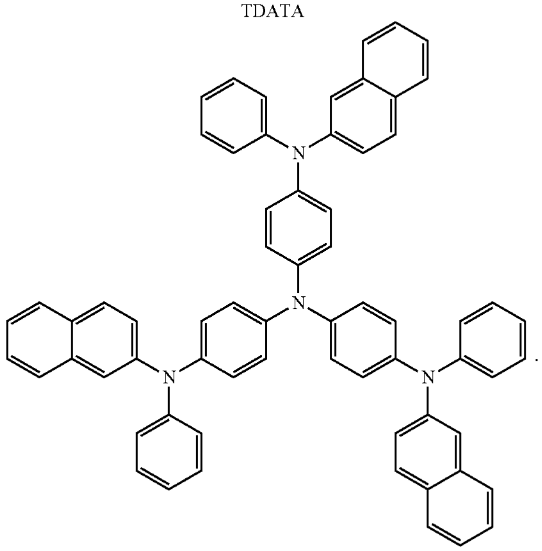

2-TNATA

A thickness of the hole injection layer may be from about 100 Å to about 10000 Å, and, in some embodiments, may be from about 100 Å to about 1000 Å. When the thickness of the hole injection layer is within these ranges, the hole injection layer may have good hole injecting ability without imparting a substantial increase in driving voltage to the corresponding OLED.

Then, the hole transport layer may be formed on the hole injection layer by using various methods, such as one of vacuum deposition, spin coating, casting, LB deposition and the like. When the hole transport layer is formed using one of vacuum deposition and spin coating, the conditions for deposition and coating may be similar to those for the formation of the hole injection layer, though the conditions for the deposition and coating may vary according to the compound that is used to form the hole transport layer.

Non-limiting examples of suitable known hole transport materials are carbazole derivatives, such as N-phenylcarbazole or polyvinylcarbazole, N,N'-bis(3-methylphenyl-N,N'-diphenyl-[1,1-biphenyl]-4,4'-diamine (TPD), 4,4',4"-tris(N-carbazolyl)triphenylamine (TCTA), and N,N'-di(1-naphthyl-N,N'-diphenylbenzidine) (NPB).

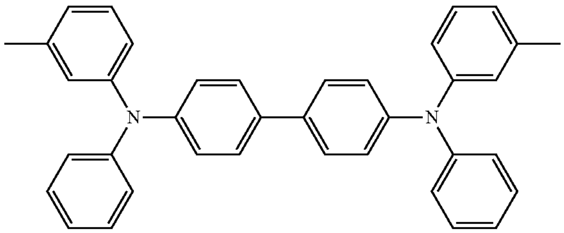

TPD

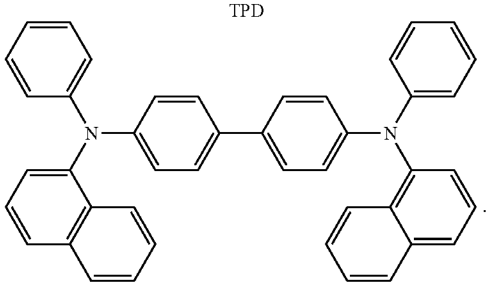

NPB

A thickness of the hole transport layer may be from about 50 Å to about 2000 Å, and, in some embodiments, may be from about 100 Å to about 1500 Å. When the thickness of the hole transport layer is within these ranges, the hole transport layer may have good hole transporting ability without imparting a substantial increase in driving voltage to the corresponding OLED.

An H-functional layer may include at least one material from each of the hole injection layer materials and hole transport layer materials. The thickness of the H-functional layer may be from about 500 Å to about 10,000 Å, and, in some embodiments, may be from about 100 Å to about 1000 Å. When the thickness of the H-functional layer is within these ranges, the H-functional layer may have good hole injection and hole transport capabilities without imparting a substantial increase in driving voltage to the corresponding OLED.

In some embodiments, at least one of the hole injection layer, the hole transport layer, and the H-functional layer may include at least one of a compound of Formula 300 and a compound of Formula 350:

<Formula 300>

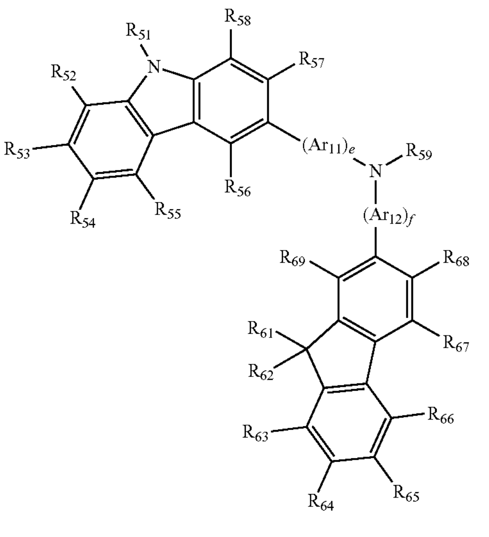

-continued

<Formula 350>

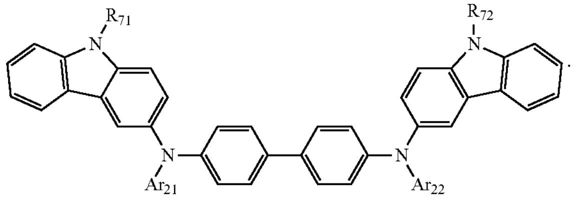

In Formulae 300 and 350, $Ar_{11}$, $Ar_{12}$, $Ar_{21}$, and $Ar_{22}$ may be each independently a substituted or unsubstituted $C_5$-$C_{60}$ arylene group.

In Formula 300, e and f may be each independently an integer of 0 to 5, or 0, 1, or 2. For example, e may be f, and f may be 0, but they are not limited thereto.

In Formulae 300 and 350 above, $R_{51}$ to $R_{58}$, $R_{61}$ to $R_{69}$, $R_{71}$, and $R_{72}$ may be each independently one of a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C3-C60 cycloalkyl group, a substituted or unsubstituted C5-C60 aryl group, a substituted or unsubstituted C5-C60 aryloxy group and a substituted or unsubstituted C5-C60 arylthio group. For example, $R_{51}$ to $R_{58}$, $R_{61}$ to $R_{69}$, and $R_{71}$ and $R_{72}$ may be each independently one of a hydrogen atom; a deuterium atom; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a C1-C10 alkyl group (for example, a methyl group, an ethyl group, a propyl group, a butyl group, a pentyl group, a hexyl group, or the like);

a C1-C10 alkoxy group (for example, a methoxy group, an ethoxy group, a propoxy group, a butoxy group, a pentoxy group, or the like);

a C1-C10 alkyl group and a C1-C10 alkoxy group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, and a phosphoric acid or a salt thereof;

a phenyl group; a naphthyl group; an anthryl group; a fluorenyl group; a pyrenyl group; and a phenyl group, a naphthyl group, an anthryl group, a fluorenyl group and a pyrenyl group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a C1-C10 alkyl group, and a C1-C10 alkoxy group, but they are not limited thereto.

In Formula 300, $R_{59}$ may be one of a phenyl group; a naphthyl group; an anthryl group; a biphenyl group; a pyridyl group; and a phenyl group, a naphthyl group, an anthryl group, a biphenyl group and a pyridyl group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted C1-C20 alkyl group, and a substituted or unsubstituted C1-C20 alkoxy group.

According to an embodiment of the present inventive concept, the compound of Formula 300 may be a compound represented by Formula 300A, but it is not limited thereto:

<Formula 300A>

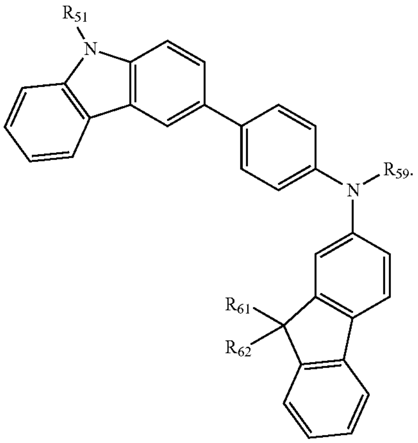

In Formula 300A, a detailed description of $R_{51}$, $R_{59}$, $R_{61}$, and $R_{62}$ may be as defined above.

In some non-limiting embodiments, at least one of the hole injection layer, the hole transport layer, and the H-functional layer may include at least one of the compounds represented by Formulae 301 to 320, but they are not limited thereto:

301

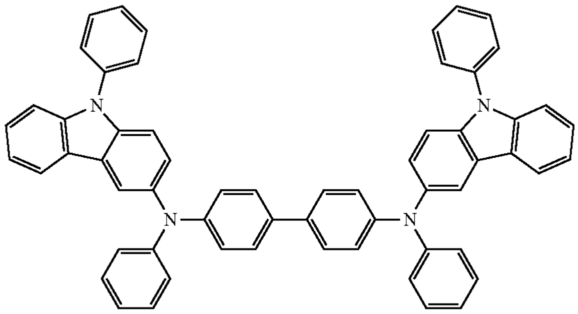

302

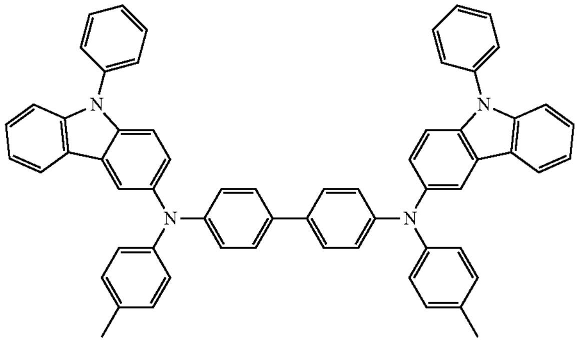

-continued

303

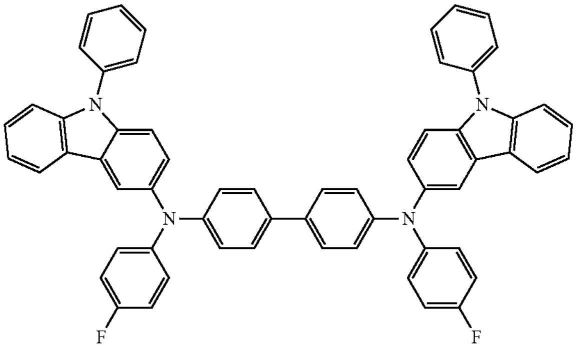

304

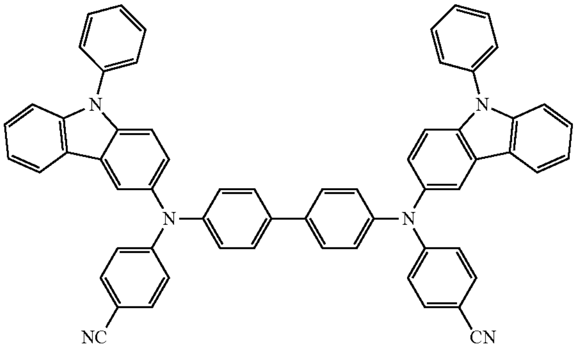

305

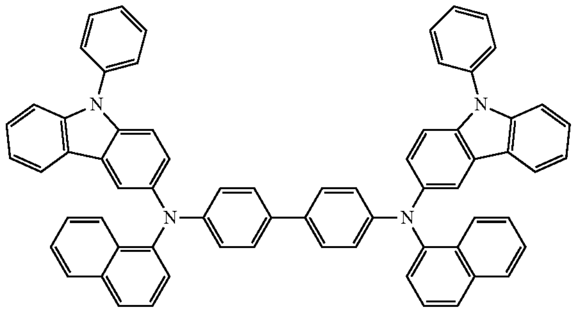

306

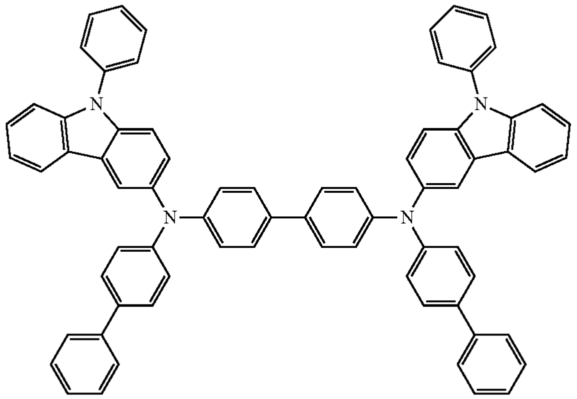

-continued
307
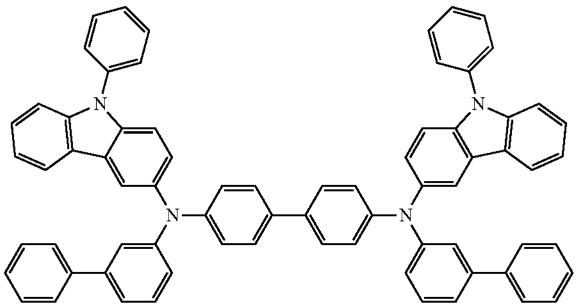
308
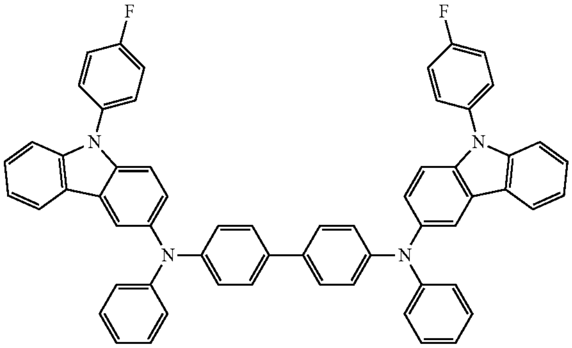
309
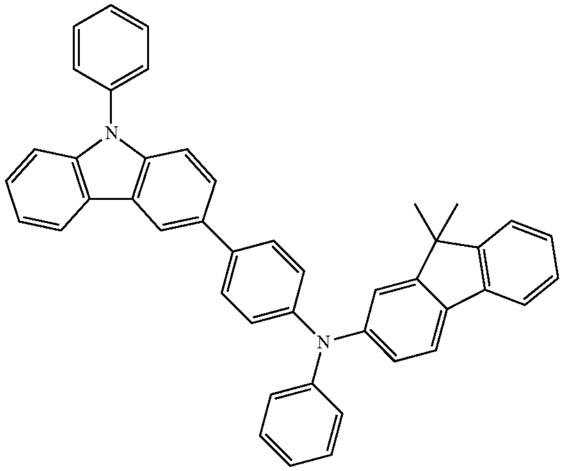
-continued
310
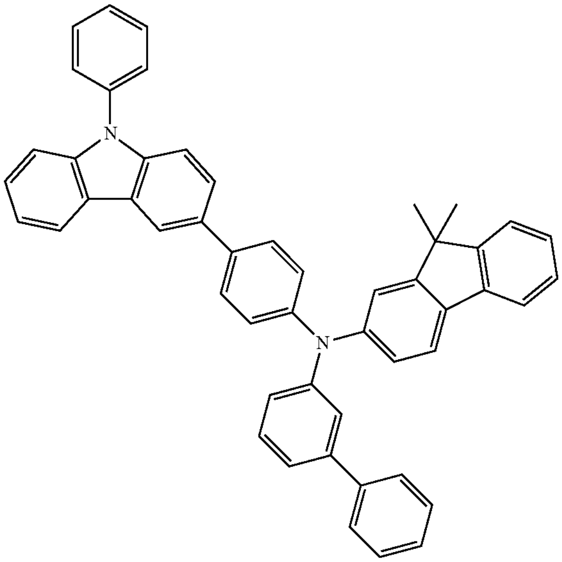
311
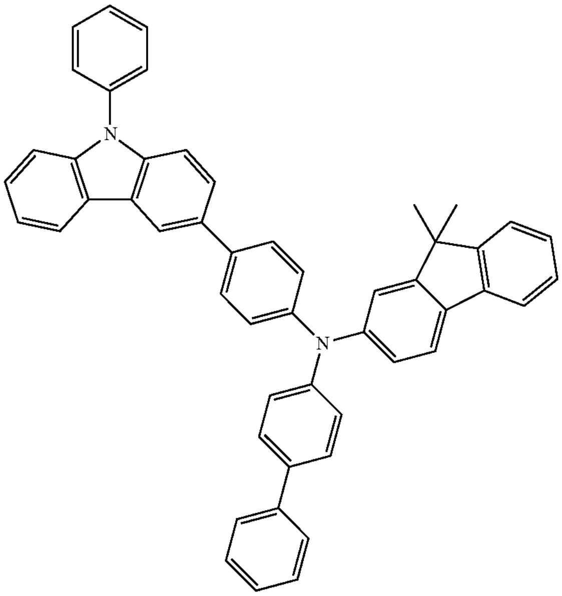

-continued
312
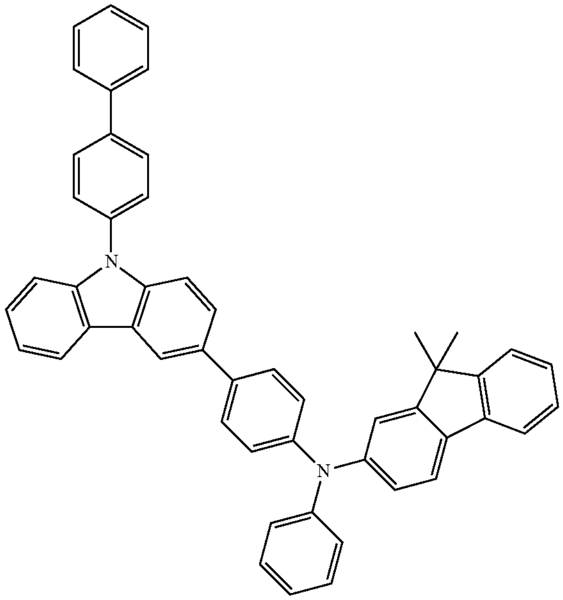
313
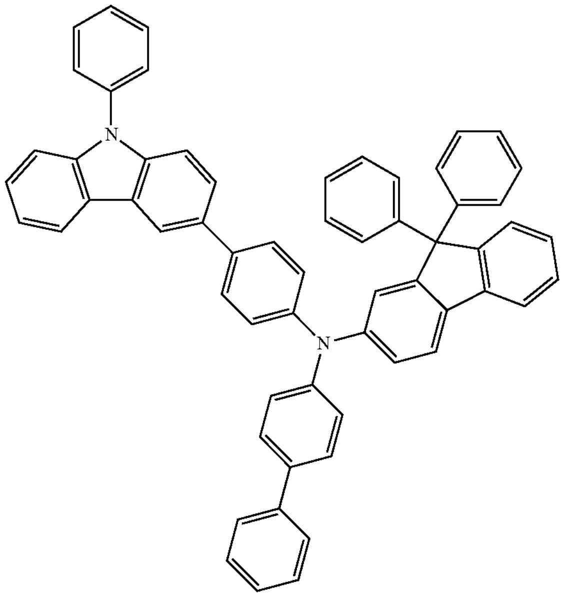
-continued
314
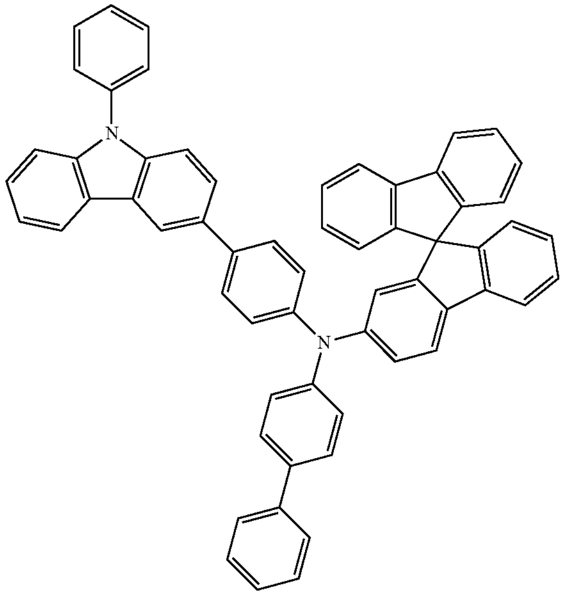
315
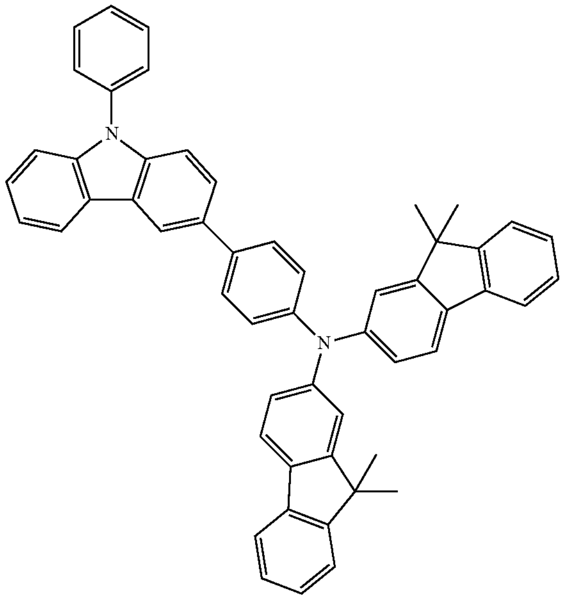

-continued

316

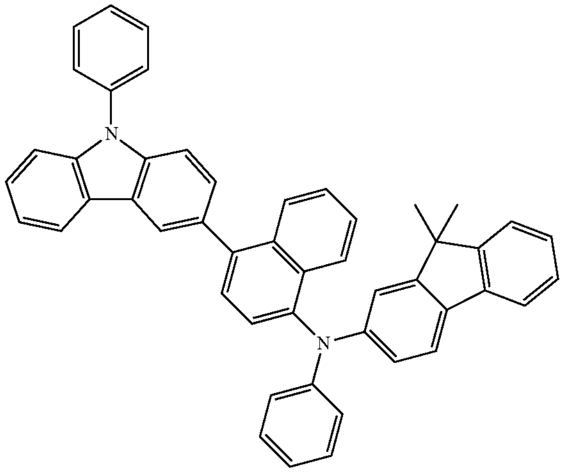

317

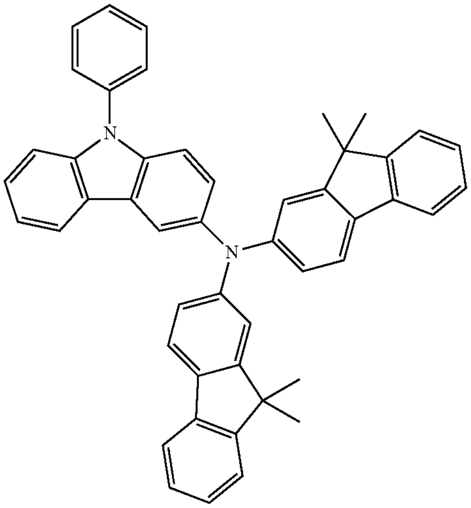

318

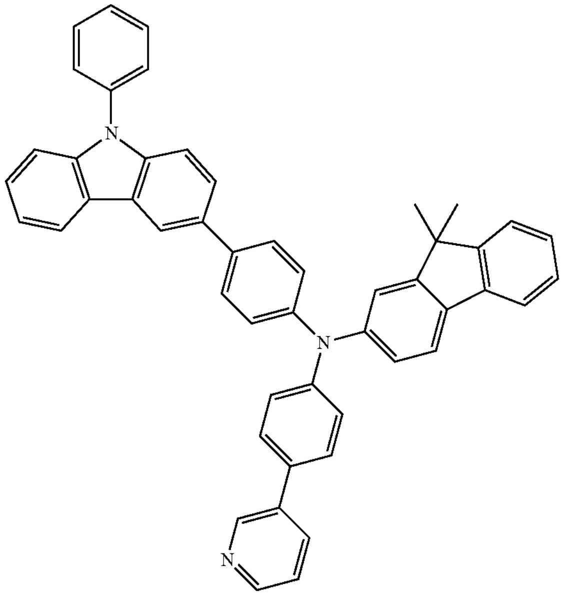

-continued

319

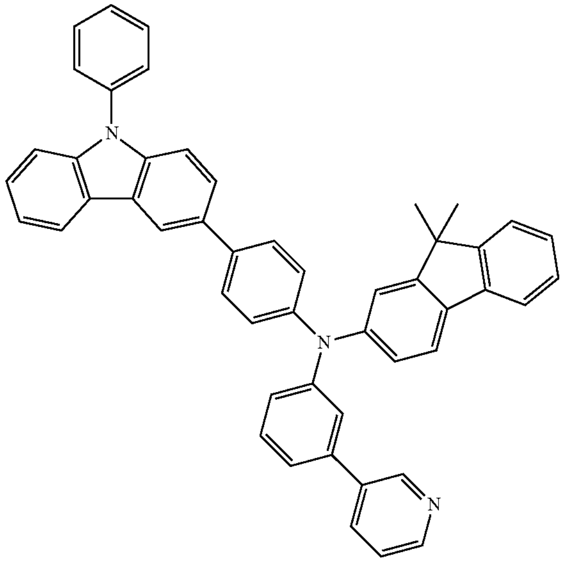

320

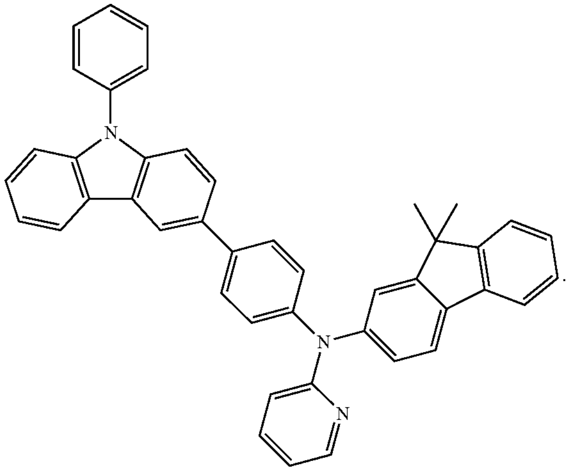

At least one of the hole injection layer, the hole transport layer, and the H-functional layer may further include a charge-generating material to improve layer conductivity, in addition to a hole injection material, a hole transport material, and/or a material having both hole injection and hole transport capabilities as described above.

The charge-generating material may be, for example, a p-dopant. The p-dopant may be one of a quinone derivative, a metal oxide and a cyano-containing compound, but it is not limited thereto. Non-limiting examples of the p-dopant include quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

<Compound 200>

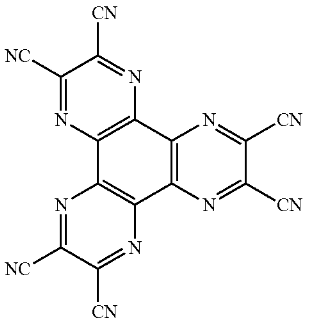

<F4-TCNQ>

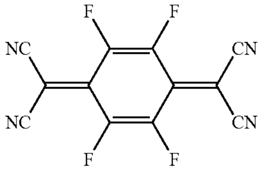

When one of the hole injection layer, the hole transport layer and the H-functional layer further includes the charge-generating material, the charge-generating material may be homogeneously dispersed or inhomogeneously distributed in the one of the hole injection layer, the hole transport layer and the H-functional layer.

A buffer layer (not shown) may be interposed between the emission layer and at least one of the hole injection layer, the hole transport layer and the H-functional layer. The buffer layer may compensate for an optical resonance distance of light according to a wavelength of the light emitted from the emission layer and thus may increase efficiency. The buffer layer may include one of a hole injection material and a hole transport material. In some other embodiments, the buffer layer may include the same material as one of the materials included in the hole injection layer, the hole transport layer, and the H-functional layer that underlie the buffer layer.

Then, the emission layer may be formed on the hole transport layer, the H-functional layer, or the buffer layer by one of vacuum deposition, spin coating, casting, LB deposition and the like. When the emission layer is formed by using vacuum deposition or spin coating, the deposition and coating conditions may be similar to those for the formation of the hole injection layer, though the conditions for deposition and coating may vary according to the material that is used to form the emission layer.

The emission layer may include a compound according to the present inventive concept. For example, a compound represented by Formula 1 and a compound represented by Formula 2 may be used as a host and a dopant, respectively. The emission layer may be formed by using various emission materials other than the compounds represented by Formula 1 and Formula 2, and may be formed by using a host and a dopant. As the dopant, a fluorescent dopant and a phosphorescent dopant may both be used.

For example, as a host, tris(8-hydroxyquinolinato)aluminum ($Alq_3$), 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), 2,7-bis(9,9-diethylfluoren-2-yl)-9,9-diethylfluorene (E3), distyrylarylene (DSA), 4,4'-biscarbazolyl-2,2'-dimethylbiphenyl (dmCBP), and Compounds 501 to 509 below may be used, but the host is not limited thereto.

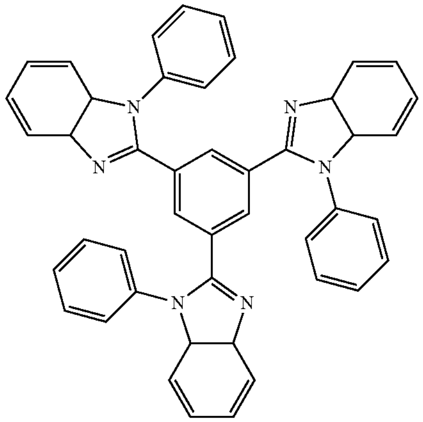

TPBI

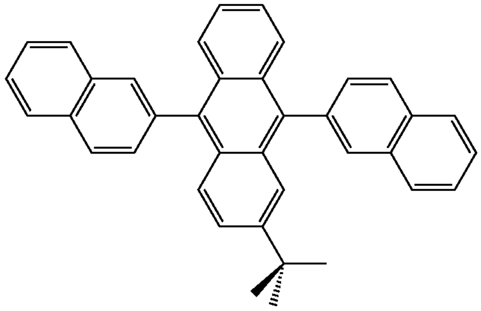

TBADN

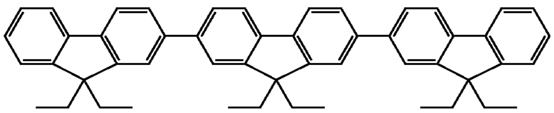

E3

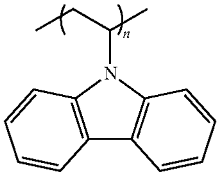

PVK

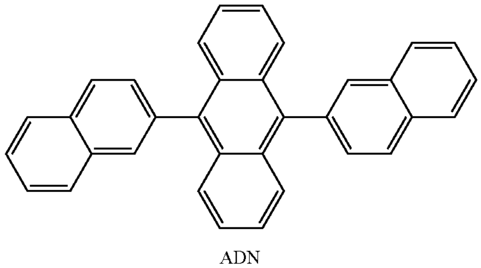

ADN

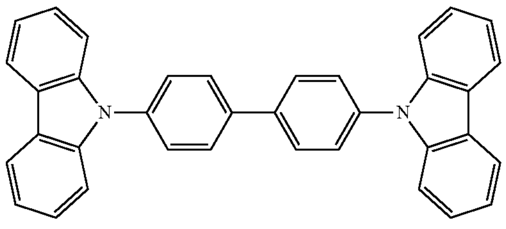

CBP

-continued
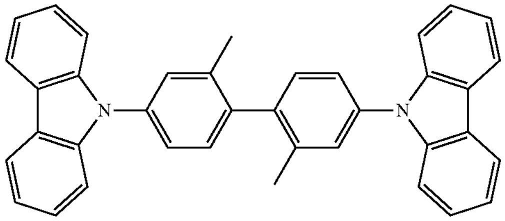
dmCBP
501
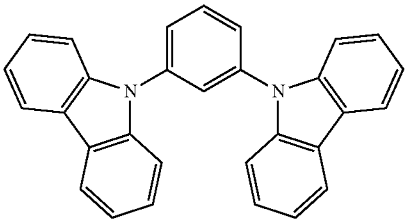
502
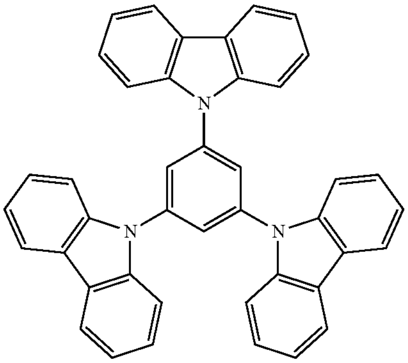
503
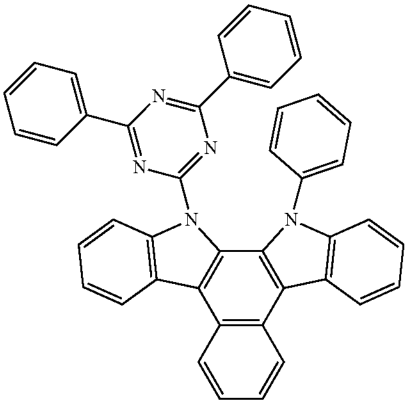
-continued
504
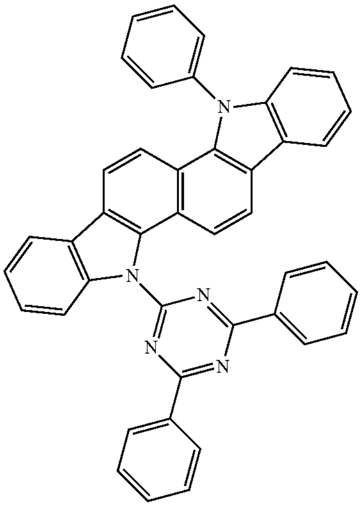
505
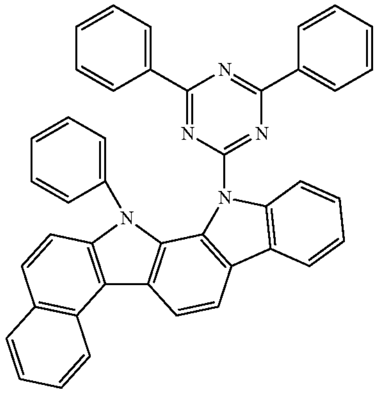
506
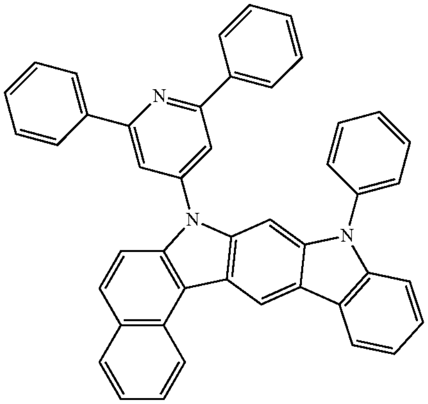

-continued

507

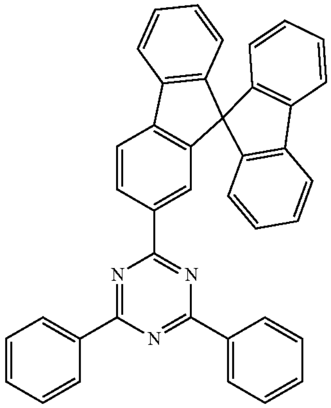

508

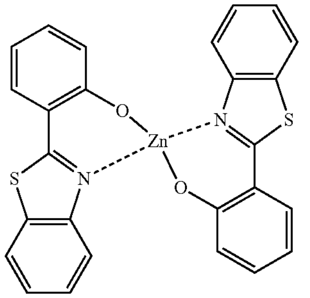

509

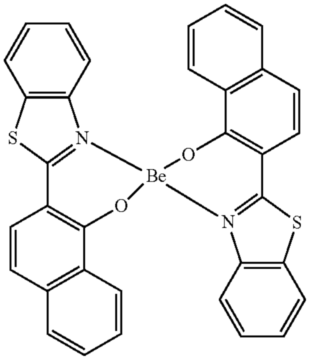

In some embodiments, an anthracene-based compound represented by Formula 400 may be used as the host:

<Formula 400>

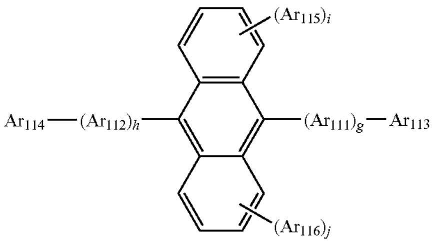

In Formula 400, $Ar_{111}$ and $Ar_{112}$ may be each independently a substituted or unsubstituted $C_5$-$C_{60}$ arylene group; $Ar_{113}$ to $Ar_{116}$ may be each independently one of a substituted or unsubstituted $C_1$-$C_{10}$ alkyl group and a substituted or unsubstituted $C_5$-$C_{60}$ aryl group; and g, h, i, and j may be each independently an integer of 0 to 4.

For example, in Formula 400 above, $Ar_{111}$ and $Ar_{112}$ may be one of a phenylene group, a naphthylene group, a phenanthrenylene group and a pyrenylene group; and one of a phenylene group, a naphthylene group, a phenanthrenylene group, a fluorenyl group and a pyrenylene group, each substituted with at least one of a phenyl group, a naphthyl group and an anthryl group, but they are not limited thereto.

In Formula 400, g, h, i, and j may be each independently 0, 1 or 2.

In Formula 400 above, $Ar_{113}$ to $Ar_{116}$ may be each independently a C1-C10 alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group and a fluorenyl group, each substituted with at least one of a deuterium atom, a halogen atom, a hydroxyl group, a cyano group, a nitro group, an amino group, an amidino group, hydrazine, hydrazone, a carboxyl group, or a salt thereof, a sulfonic acid group or a salt thereof, a phosphoric acid or a salt thereof, a C1-C60 alkyl group, a C2-C60 alkenyl group, a C2-C60 alkynyl group, a C1-C60 alkoxy group, a phenyl group, a naphthyl group, an anthryl group, a pyrenyl group, a phenanthrenyl group and a fluorenyl group; and

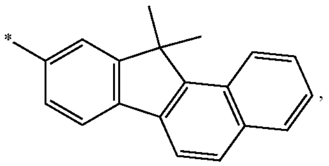 [SMILES: *c1ccc2c(c1)C(C)(C)c1c-2ccc2ccccc12]

but they are not limited thereto.

For example, an anthracene-based compound represented by Formula 400 may be one of the compounds below, but it is not limited thereto:

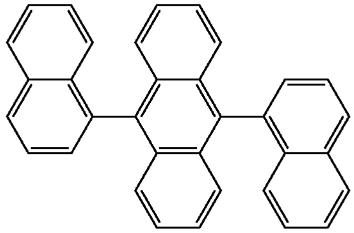

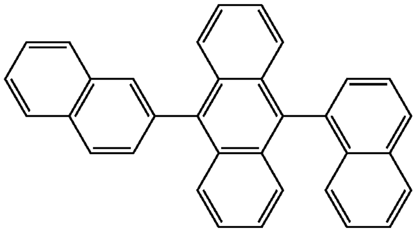

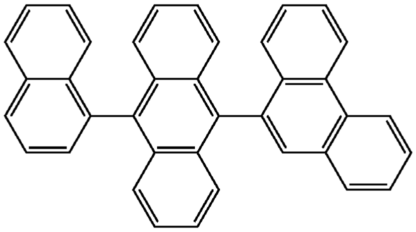

-continued
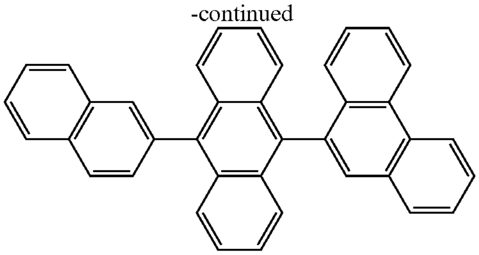
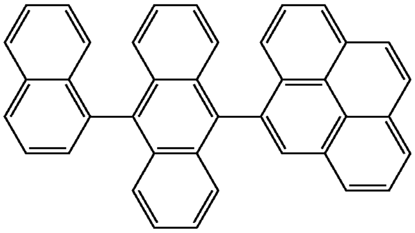
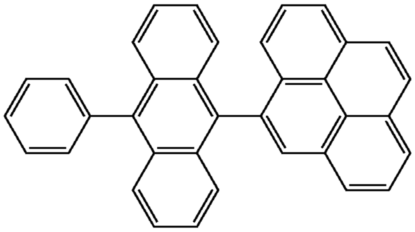
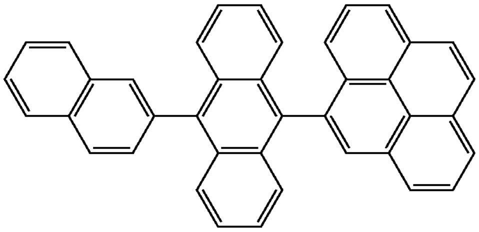
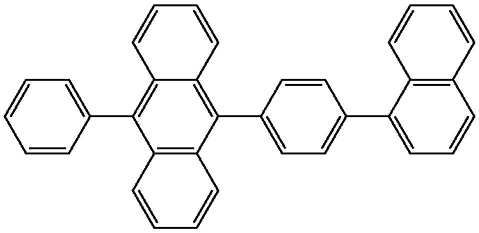
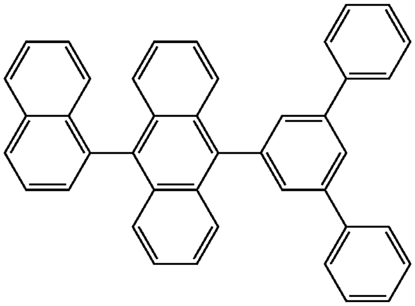
-continued
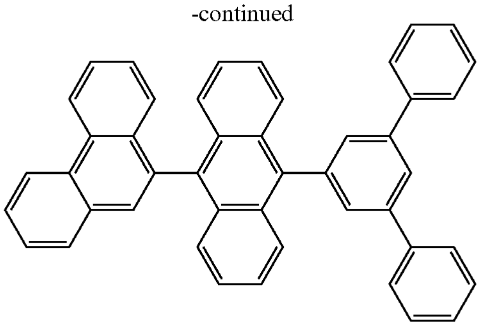
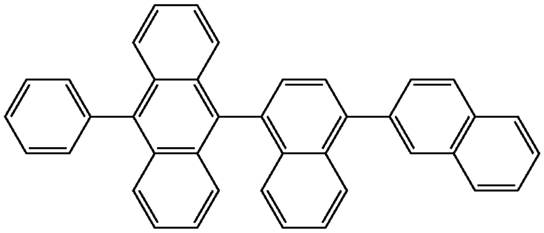
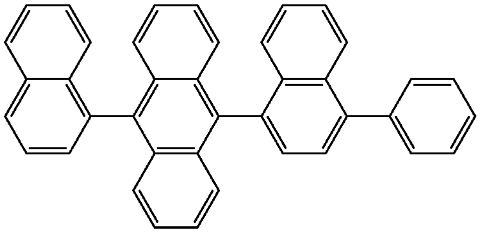
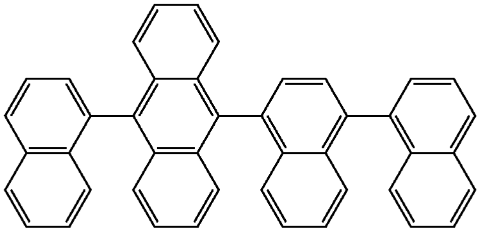
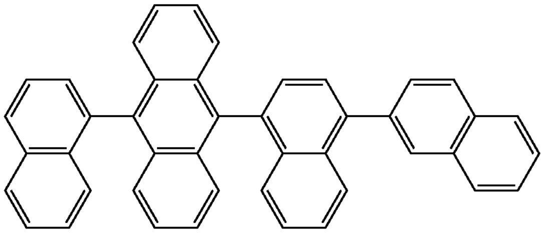
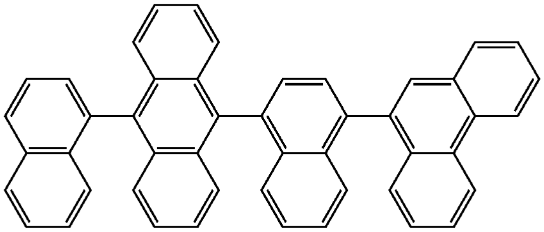
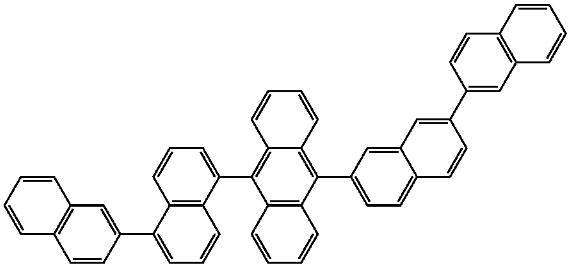

-continued
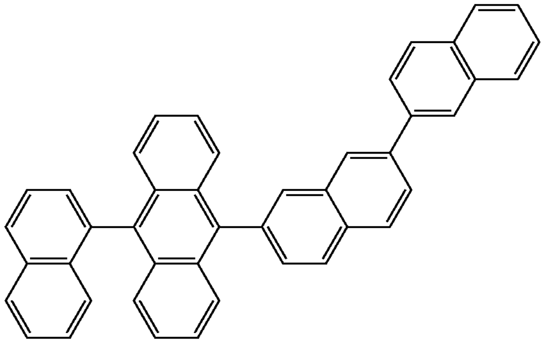
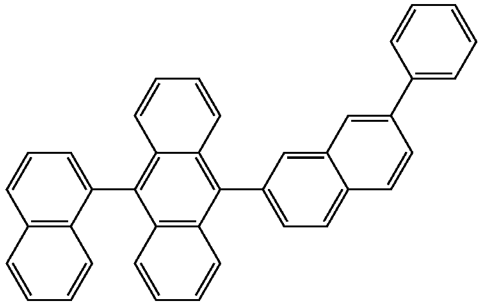
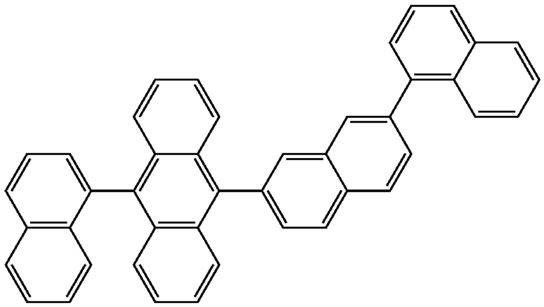
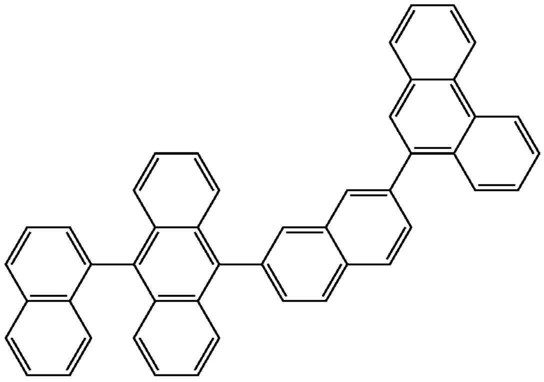
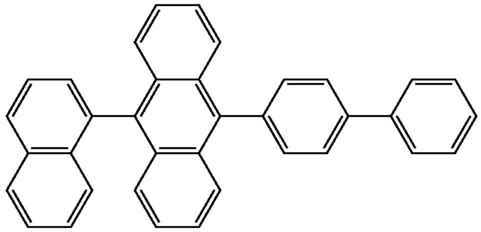
-continued
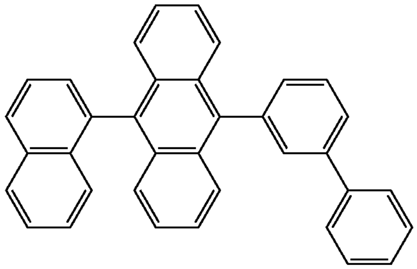
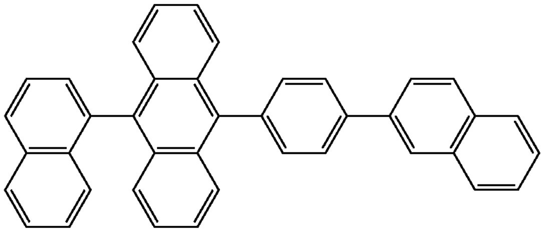
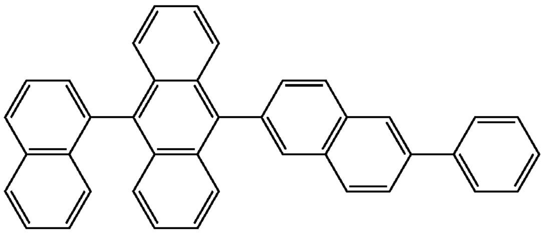
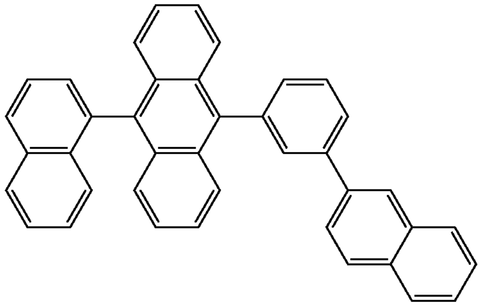
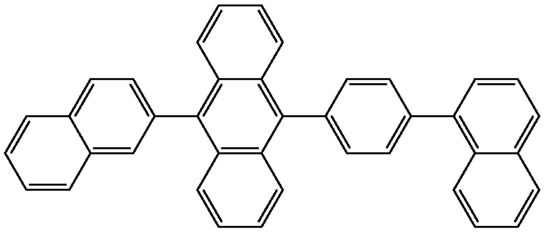
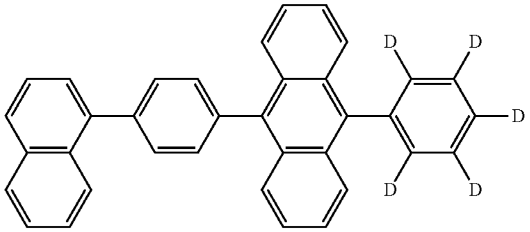
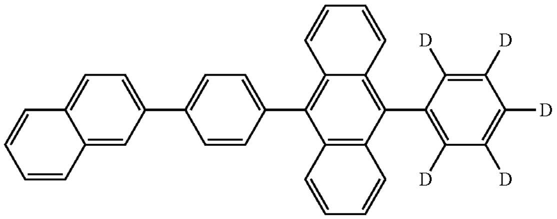

-continued
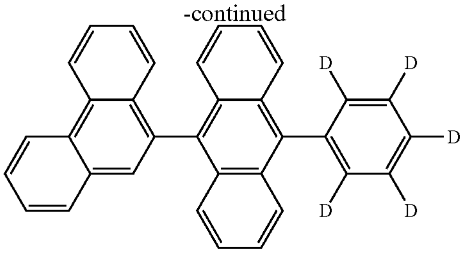
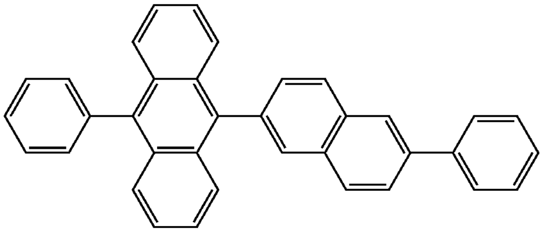
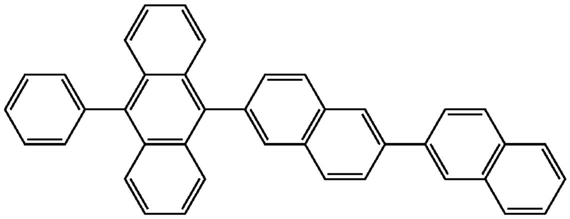
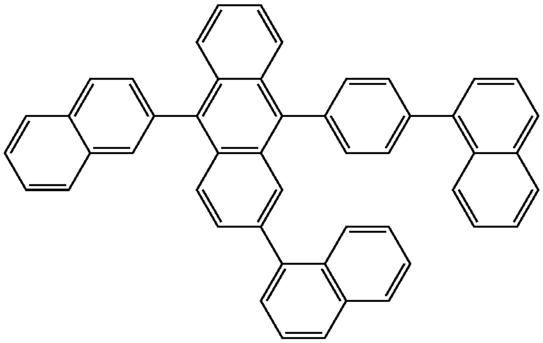
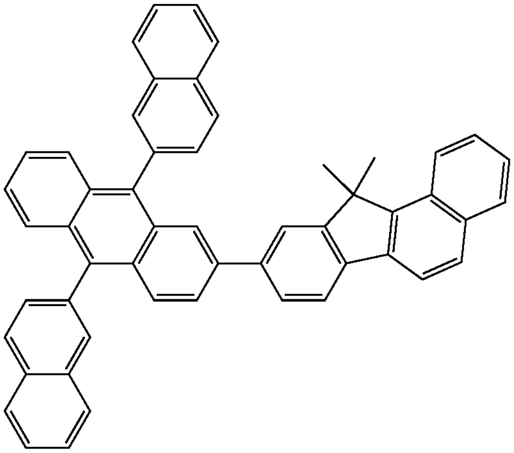
-continued
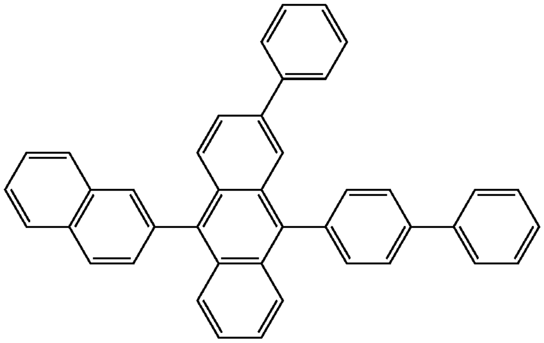
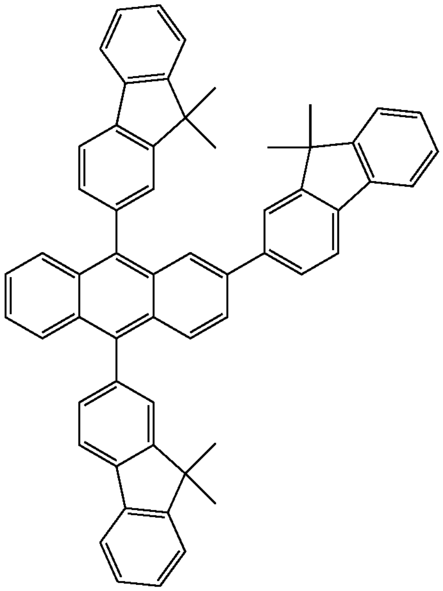
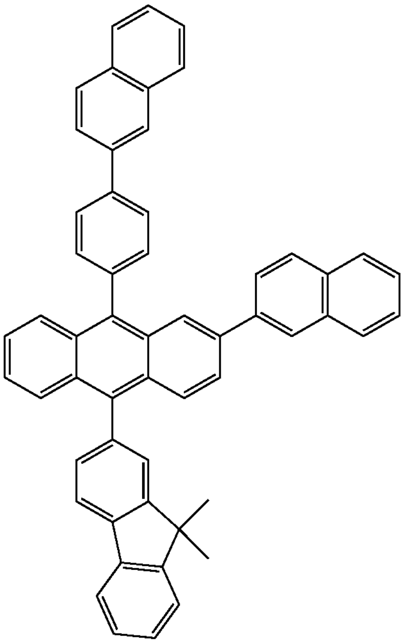

-continued

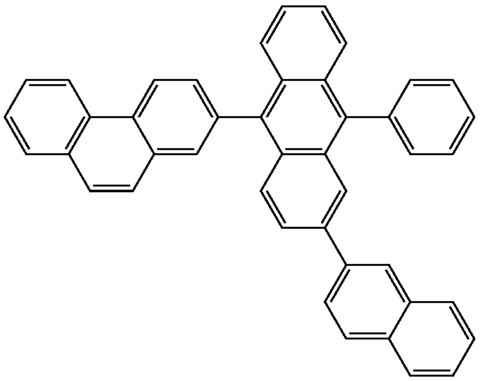 [SMILES: c1ccc(-c2c3ccccc3c(-c3ccc4c(ccc5ccccc54)c3)c3ccc(-c4ccc5ccccc5c4)cc23)cc1]

In other embodiments, an anthracene-based compound represented by Formula 401 below may be used as the host:

<Formula 401>

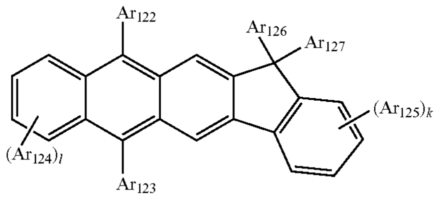

The detailed descriptions of $Ar_{122}$ to $Ar_{125}$ of Formula 401 are referred to in the above descriptions of $Ar_{113}$ in Formula 400.

In Formula 401, $Ar_{126}$ and $Ar_{127}$ may be each independently a $C_1$-$C_{10}$ alkyl group (for example, one of a methyl group, an ethyl group and a propyl group).

In Formula 401 above, k and l may be each independently an integer of 0 to 4. For example, k and l may be 0, 1, or 2.

For example, the anthracene-based compound represented by Formula 401 may be one of the compounds below, but it is not limited thereto:

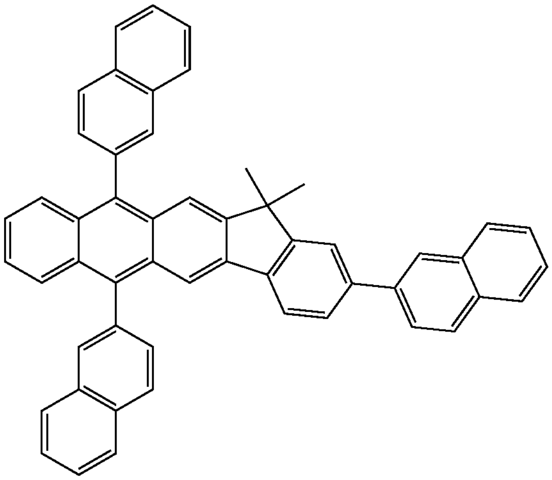

-continued

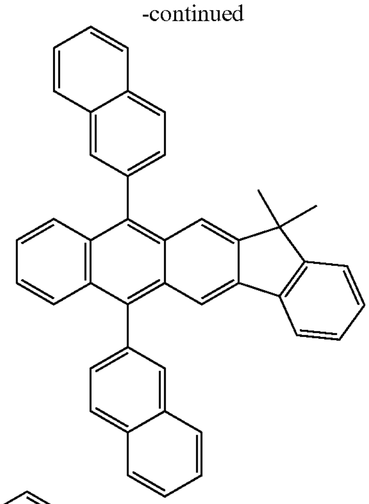

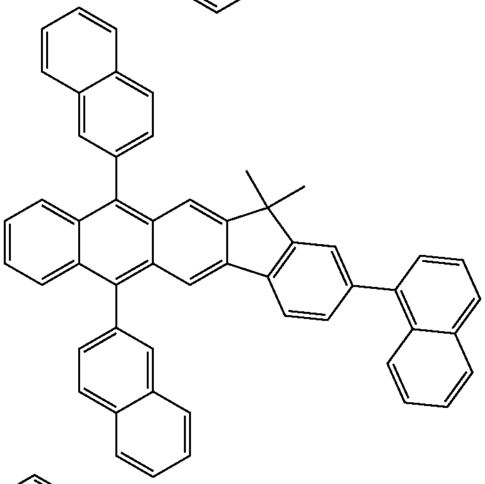

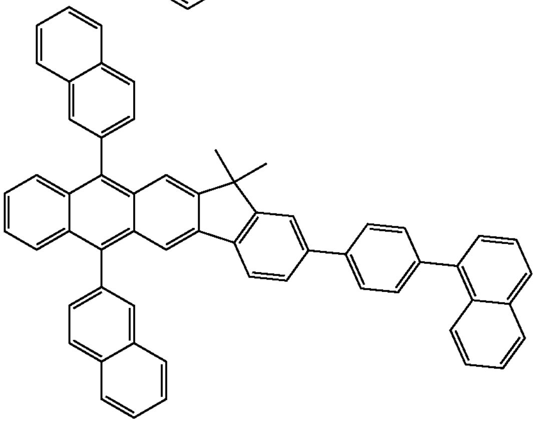
.

When the organic light-emitting device is a full color organic light-emitting device, the emission layer may be patterned into a red emission layer, a green emission layer, and a blue emission layer.

Even when the organic light-emitting device is a (laminated) white organic light-emitting device (having a LGD TV structure and a white organic light-emitting device structure), the compounds of Formulae 1 and 2 may be used to manufacture the organic light-emitting device, and a detailed description regarding the white organic light-emitting device is omitted, as it is well known in the art.

Also, at least one of the red emission layer, the green emission layer, and the blue emission layer may include one of a compound of Formula 2 according to an embodiment of the present inventive concept and the dopants below (ppy=phenylpyridine).

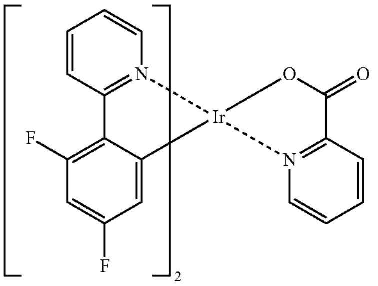
F$_2$Irpic
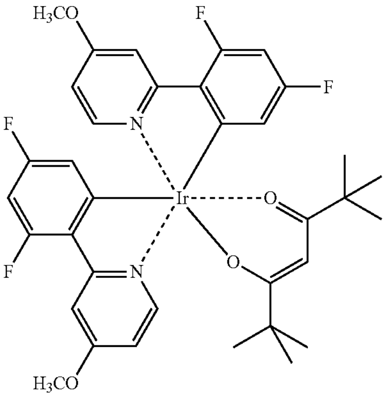
(F$_2$ppy)$_2$Ir(tmd)
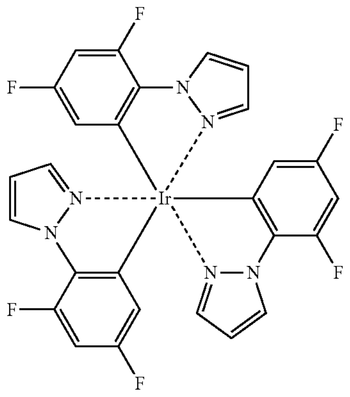
Ir(dfppz)$_3$
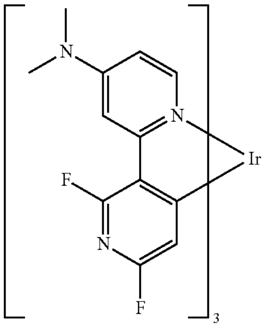
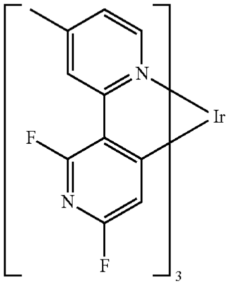
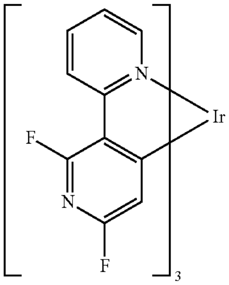
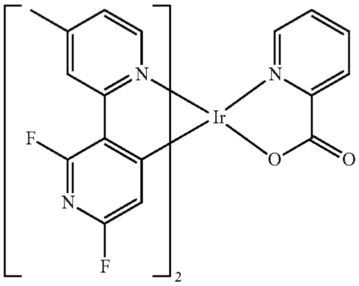
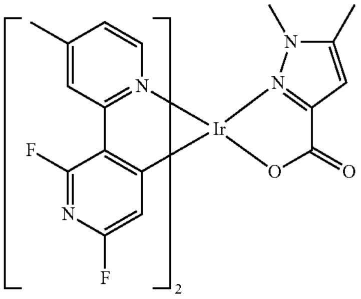
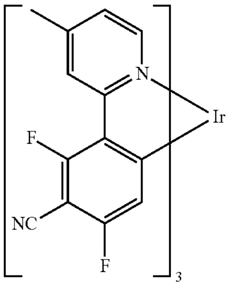
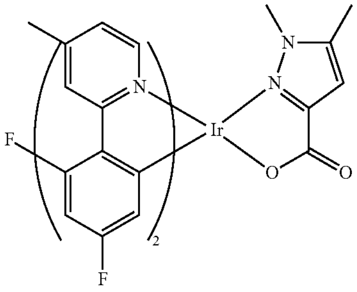
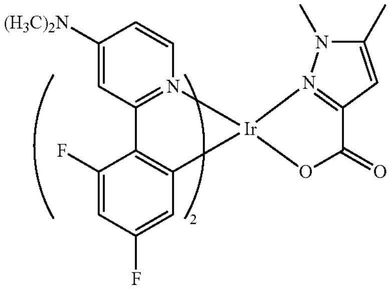
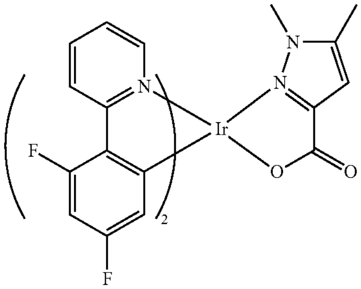
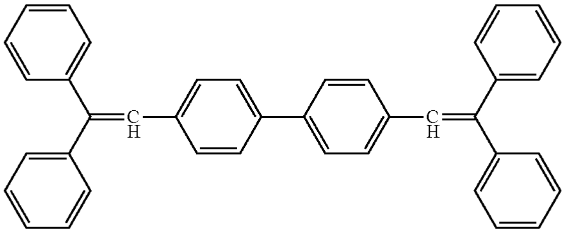
DPVBi -continued
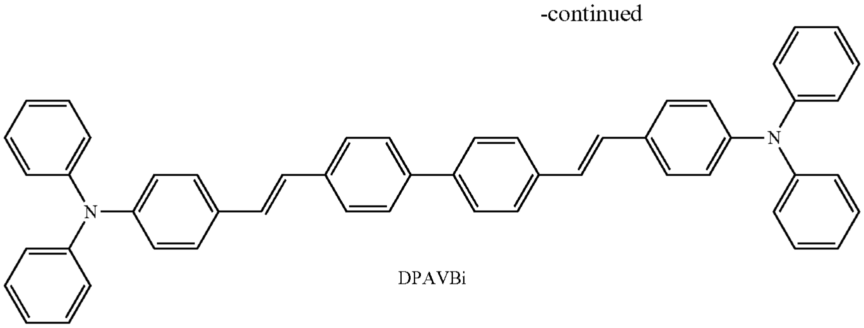
DPAVBi
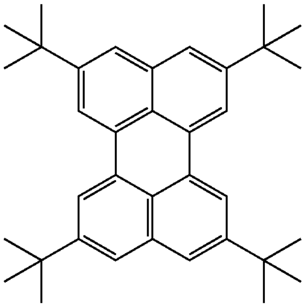
TBPe .
Non-limiting examples of the red dopant may be compounds represented by the following formulae.
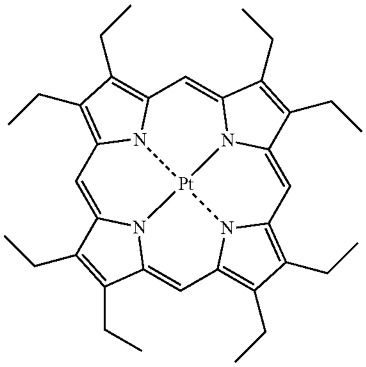
PtOEP
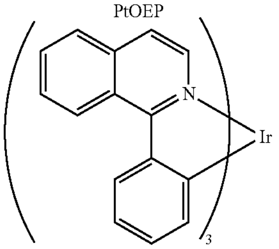
Ir(piq)$_3$
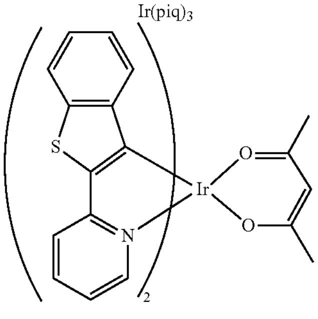
Btp$_2$Ir(acac)
-continued
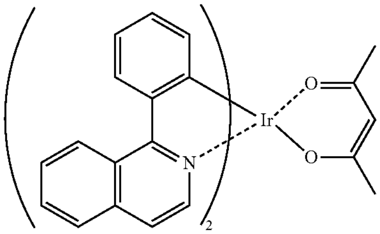
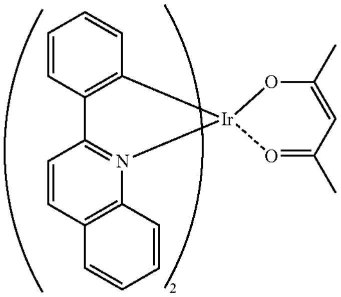
Ir(pq)$_2$(acac)
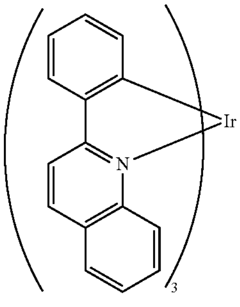
Ir(2-phq)$_3$
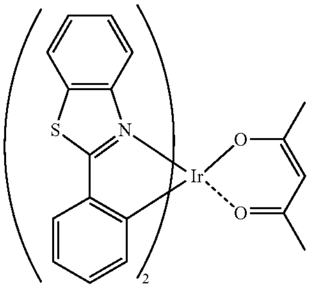
Ir(BT)$_2$(acac)

-continued
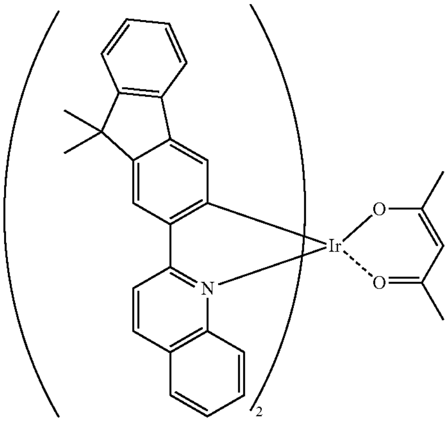
Ir(flq)2(acac)
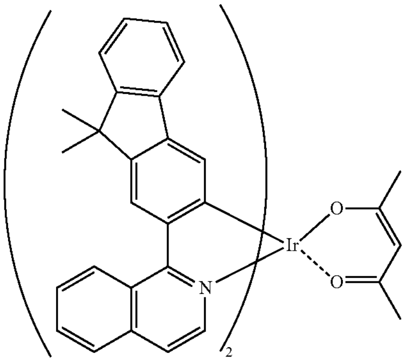
Ir(fliq)2(acac)
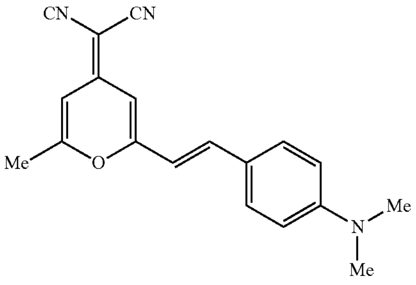
DCM
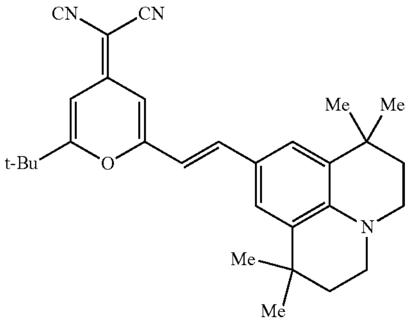
DCJTB
Non-limiting examples of the green dopant may be compounds represented by the following formulae.
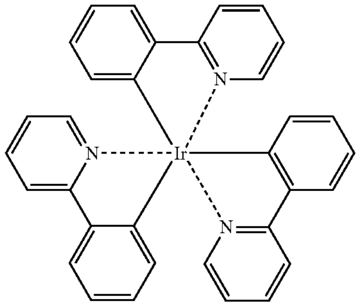
Ir(ppy)3
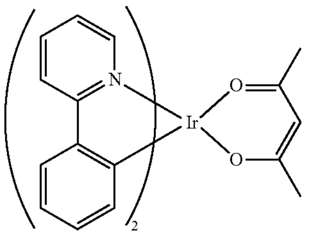
Ir(ppy)2(acac)
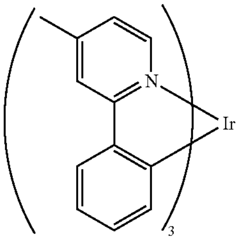
Ir(mpyp)3
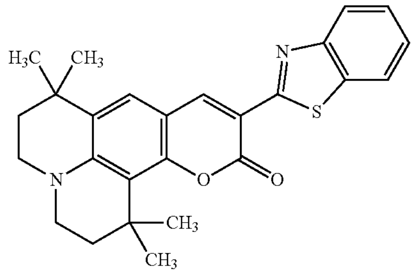
C545T
Also, a dopant that may be included in the emission layer may be a Pd-complex or Pt-complex as described below, but it is not limited thereto.
D1
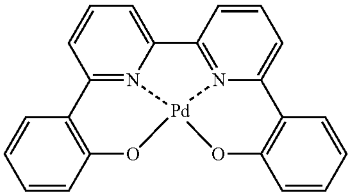
D2
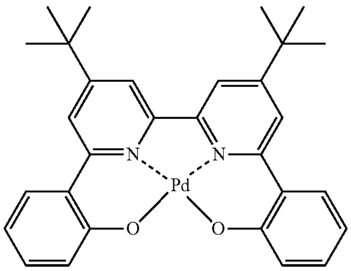

-continued
D3
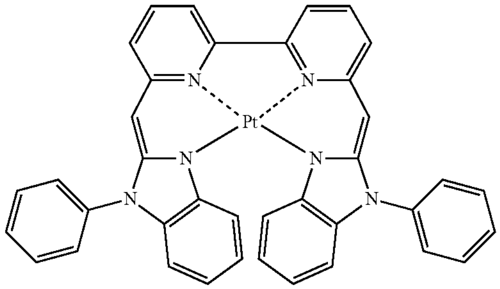
D4
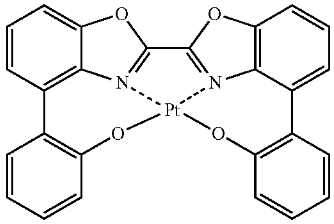
D5
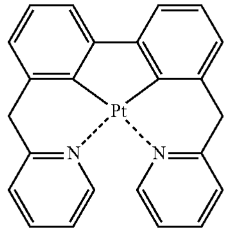
D6
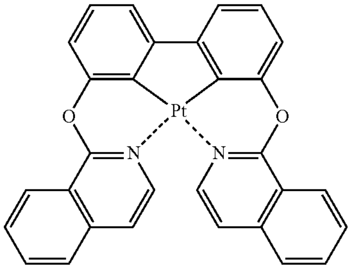
D7
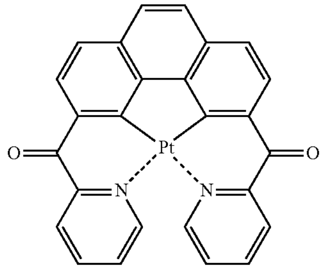
D8
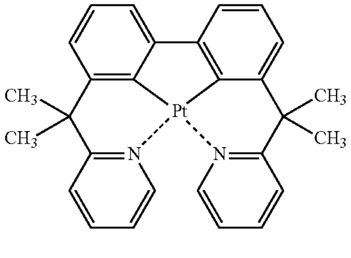
-continued
D9
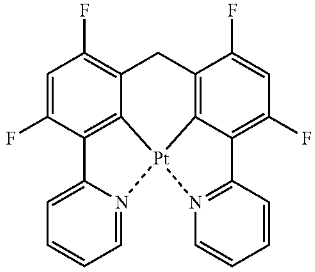
D10
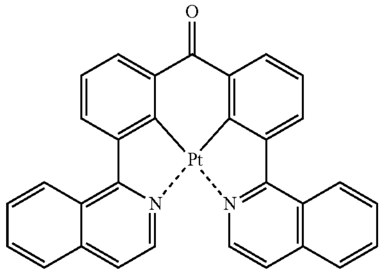
D11
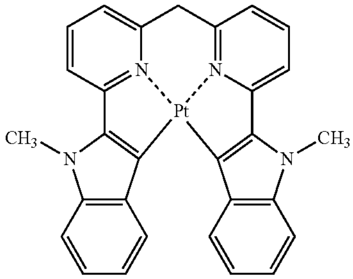
D12
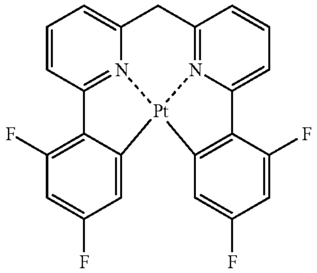
D13
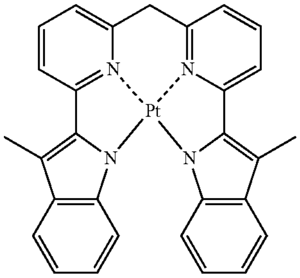

-continued
D14
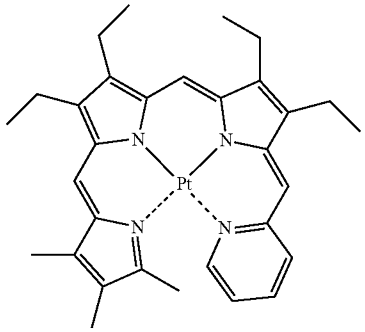
D15
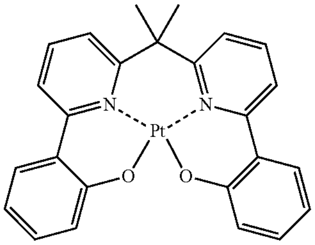
D16
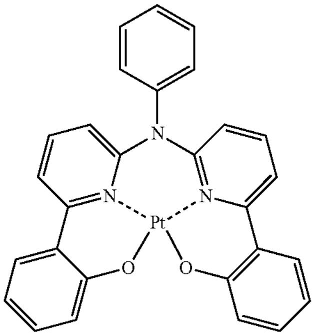
D17
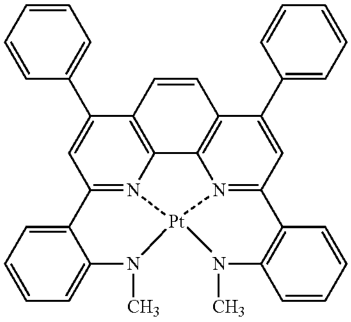
D18
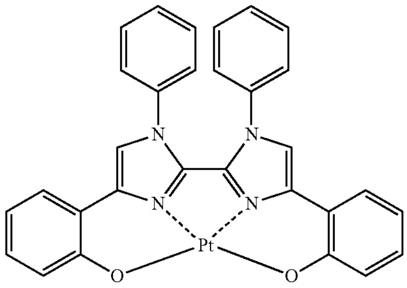
-continued
D19
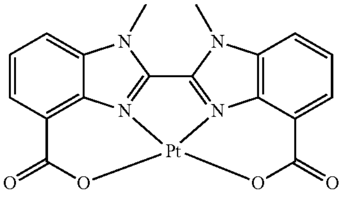
D20
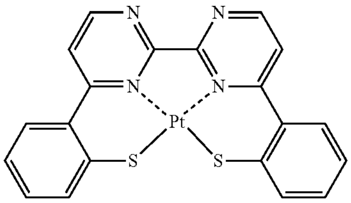
D21
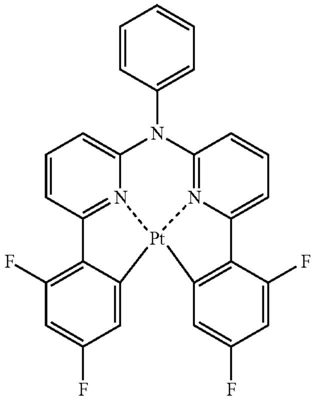
D22
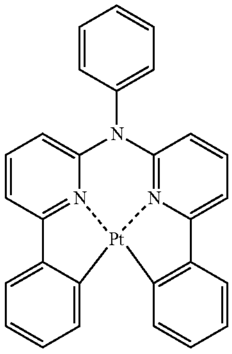
D23
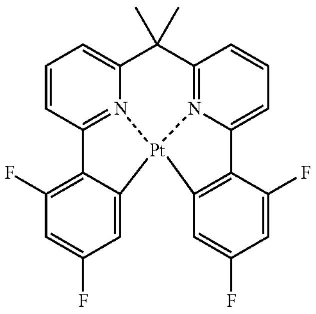

-continued
D24
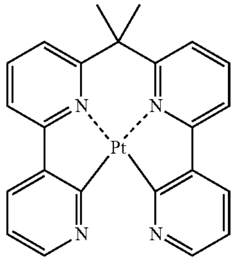
D25
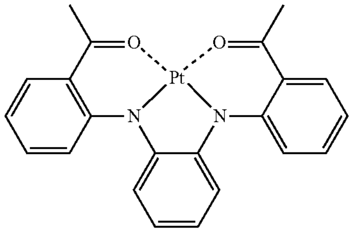
D26
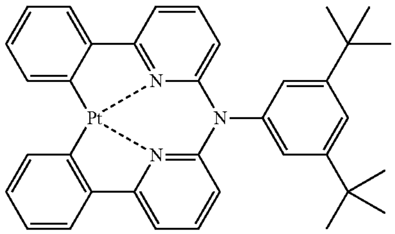
D27
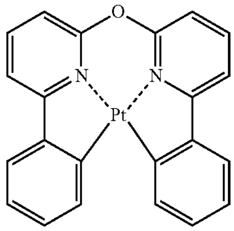
D28
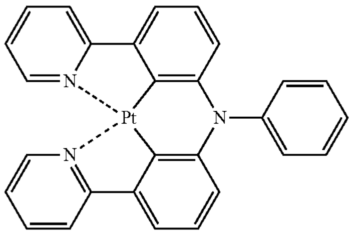
D29
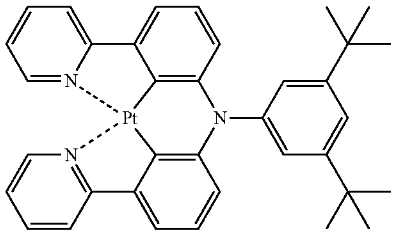
-continued
D30
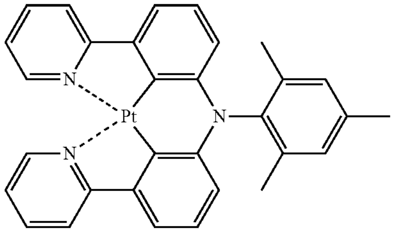
D31
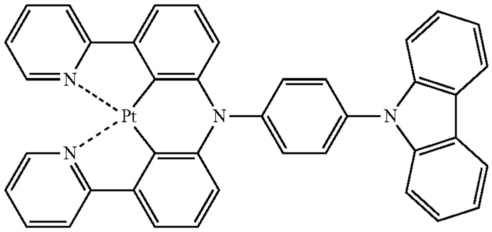
D32
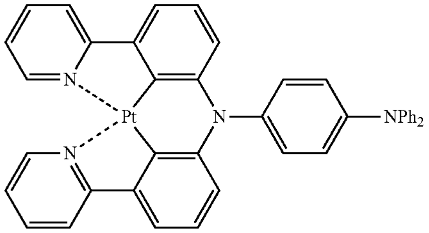
D33
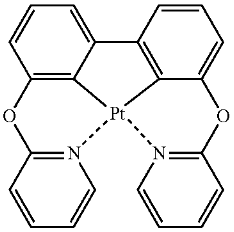
D34
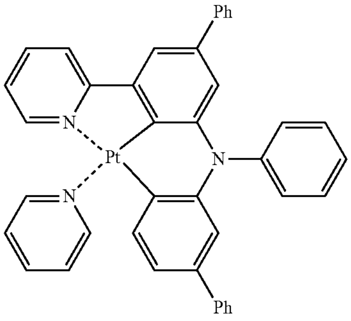
D35
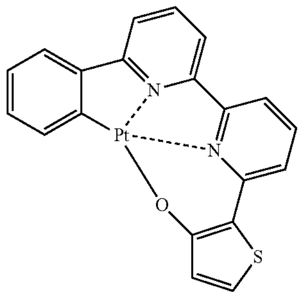

-continued
D36
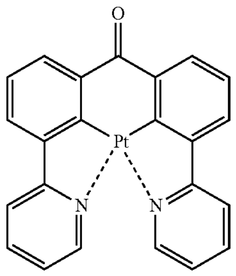
D37
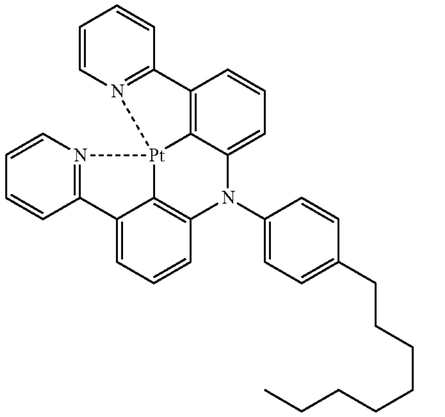
D38
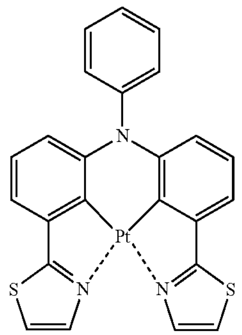
D39
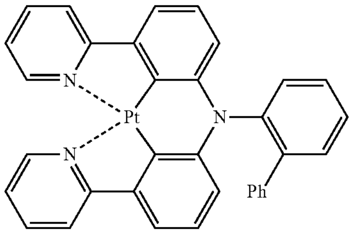
D40
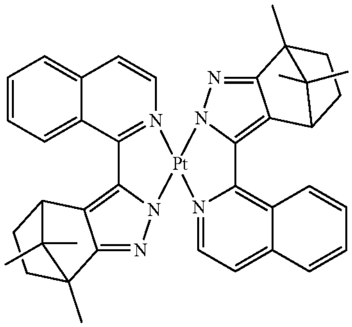
-continued
D41
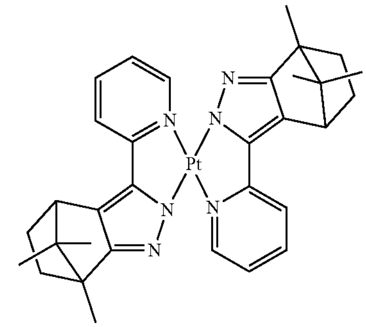
D42
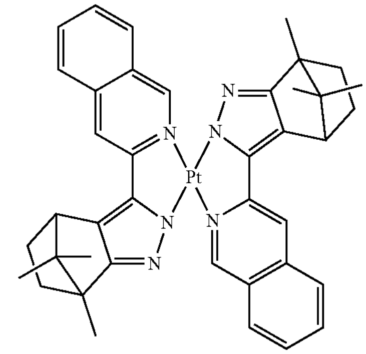
D43
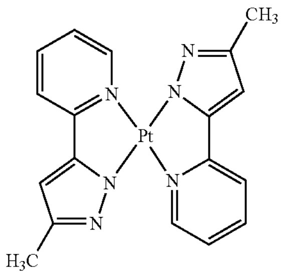
D44
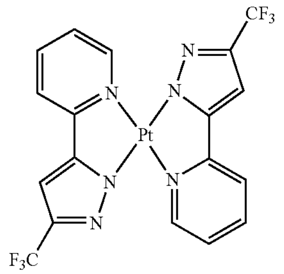
D45
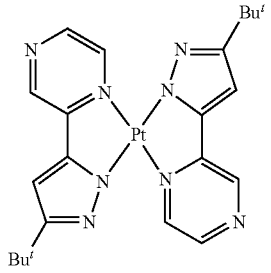

-continued
D46
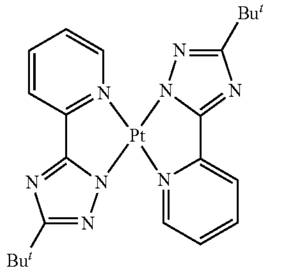
D47
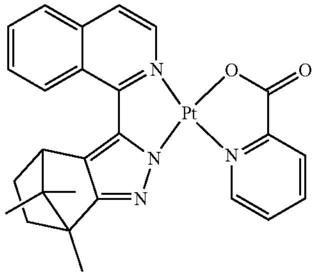
D48
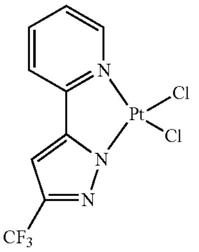
D49
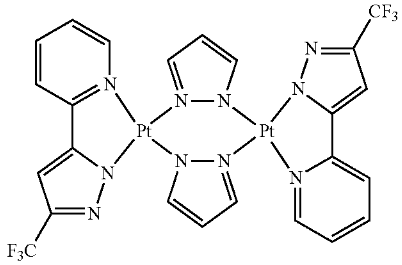
D50
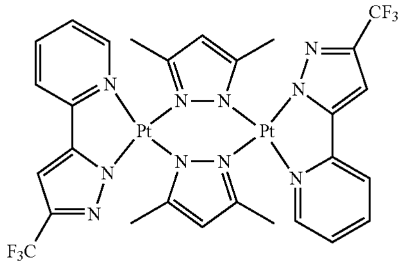
Non-limiting examples of the dopant that may be included in the emission layer may be Os-complexes described below.
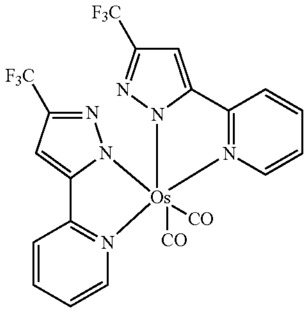
Os(fppz)$_2$(CO)$_2$
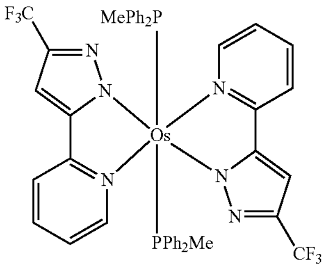
Os(fppz)$_2$(PPh$_2$Me)$_2$
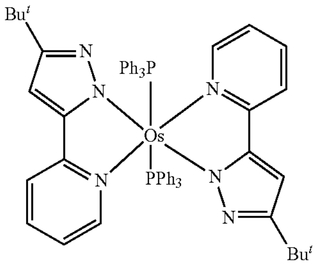
Os(bppz)$_2$(PPh$_3$)$_2$
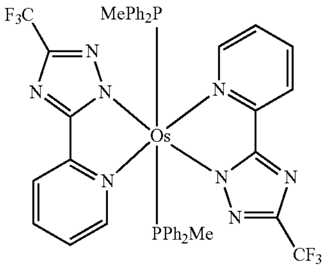
Os(fptz)$_2$(PPh$_2$Me)$_2$
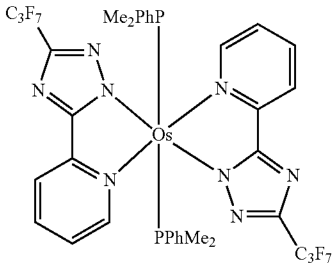
Os(hptz)$_2$(PPhMe$_2$)$_2$ When the emission layer includes both a host and a dopant, the amount of the dopant may be from about 0.01 parts by weight to about 15 parts by weight based on 100 parts by weight of the host. However, the amount of the dopant is not limited to this range.

The thickness of the emission layer may be from about 100 Å to about 1000 Å, and, in some embodiments, may be from about 200 Å to about 600 Å. When the thickness of the emission layer is within these ranges, the emission layer may have a good light-emitting ability without imparting a substantial increase in driving voltage to the corresponding OLED.

Then, an electron transport layer may be formed by any of a variety of methods, for example, one of vacuum deposition, spin coating and casting. When the electron transport layer is formed by using vacuum deposition or spin coating, the deposition and coating conditions may be similar to those for the formation of the hole injection layer, though the deposition and coating conditions may vary according to a compound that is used to form the electron transport layer. As the electron transport material, any electron transporting material that can stably transport electrons injected from an electron injecting electrode (cathode) may be used as a material for the electron transport layer. Non-limiting examples of useful electron transport materials may include quinoline derivatives such as tris(8-quinolinorate)aluminum (Alq3), 3-(biphenyl-4-yl)-4-phenyl-5-(4-t-butylphenyl)-1,2,4-triazole (TAZ), bis(2-methyl-8-quinolinato-N1,O8)-(1,1'-biphenyl-4-olato)aluminum (BAlq), beryllium bis(benzoquinolin-10-olate) (Bebq2), 9,10-di(naphthalene-2-yl)anthracene (ADN), Compound 201, and Compound 202.

TAZ

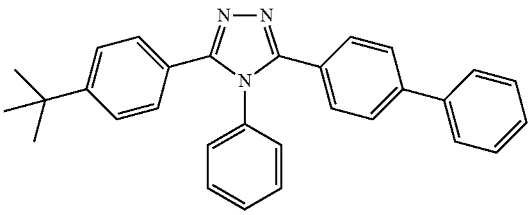

BAlq

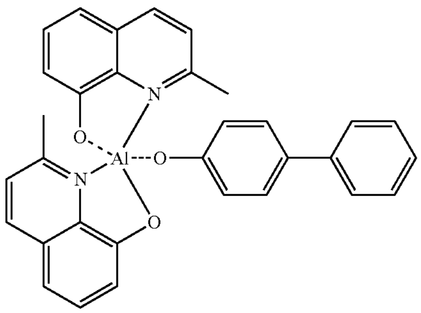

-continued

<Compound 201>

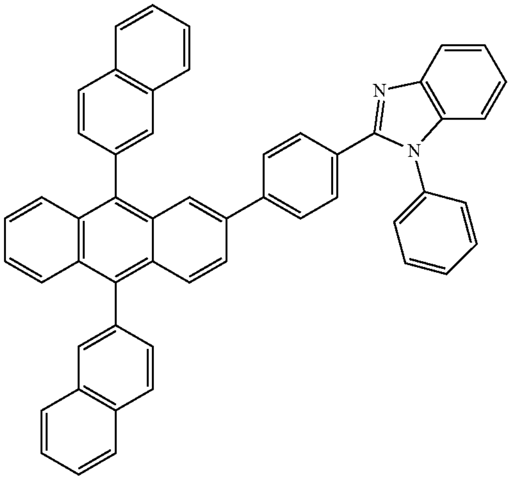

<Compound 202>

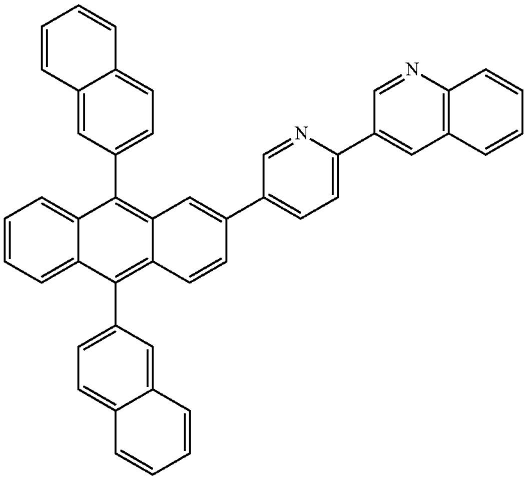

BCP

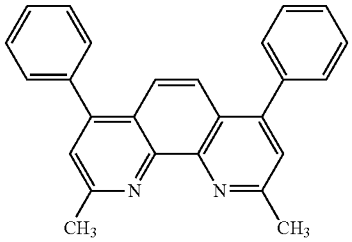

.

A thickness of the electron transport layer may be from about 100 Å to about 1,000 Å, and, in some embodiments, may be from about 150 Å to about 500 Å. When the thickness of the electron transport layer is within these ranges, the electron transport layer may have a satisfactory electron transporting ability without imparting a substantial increase in driving voltage to the corresponding OLED.

In some embodiments, the electron transport layer may further include a metal-containing material in addition to an electron-transporting organic compound.

The metal-containing material may include a Li complex. Non-limiting examples of the Li complex are lithium quinolate (LiQ) and Compound 203 below:

<Compound 203>

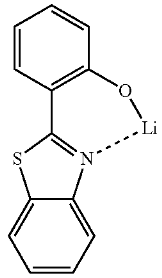

Then, an electron injection layer, which facilitates injection of electrons from the negative electrode, may be laminated on the electron transport layer. Any suitable electron injecting material may be used to form the electron injection layer.

Non-limiting examples of electron injecting materials useful for forming the electron injection layer are LiF, NaCl, CsF, $Li_2O$ and BaO, which are known in the art. The deposition and coating conditions for forming the electron injection layer may be similar to those for the formation of the hole injection layer, though the deposition and coating conditions may vary according to the compound that is used to form the electron injection layer.

A thickness of the electron injection layer may be from about 1 Å to about 100 Å, and, in some embodiments, may be from about 3 Å to about 90 Å. When the thickness of the electron injection layer is within these ranges, the electron injection layer may have satisfactory electron injection ability without imparting a substantial increase in driving voltage to the corresponding OLED.

A second electrode is provided on the organic layer. The second electrode may be a cathode that is an electron injection electrode. A material for forming the second electrode may be one of a metal, an alloy, an electro-conductive compound that has a low work function and a mixture thereof. In this regard, one of lithium (Li), magnesium (Mg), aluminum (Al), aluminum-lithium (Al—Li), calcium (Ca), magnesium-indium (Mg—In), magnesium-silver (Mg—Ag) and the like may be formed into a thin film to obtain a transmission electrode. In some embodiments, various changes are possible for manufacturing a top-emission light-emitting device, such as forming the transmission electrode of indium tin oxide (ITO) or indium zinc oxide (IZO).

Although the organic light-emitting device was described with reference to FIG. 1, the present inventive concept is not limited thereto.

Also, when a phosphorescent dopant is used in the emission layer, a hole blocking layer may be formed between the electron transport layer and the emission layer or between the E-functional layer and the emission layer by using one of vacuum deposition, spin coating, casting, LB deposition and the like, to prevent diffusion of triplet excitons or holes into the electron transport layer. When the hole blocking layer is formed by using vacuum deposition or spin coating, the conditions for deposition and coating may be similar to those for the formation of the hole injection layer, although the conditions for deposition and coating may vary according to the compound that is used to form the hole blocking layer. Hole blocking layer materials such as oxadiazole derivatives, triazole derivatives and phenanthroline derivatives may be used. For example, materials, such as bathocuproine (BCP), shown below, may be used as the hole blocking layer material.

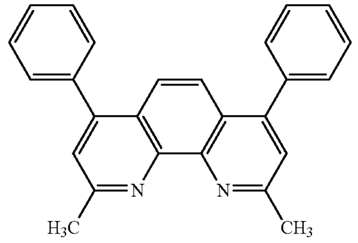

BCP

A thickness of the hole blocking layer may be from about 20 Å to about 1000 Å, and, in some embodiments, may be from about 30 Å to about 300 Å. When the thickness of the hole blocking layer is within these ranges, the hole blocking layer may have improved hole blocking ability without imparting a substantial increase in driving voltage to the corresponding OLED.

The organic light-emitting device according to the present inventive concept may be included in various flat display devices, for example, a passive matrix organic light-emitting display device and an active matrix organic light-emitting display device. More particularly, when the organic light-emitting device is included in the active matrix organic light-emitting display device, the first electrode disposed on the substrate may be electrically connected to a source electrode or a drain electrode of the thin film transistor as a pixel electrode. Also, the organic light-emitting device may be included in a flat display device capable of displaying on screens on both sides.

Also, the organic light-emitting device according to an embodiment of the present inventive concept may be formed through a deposition method by using the compounds according to an embodiment of the present inventive concept, or may be formed through a wet method of coating the compounds according to an embodiment of the present inventive concept prepared in a solution.

Hereinafter, the organic light-emitting device according to an embodiment of the present inventive concept will be described in greater detail with reference to the following Synthesis Examples and Examples. However, these examples are for illustrative purposes only and are not intended to limit the scope of the present inventive concept.

EXAMPLE

Hereinafter, preferred embodiments of the present inventive concept will be exemplified by Synthesis Examples for the preparation of Compounds 1, 22, 31, and 43 of Formula 1 and compound 40 of Formula 2; however, the present inventive concept is not limited by the Examples.

Synthesis Example 1

Synthesis of Compound 1 of Formula 1

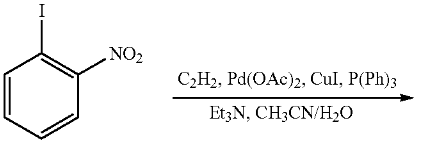

-continued

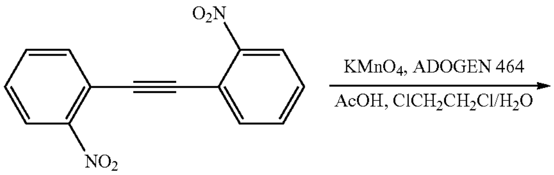

I-1

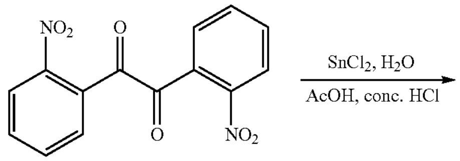

I-2

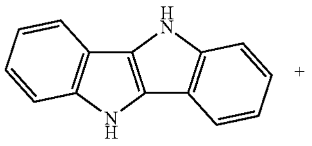

I-3

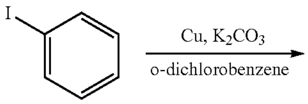

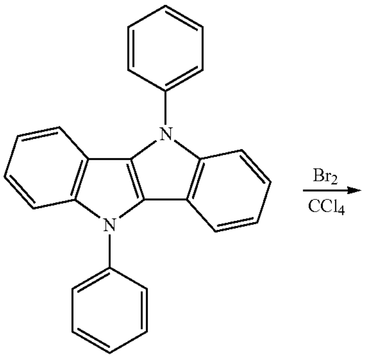

I-4

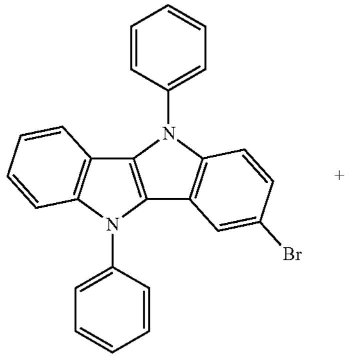

I-5

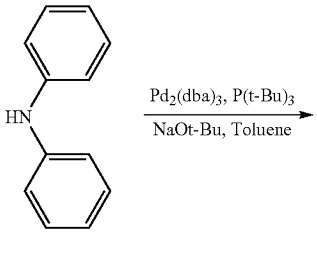

-continued

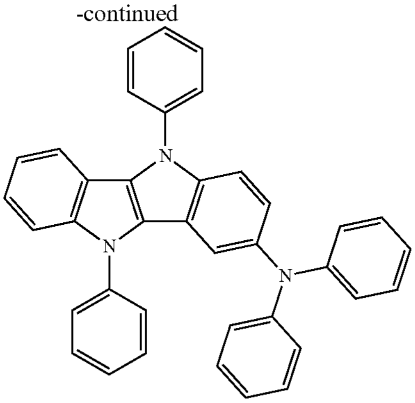

1

Synthesis of Intermediate I-1

Quantities of 225 mg (1.00 mmol) of $Pd(OAc)_2$, 263 mg (1.00 mmol) of triphenylphosphine, and 191 mg (1.00 mmol) of CuI were dissolved in 30 ml of acetonitrile and 10 mL of distilled water to prepare a mixture, and the mixture was agitated for 20 minutes at room temperature in a reaction chamber. Quantities of 5 g (20.08 mmol) of 1-iodo-2-nitrobenzene and 15 ml of triethylamine were dissolved in 50 mL of acetonitrile and were added to the mixture. A quantity of 1500 $cm^3$ of acetylene was injected into the reaction chamber, and the reaction mixture was agitated for 10 minutes at room temperature. Then, the mixture was extracted by using 500 ml of methylene chloride, and the methylene chloride extracts were washed with distilled water. After drying the methylene chloride extracts using magnesium sulfate, the extracts were filtered, and the solvent was evaporated. Thereafter, 4.6 g of intermediate I-1 (2,2'-dinitrotolane) (yield 85%) was obtained through column chromatography.

Synthesis of Intermediate I-2

A quantity of 4.6 g (17.15 mmol) of intermediate I-1 was dissolved in 110 ml of ethylene dichloride to prepare a mixture, and, then, 13.55 g (85.75 mmol) of potassium permanganate was dissolved in 90 mL of distilled water and added to the mixture. Quantities of 6 ml of ADOGEN 464 and 7 ml of acetic acid were added to the mixture and the mixture was refluxed for 3 hours at a temperature of 90° C. Then, 6 g of sodium bisulfate was added to the mixture. Thereafter, an organic layer was separated, then dried with magnesium sulfate, then filtered, and the solvent was evaporated. Thereafter, 1.85 g of intermediate I-2 (2,2'-dinitrobenzyl) (yield 48%) was obtained through column chromatography.

Synthesis of Intermediate I-3

A quantity of 1.6 g (1 eq, 5.33 mmol) of intermediate I-2 was dissolved in 60 mL of acetic acid to prepare a mixture, and 12 g (53.29 mmol) of stannous chloride dihydrate and 30 ml of 1 M HCl were added to the mixture. The mixture was refluxed and agitated for 5 hours at a temperature of 80° C., then filtered to collect a yellow precipitate. The yellow precipitate was washed with 30 ml acetic acid, 30 ml of 1 M HCl, and 30 ml of ethanol. After drying the yellow solid, 340 mg of intermediate I-3 (5,10-dihydroindolo[3,2-b]indole) (yield 31%) was obtained.

Synthesis of Intermediate I-4

After 340 mg (1.65 mmol) of intermediate I-3 was dissolved in 15 ml of THF, 158 mg (6.59 mmol) of NaH dissolved in 10 ml of THF was added thereto to prepare a mixture. After agitating the mixture for 10 minutes at room temperature, 978 mg (495 mmol) of phenyl iodide was added to the mixture, and the resulting mixture was agitated for 12 hours at room temperature. Then, 20 ml of distilled water was added to the mixture, and the mixture was extracted using methylene chloride. After drying the extracts using magnesium sulfate, the extracts were filtered, and the solvent was evaporated. Thereafter, 530 mg of intermediate I-4 (5,10-diphenyl-5,10-dihydroindolo[3,2-b]-indole) (yield 90%) was obtained through column chromatography.

Synthesis of Intermediate I-5

After dissolving 590 mg (1.65 mmol) of intermediate I-4 in 6 ml of pyridine, 1.64 ml (1.64 mmol) of bromine diluted in 34 ml of $CCl_4$ was added thereto to prepare a mixture. After agitating the mixture for 1 hour at room temperature, 3 ml of 1 M HCl was added to the mixture, and the mixture was extracted using 20 ml of methylene chloride. After drying the extracts using magnesium sulfate, the extracts were filtered, and the solvent was evaporated. Thereafter, 350 mg of intermediate I-5 (3-bromo-5,10-diphenyl-5,10-dihydroindolo[3,2-b]-indole) (yield 48%) was obtained through column chromatography.

Synthesis of Compound 1 of Formula 1

Quantities of 20.9 mg (0.023 mmol) of $Pd_2(dba)_3$ and 9.25 mg (0.046 mmol) of t-$Bu_3P$ were dissolved in 10 ml of toluene and agitated for 10 minutes at room temperature to prepare a mixture. Quantities of 1 g (2.287 mmol) of 3-bromo-5,10-dihexyl-5,10-dihydroindolo[3,2-b]-indole, 386 mg (2.287 mmol) of diphenylamine, and 132 mg (1.372 mmol) of t-BuONa were added to the mixture, and the mixture was refluxed and agitated for 12 hours at a temperature of 80° C. Then, 20 ml of cold distilled water was added to the mixture, and the resulting mixture was extracted using ethyl acetate. After drying the extracts using magnesium sulfate, the extracts were filtered, and the solvent was evaporated. Thereafter, 520 mg of compound 1 (3-diphenylamino-5,10-diphenyl-5,10-dihydroindolo[3,2-b]-indole) (yield 43%) was obtained through column chromatography.

$^1$H NMR (300 MHz, $CDCl_3$), d (ppm): 7.90-7.82 (1H, m), 7.73-7.67 (2H, m), 7.66-7.58 (4H, m), 7.50-7.40 (5H, m), 7.31-7.20 (7H, m), 7.19-7.13 (1H, m), 7.13-7.04 (5H, m), 6.98-6.90 (2H, m) EI-MS, m/e, calcd for $C_{38}H_{27}N_3$ 525.22. found 525.28.

Synthesis Example 2

Synthesis of Compound 22 of Formula 1

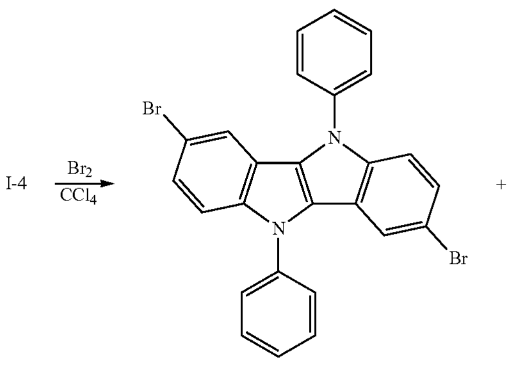

I-7

-continued

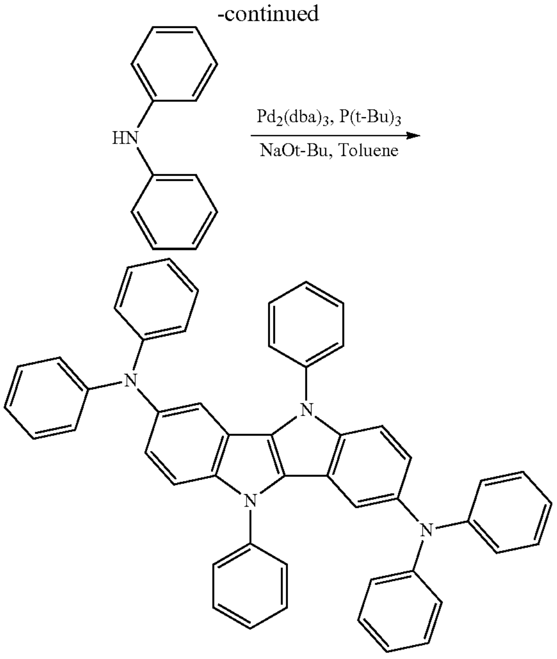

22

Synthesis of Intermediate I-7

After dissolving 590 mg (1.65 mmol) of intermediate I-4 in 6 ml of pyridine, 3.29 ml (3.29 mmol) of bromine diluted in 60 ml of $CCl_4$ was added thereto to prepare a mixture. After agitating the mixture for 1 hour at room temperature, 3 ml of 1 M HCl was added to the mixture, and the mixture was extracted using 20 ml of methylene chloride. After drying the extracts using magnesium sulfate, the extracts were filtered, and the solvent was evaporated. Thereafter, 510 mg of intermediate I-7 (3,7-dibromo-5,10-diphenyl-5,10-dihydroindolo[3,2-b]-indole) (yield 60%) was obtained by using column chromatography.

Synthesis of Compound 22 of Formula 1

Quantities of 20.9 mg (0.023 mmol) of $Pd_2(dba)_3$ and 9.25 mg (0.046 mmol) of t-$Bu_3P$ were dissolved in 10 ml of toluene to prepare a mixture, and the mixture was agitated for 10 minutes at room temperature. Quantities of 1 g (2.287 mmol) of 3,7-dibromo-5,10-diphenyl-5,10-dihydroindolo[3,2-b]-indole, 773 mg (4.573 mmol) of diphenylamine, and 132 mg (1.372 mmol) t-BuONa were added to the mixture, and the mixture was refluxed and agitated for 12 hours at a temperature of 80° C. Then, 20 ml of cold distilled water was added to the mixture, and the resulting mixture was extracted using ethyl acetate. After drying the extracts using magnesium sulfate, the extracts were filtered, and the solvent was evaporated. Thereafter, 1.051 g of Compound 22 (3,7-di(diphenylamino)-5,10-diphenyl-5,10-dihydroindolo[3,2-b]-indole) (yield 66%) was obtained through column chromatography.

$^1$H NMR (300 MHz, $CDCl_3$), d (ppm): 7.70-7.65 (2H, d), 7.61-7.56 (4H, m), 7.50-7.41 (6H, m), 7.30-7.20 (10H, m), 7.14-7.06 (10H, m), 6.98-6.91 (4H, m).

EI-MS, m/e, calcd for $C_{50}H_{36}N_4$ 692.29. found 692.35.

Synthesis Example 3

Synthesis of Compound 31 of Formula 1

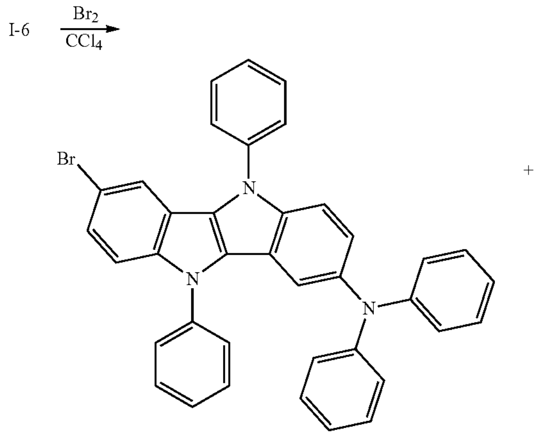

I-9

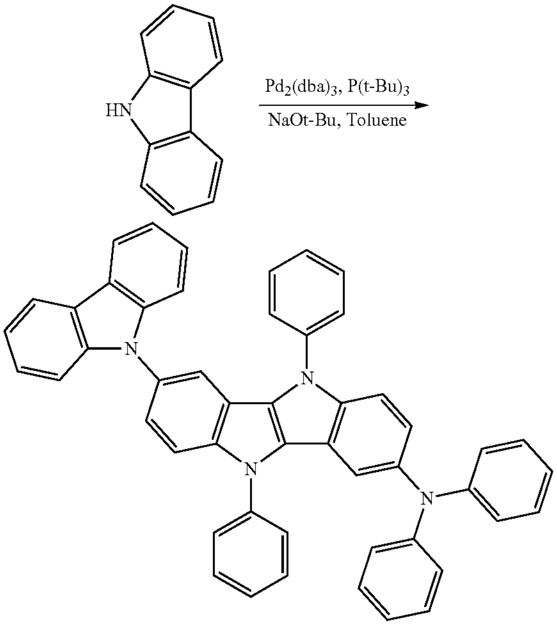

31

Synthesis of Intermediate I-9

After dissolving 500 mg (0.951 mmol) of intermediate I-6 in 5 ml of pyridine, 951 ml (0.951 mmol) of bromine dissolved in 29 ml of $CCl_4$ was added thereto to prepare a mixture. After agitating the mixture for 1 hour at room temperature, 3 ml of 1 M HCl was added to the mixture, and the mixture was extracted using 20 ml of methylene chloride. After drying the extracts using magnesium sulfate, the extracts were filtered, and the solvent was evaporated. Thereafter, 430 mg of intermediate I-9 (3-bromo-8-diphenylamino-5,10-diphenyl-5,10-dihydroindolo[3,2-b]-indole) (yield 75%) was obtained through column chromatography.

Synthesis of Compound 31 of Formula 1

Quantities of 15.1 mg (0.017 mmol) of $Pd_2(dba)_3$ and 6.70 mg (0.033 mmol) of $t-Bu_3P$ were dissolved in 10 ml of toluene to prepare a mixture, and the mixture was agitated for 10 minutes at room temperature. Quantities of 1 g (1.654 mmol) of 3-bromo-8-diphenylamino-5,10-diphenyl-5,10-dihydroindolo[3,2-b]-indole, 276 mg (1.654 mmol) of carbazole, and 95 mg (0.992 mmol) of t-BuONa were added to the mixture, and the mixture was refluxed and agitated for 12 hours at a temperature of 80° C. Then, 20 ml of cold distilled water was added thereto, and the mixture was extracted using ethyl acetate. After drying the extracts using magnesium sulfate, the extracts were filtered, and the solvent was evaporated. Thereafter, 821 mg of Compound 31 (3-carbazolyl-8-diphenylamino-5,10-diphenyl-5,10-dihydroindolo[3,2-b]-indole) (yield 72%) was obtained through column chromatography.

$^1$H NMR (300 MHz, $CDCl_3$), d (ppm): 7.93-7.86 (2H, m), 7.77-7.69 (3H, m), 7.67-7.60 (4H, m), 7.53-7.48 (1H, m), 7.48-7.41 (5H, m), 7.41-7.37 (2H, m), 7.30-7.20 (8H, m), 7.20-7.11 (6H, m), 7.10-7.05 (1H, m), 7.00-6.93 (2H, m) EI-MS, m/e, calcd for $C_{50}H_{34}N_4$ 690.28. found 690.23.

Synthesis Example 4

Synthesis of Compound 43 of Formula 1

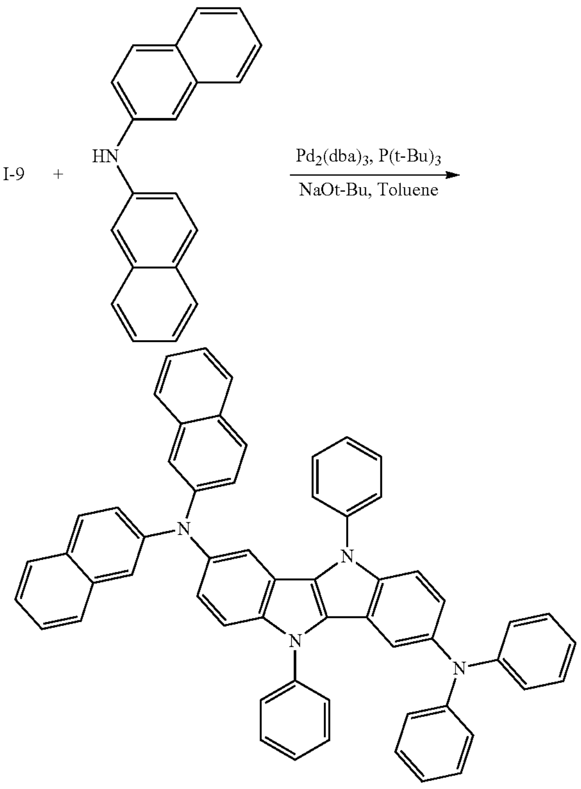

43

Synthesis of Compound 43 of Formula 1

After dissolving 15.1 mg (0.017 mmol) of $Pd_2(dba)_3$ and 6.70 mg (0.033 mmol) of $t-Bu_3P$ in 10 ml of toluene to prepare a mixture, the mixture was agitated for 10 minutes at room temperature. Quantities of 1 g (1.654 mmol) of 3-bromo-8-diphenylamino-5,10-diphenyl-5,10-dihydroindolo[3,2-b]-indole, 445 mg (1.654 mmol) of N,N-di(2-naphthyl)amine, and 95 mg (0.992 mmol) of t-BuONa were added to the mixture, and the mixture was refluxed and agitated for 12 hours at a temperature of 80° C. Then, 20 ml of cold distilled water was added to the mixture, and the mixture was extracted using ethyl acetate. After drying the extracts using magnesium sulfate, the extracts were filtered, and the solvent was evaporated. Thereafter, 756 mg of compound 43 (N3,N3-di(naphthalen-2-yl)-N8,N8,5,10-tetraphenyl-5,10-dihydroindolo[3,2-b]indole-3,8-diamine) (yield 58%) was obtained through column chromatography.

$^1$H NMR (300 MHz, $CDCl_3$), d (ppm): 7.83-7.77 (2H, m), 7.75-7.67 (4H, m), 7.65-7.56 (6H, m), 7.52-7.47 (3H, m), 7.47-7.44 (1H, m), 7.43-7.32 (10H, m), 7.27-7.20 (6H, m), 7.15-7.05 (6H, m), 6.98-6.91 (2H, m) EI-MS, m/e, calcd for $C_{58}H_{40}N_4$ 792.33. found 792.35.

Synthesis Example 5

Synthesis of Compound 94 of Formula 2

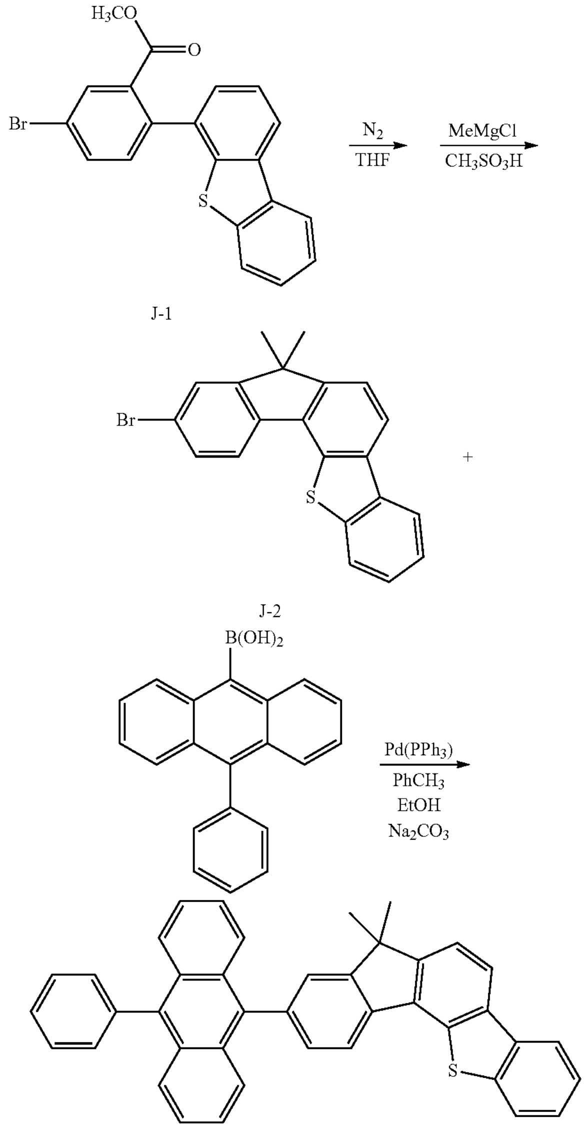

94

Synthesis of Intermediate J-1

Quantities of 3 g (1 eq, 8.80 mmol) of methyl 5-bromo-2-iodobenzoate, 2.21 g (1.1 eq, 9.68 mmol) of dibenzo[b,d]thiophen-4-ylboronic acid, and 410 mg (0.04 eq, 0.35 mmol) of tetrakis(triphenylphosphine)palladium(0) were added to a reaction chamber and vacuum dried, and the reaction chamber was filled with nitrogen gas. A quantity of 70 ml of toluene was added to the reaction chamber to dissolve the compounds, 30 ml of ethanol and 13 ml (3 eq, 26.4 mmol) of 2.0 M sodium carbonate aqueous solution were added to the reaction chamber to prepare a mixture, and the mixture was refluxed and agitated for 3 hours at a temperature of 120° C. Then, the mixture was washed with distilled water, and an organic layer was extracted using ethyl acetate. After drying the extracts using magnesium sulfate, the extracts were filtered, and the solvent was evaporated. Thereafter, 3.5 g of intermediate J-1 (methyl 5-bromo-2-(dibenzo[b,d]thiophen-4-yl)benzoate) (yield=75%) was obtained through column chromatography.

$^1$H-NMR: 8.18 (m, 3H), 7.76 (t, 2H), 7.53 (t, 1H), 7.45 (m, 2H), 7.38 (d, 1H), 7.27 (d, 1H), 3.55 (s, 3H). APCI-MS (m/z): 397 [$M^+$].

Synthesis of Intermediate J-2

A quantity of 6 g (1 eq, 15.1 mmol) of intermediate J-2 was added to a reaction chamber and vacuum dried, and the reaction chamber was filled with nitrogen gas. A quantity of 120 ml of THF was added to the reaction chamber, and 12.5 ml (2.5 eq, 37.7 mmol) of methylmagnesium chloride (3.0 M) was slowly added dropwise to the reaction chamber to prepare a reaction solution. The reaction solution was extracted using ethyl acetate to prepare a reaction product, the reaction product was added to a flask, the reaction product was dissolved by using MC, and $MeSO_3H$ (Methanesulfonic acid) was slowly added dropwise thereto. Then, the reaction product was extracted by using dichloromethane, and 4 g of intermediate J-2 (9-bromo-7,7-dimethyl-7H-benzo[b]fluoreno[3,4-d]thiophene) (yield=70%) was obtained through column chromatography.

$^1$H-NMR: 8.22 (d, 1H), 8.19 (d, 1H), 7.96 (d, 1H), 7.82 (d, 1H), 7.64 (t, 2H), 7.56 (d, 1H), 7.51 (m, 2H), 1.57 (s, 6H). APCI-MS (m/z): 379 [$M^+$].

Synthesis of Compound 94

Quantities of 4 g (1 eq, 10.5 mmol) of intermediate J-2 and 3.23 g (1.03 eq, 10.86 mmol) of 9-phenylanthracen-10-ylboronic acid, and 485 mg (0.04 eq, 0.42 mmol) tetrakis(triphenylphosphine)palladium(0) were added and vacuum dried in a reaction chamber, and the reaction chamber was filled with nitrogen gas. A quantity of 80 ml of toluene was added to the reaction chamber to dissolve the compounds, 40 ml of ethanol and 16 ml (3 eq, 31.5 mmol) of 2.0 M sodium carbonate aqueous solution was added to the reaction chamber to prepare a mixture, and the mixture was refluxed and agitated for 3 hours at a temperature of 120° C. Then, the mixture was washed with distilled water, and an organic layer was extracted using ethyl acetate. The extracts were dried with magnesium sulfate and filtered through Celite, and 4 g of compound 40 (7,7-dimethyl-9-(10-phenylanthracen-9-yl)-7H-benzo[d]fluoreno[4,3-b]thiophene) (yield=70%) were obtained through column chromatography.

$^1$H-NMR: 8.28 (d, 1H), 8.22 (t, 2H), 8.01 (d, 1H), 7.82 (d, 2H), 7.74 (t, 2H), 7.60 (m, 10H), 7.36 (m, 4H), 1.64 (s, 6H). APCI-MS (m/z): 553 [$M^+$].

Example 1

As an anode, a Corning 15 $\Omega/cm^2$ (1200 Å) ITO glass substrate was cut into a size of 50 mm×50 mm×0.7 mm, and the ITO glass substrate was ultrasonically washed using isopropyl alcohol and distilled water for 5 minutes, followed by irradiation of UV light and exposure to ozone for cleaning for about 30 minutes. The ITO glass substrate was then loaded onto a vacuum deposition device.

2-TNATA, a material known as a hole injecting material, was vacuum deposited on the substrate to form an hole injection layer in a thickness of 600 Å, and 4,4'-bis[N-(1-naphthyl)-N-phenyl amino]biphenyl (NPB), a material known as a hole transport compound, was vacuum deposited thereto to form a hole transport layer in a thickness of 300 Å.

By using compound 40 of Formula 2 as a fluorescent host and compound 1 of Formula 1 of the present inventive concept as a fluorescent dopant in a weight ratio of 95:5, an emission layer was formed in a thickness of 20 nm on the hole transport layer.

Thereafter, compound 201 was deposited in a thickness of 300 Å as an electron transport layer on the emission layer, LiF was deposited in a thickness of 10 Å as an electron injection layer on the electron transport layer, and Al was vacuum deposited in a thickness of 3000 Å (a negative electrode) to form a LiF/Al electrode, thereby manufacturing an organic light-emitting device.

The organic light-emitting device showed a driving voltage of 3.7 V, an emission brightness of 556 cd/m$^2$, and an emission efficiency of 5.56 cd/A at a current density of 10 mA/cm$^2$.

<Compound 201>

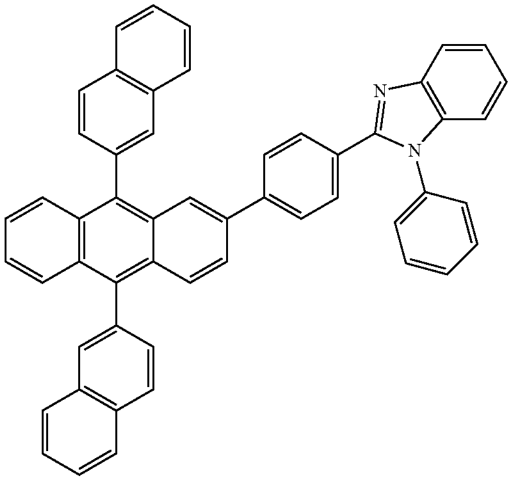

Example 2

An organic light-emitting device was manufactured in the same manner as in Example 1, except for using Compound 22 of Formula 1 instead of using compound 1 of Formula 1.

The organic light-emitting device showed a driving voltage of 3.8 V, an emission brightness of 586 cd/m$^2$, and an emission efficiency of 5.86 cd/A at a current density of 10 mA/cm$^2$.

Example 3

An organic light-emitting device was manufactured in the same manner as in Example 1, except for using Compound 31 of Formula 1 instead of using compound 1 of Formula 1.

The organic light-emitting device showed a driving voltage of 3.7 V, an emission brightness of 512 cd/m$^2$, and an emission efficiency of 5.12 cd/A at a current density of 10 mA/cm$^2$.

Example 4

An organic light-emitting device was manufactured in the same manner as in Example 1, except for using Compound 43 of Formula 1 instead of using Compound 1 of Formula 1.

The organic light-emitting device showed a driving voltage of 4.2 V, an emission brightness of 508 cd/m$^2$, and an emission efficiency of 5.08 cd/A at a current density of 10 mA/cm$^2$.

Comparative Example 1

An organic light-emitting device was manufactured in the same manner as in Example 1, except for using Compound 203 instead of Compound 94 of Formula 2.

The device showed a driving voltage of 4.4 V, an emission brightness of 485 cd/m$^2$, and an emission efficiency of 4.85 cd/A at a current density of 10 mA/cm$^2$.

Compound 203

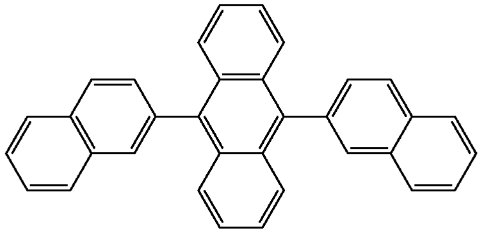

Comparative Example 2

An organic light-emitting device was manufactured in the same manner as in Example 1, except for using Compound 204 instead of Compound 1 of Formula 1.

The organic light-emitting device showed a driving voltage of 4.3 V, an emission brightness of 436 cd/m$^2$, and an emission efficiency of 4.36 cd/A at a current density of 10 mA/cm$^2$.

Compound 204

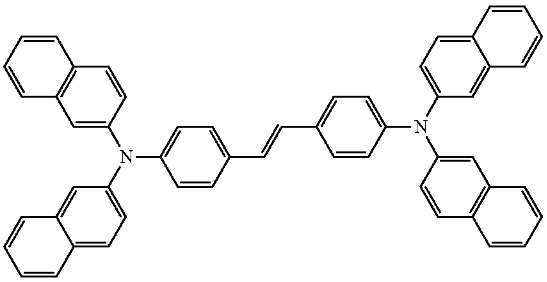

Results regarding properties and the lifespan of the organic light-emitting devices of the Examples are summarized in Table 1.

TABLE 1

| OLED | Driving voltage [V] | Brightness [cd/m2] | Efficiency [cd/A] |
|---|---|---|---|
| Example 1 | 3.7 | 576 | 5.56 |
| Example 2 | 3.8 | 586 | 5.86 |
| Example 3 | 3.7 | 512 | 5.12 |

TABLE 1-continued

| OLED | Driving voltage [V] | Brightness [cd/m2] | Efficiency [cd/A] |
|---|---|---|---|
| Example 4 | 4.2 | 508 | 5.08 |
| Comparative Example 1 | 4.4 | 485 | 4.85 |
| Comparative Example 2 | 4.3 | 436 | 4.36 |

As a result of using the compounds of Formula 1 and the compounds of Formula 2 as blue emission materials for the organic light-emitting devices, all of the organic light-emitting devices showed a decrease in driving voltage in comparison to Compounds 203 and 204, which are known in the field, an excellent I-V-L property (luminance as a function of applied voltage/current), and, specifically, an improved lifespan.

An organic light-emitting device, including a compound of Formula 1 and a compound of Formula 2, shows high color purity, high efficiency, and a long lifespan with respect to blue color.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims.

What is claimed is:

1. A compound represented by Formula 1:

<Formula 1>

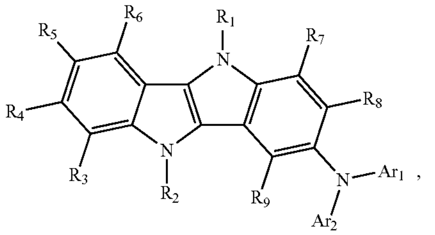

$R_1$ to $R_9$ in Formula 1 each being independently one of a hydrogen atom, a deuterium atom, a substituted or unsubstituted C5-C60 alkyl group, a substituted or unsubstituted C5-C60 aryl group, a substituted or unsubstituted C3-C60 heteroaryl group, an amine group substituted with a C5-C60 aryl group or a C3-C60 heteroaryl group, a substituted or unsubstituted C6-C60 condensed polycyclic group, a halogen group, a cyano group, a nitro group, a hydroxyl group and a carboxy group, and $Ar_1$ and $Ar_e$ each being independently one of a substituted or unsubstituted C5-C60 aryl group, a substituted or unsubstituted C3-C60 heteroaryl group and a substituted or unsubstituted C6-C60 condensed polycyclic group.

2. The compound of claim 1, $R_3$, $R_4$, $R_6$, $R_7$, $R_8$, and $R_9$ in Formula 1 being each independently one of a hydrogen atom and a deuterium atom.

3. The compound of claim 1, $R_1$ and $R_2$ in Formula 1 being each independently a compound of Formulae 2a to 2c:

2a

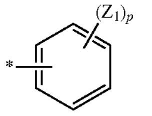

2b

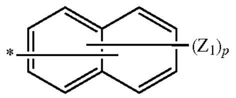

2c

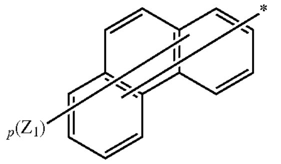

$Z_1$ in Formulae 2a to 2c being one of a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen group, a cyano group, a nitro group, a hydroxy group and a carboxy group, p is an integer of 1 to 9, and

* represents a bond.

4. The compound of claim 1, $R_5$ in Formula 1 being one of a substituted or unsubstituted C1-C20 alkyl group and a compound of Formulae 3a to 3d:

3a

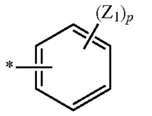

3b

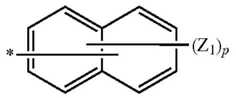

3c $*-N(R_{50})(R_{51})$

3d

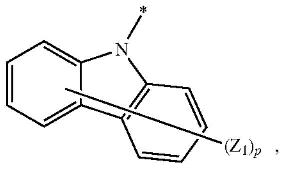

$Z_1$, $R_{50}$, and $R_{51}$ in Formulae 3a to 3d being each independently a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, an amino group substituted with a C5-C20 aryl group or a C3-C20 heteroaryl group, a halogen group, a cyano group, a nitro group, a hydroxyl group and a carboxy group;

p is an integer of 1 to 7; and

* represents a bond.

5. The compound of claim 1, $Ar_1$ and $Ar_e$ in Formula 1 being each independently a compound of one of Formulae 4a and 4b:

4a

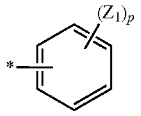

4b

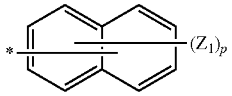 , $Z_1$ in Formulae 4a and 4b being one of a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, an amino group substituted with a C5-C20 aryl group or a C3-C20 heteroaryl group, a halogen group, a cyano group, a nitro group, a hydroxyl group and a carboxy group;

p is an integer of 1 to 7; and

* represents a bond.

6. An organic light-emitting device comprising a first electrode;

a second electrode; and an organic layer interposed between the first electrode and the second electrode, the organic layer comprising a compound represented by Formula 1 of claim 1.

7. The organic light-emitting device of claim 6, the organic layer further comprising a compound represented by Formula 2:

<Formula 2>

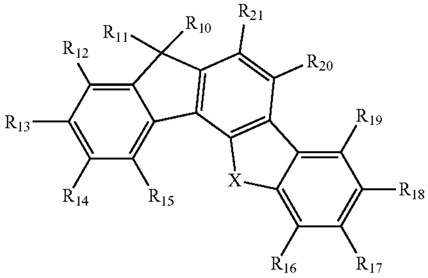 , $R_{10}$ to $R_{21}$ in Formula 2 being each independently one of a hydrogen atom, a deuterium atom, a substituted or unsubstituted C5-C60 alkyl group, a substituted or unsubstituted C5-C60 aryl group, a substituted or unsubstituted C3-C60 heteroaryl group, an amine group substituted with a C5-C60 aryl group or a C3-C60 heteroaryl group, a substituted or unsubstituted C6-C60 condensed polycyclic group, a halogen group, a cyano group, a nitro group, a hydroxyl group and a carboxy group, and X is a connecting group represented by one of —C($R_{100}$)($R_{101}$)—, —N($R_{102}$—, —S— and —O—, and $R_{100}$, $R_{101}$, and $R_{102}$ are each independently one of a substituted or unsubstituted C5-C30 aryl group, a substituted or unsubstituted C3-C30 heteroaryl group and a substituted or unsubstituted C6-C30 condensed polycyclic group.

8. The organic light-emitting device of claim 7, $R_{10}$ and $R_{11}$ in Formula 2 forming a 9,9'-spirobifluorene moiety [hence,

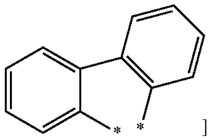 [SMILES: *c1ccccc1-c1ccccc1*] ]

by bonding to each other, or $R_{10}$ and $R_{11}$ are each independently a substituted or unsubstituted C1-C20 alkyl group; and

* represents a bond.

9. The organic light-emitting device of claim 7, $R_{13}$ in Formula 2 being one of Formulae 5a to 5c:

5a

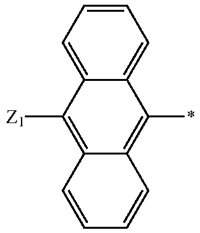

5b

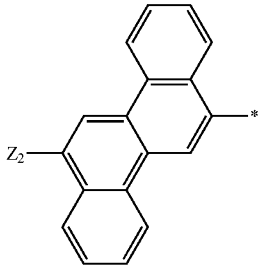

5c

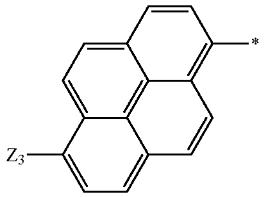 , $Z_1$, $Z_2$, and $Z_3$ in Formulae 5a to 5c being each independently one of a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, an amine group substituted with a C5-C20 aryl group or a C3-C20 heteroaryl group, a halogen group, a cyano group, a nitro group, a hydroxy group and a carboxy group; and

* represents a bond.

10. The organic light-emitting device of claim 1, compound 1 of Formula 1 being any one of following compounds:

-continued
1
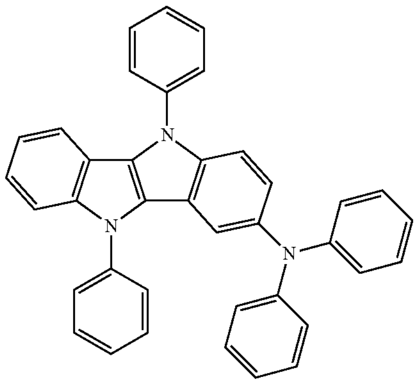
2
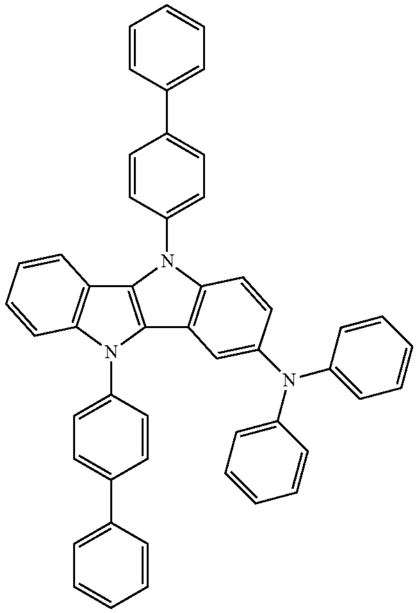
3
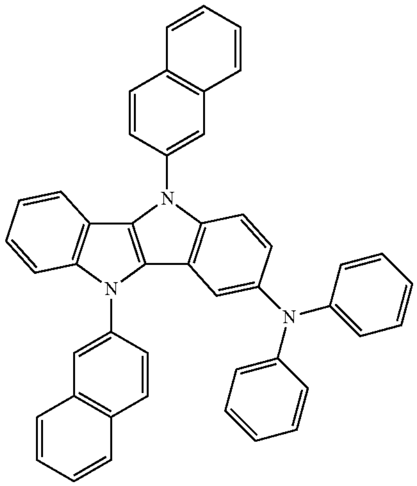
4
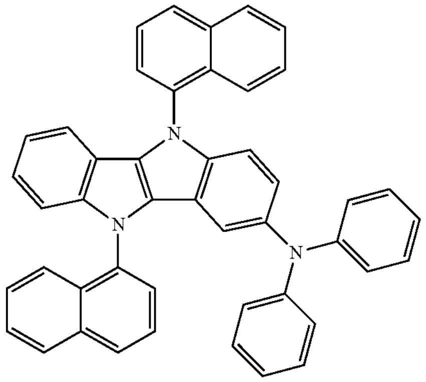
5
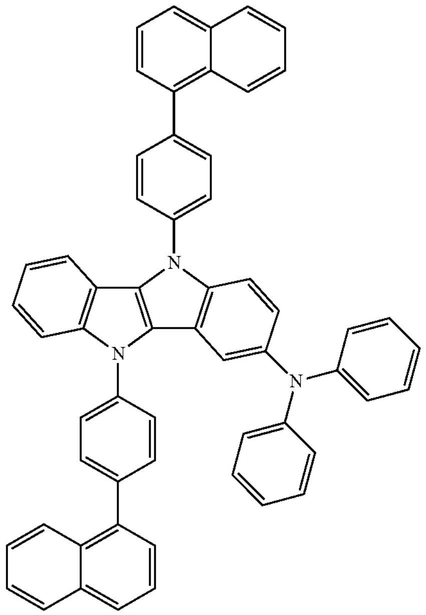
6
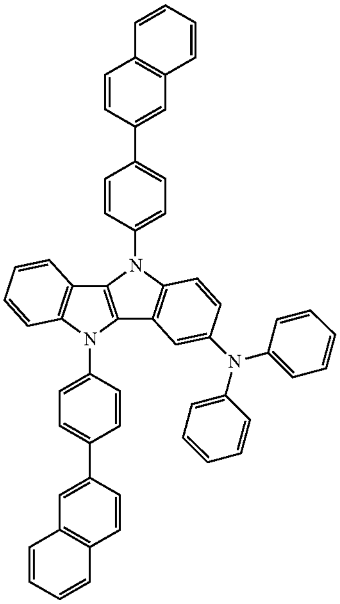

7
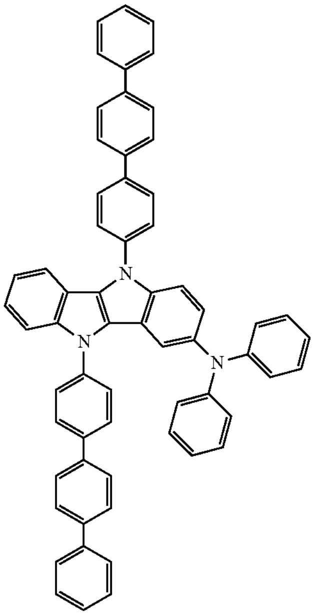
9
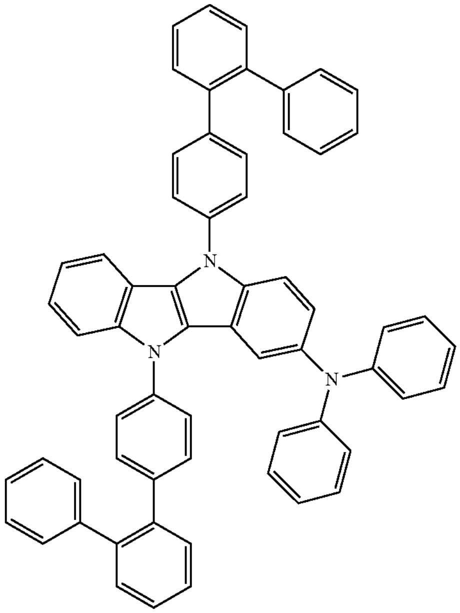
8
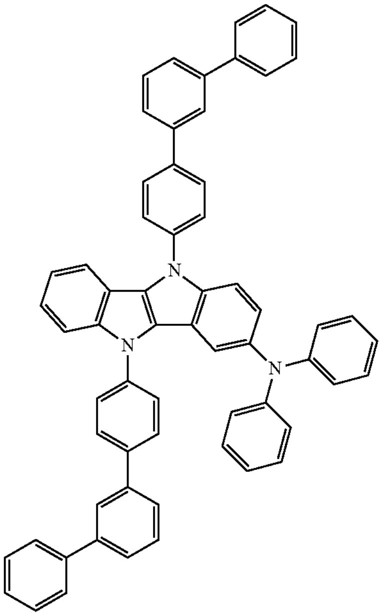
10
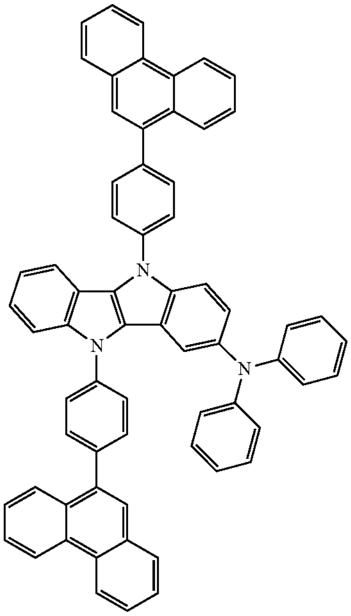

11
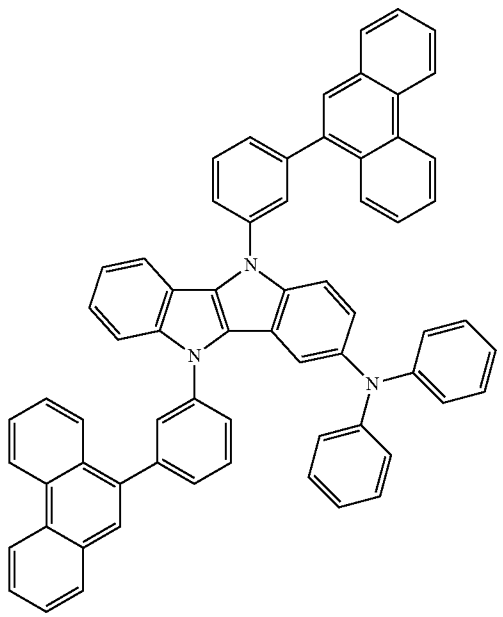
12
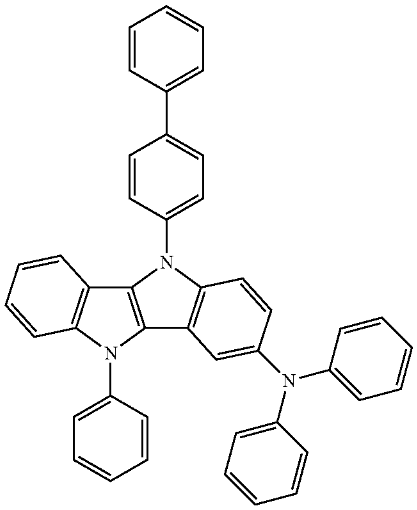
13
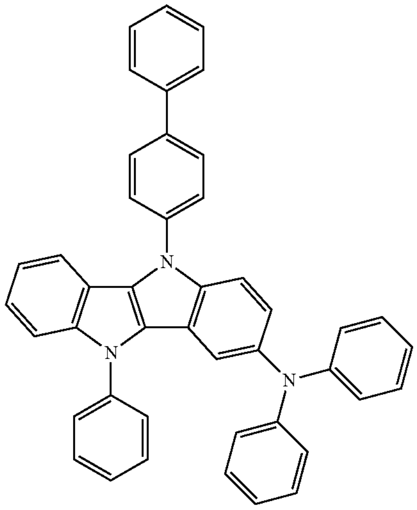
14
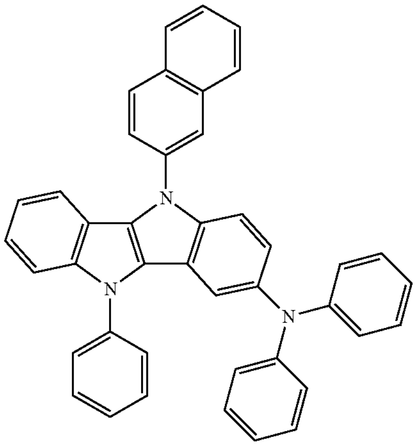
15
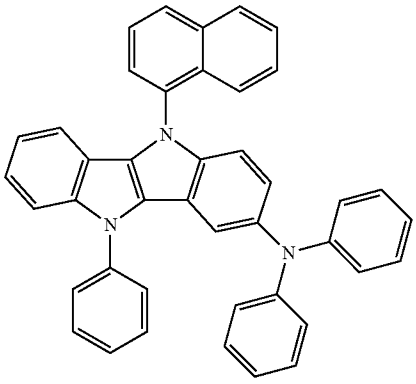
16
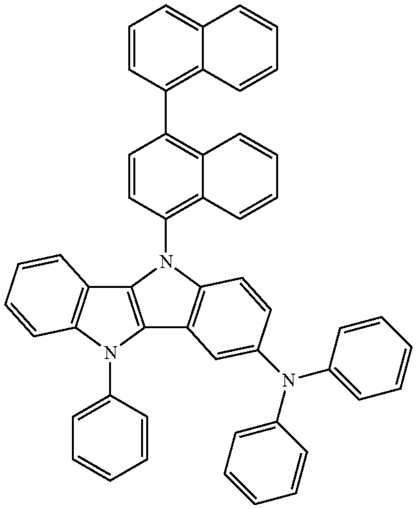

17
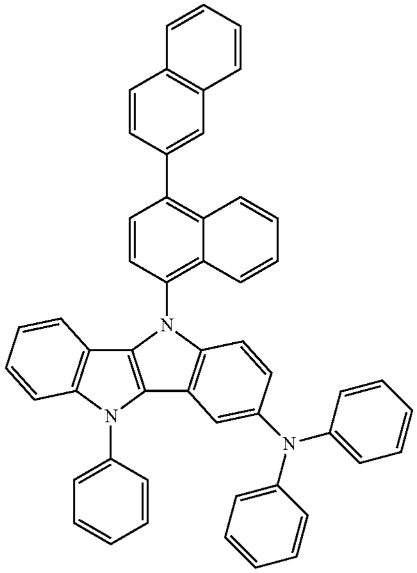
18
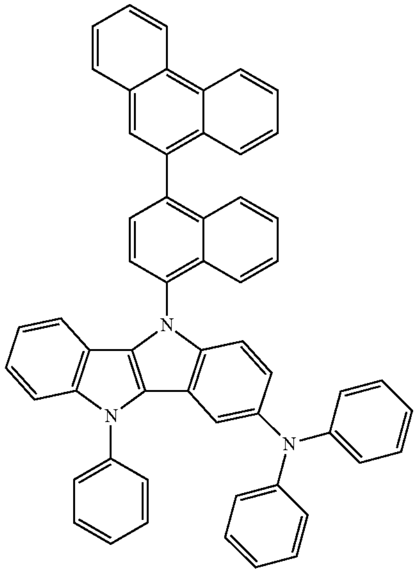
19
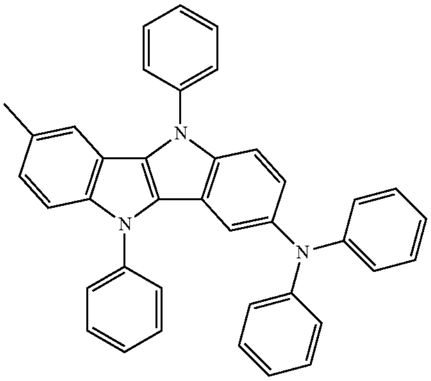
20
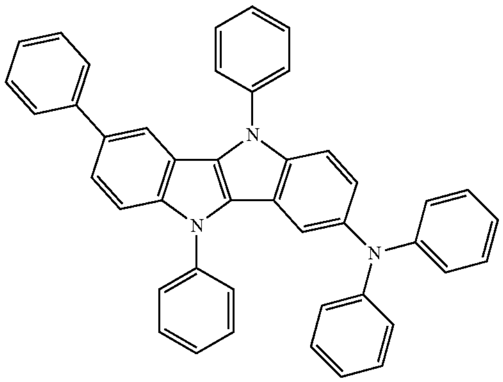
21
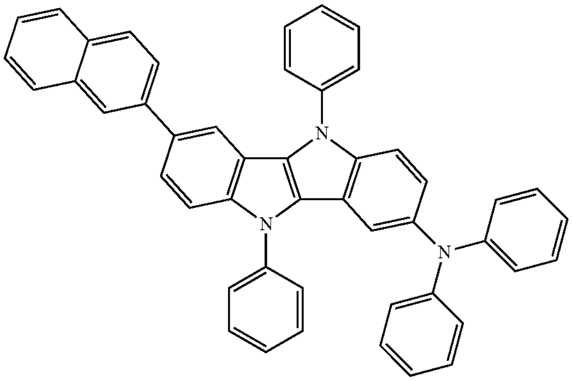
22
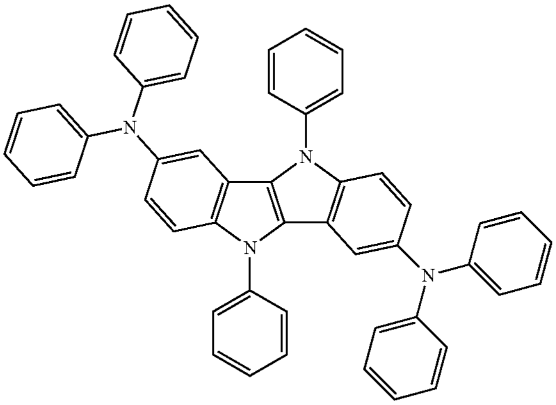

-continued
23
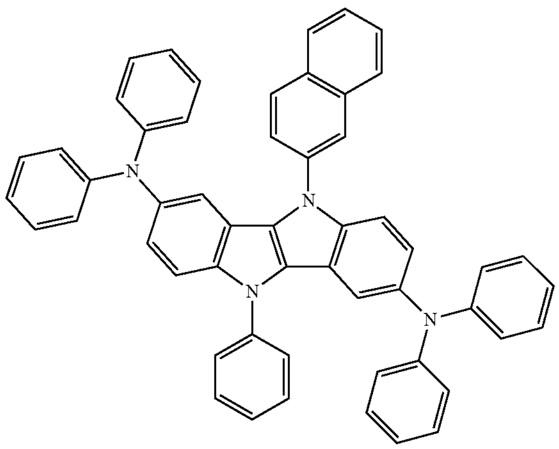
24
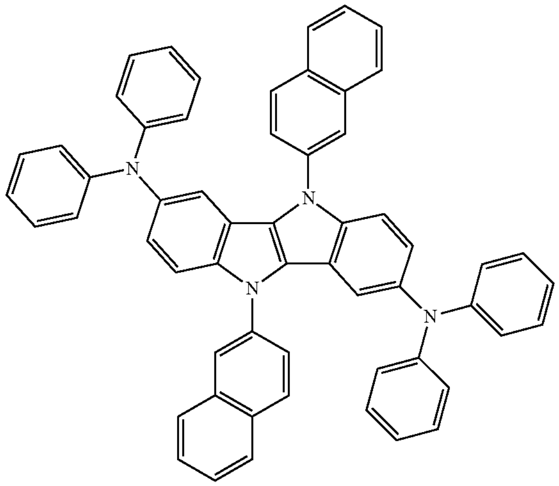
25
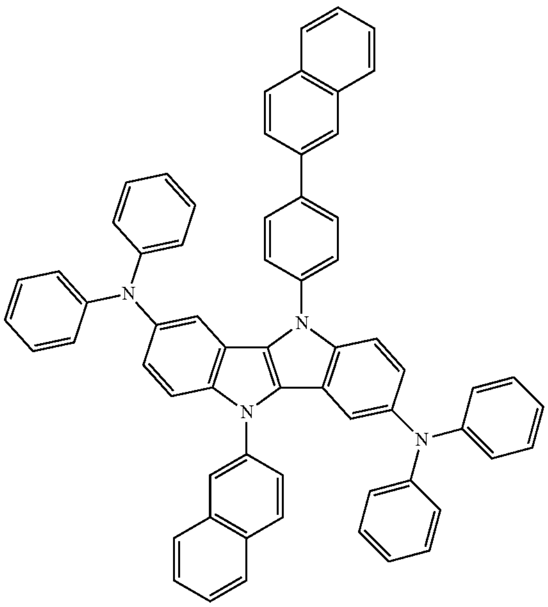
-continued
26
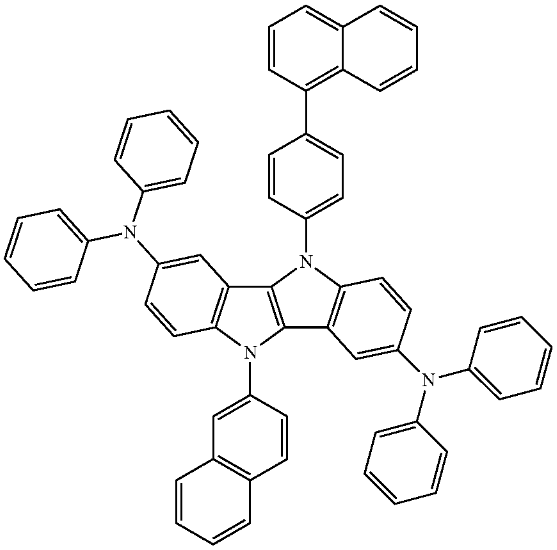
27
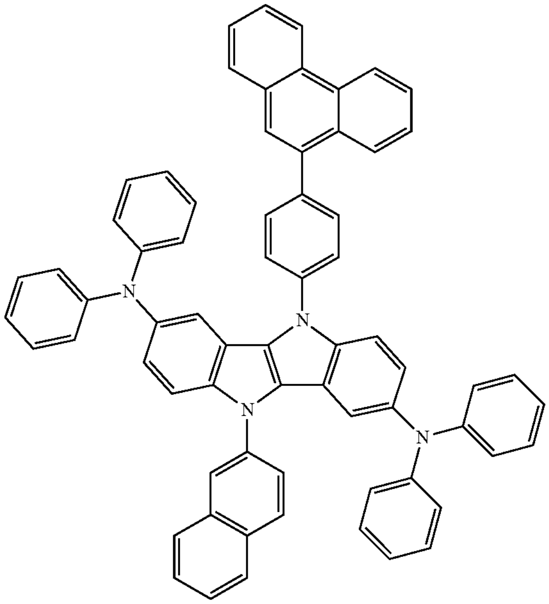

-continued
28
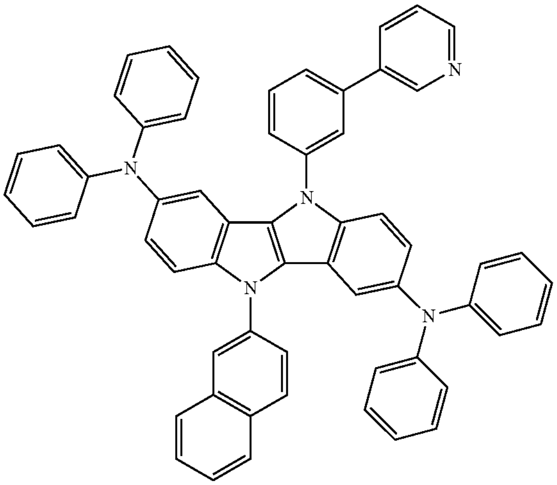
29
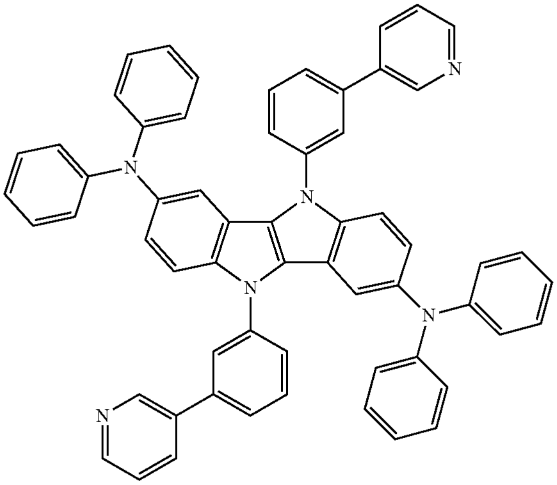
30
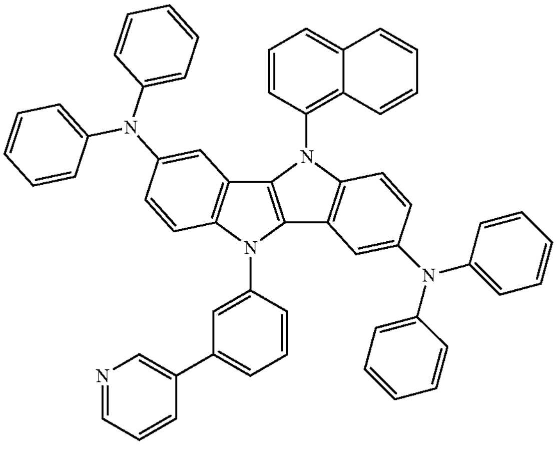
-continued
31
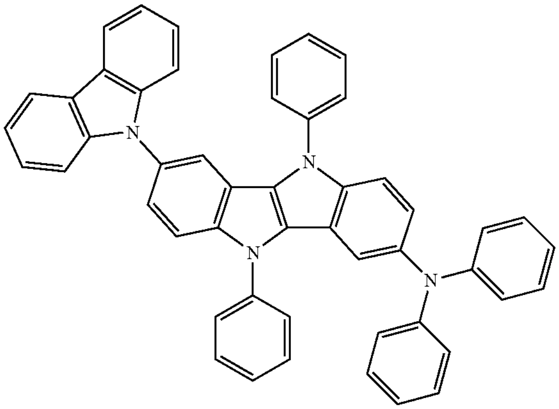
32
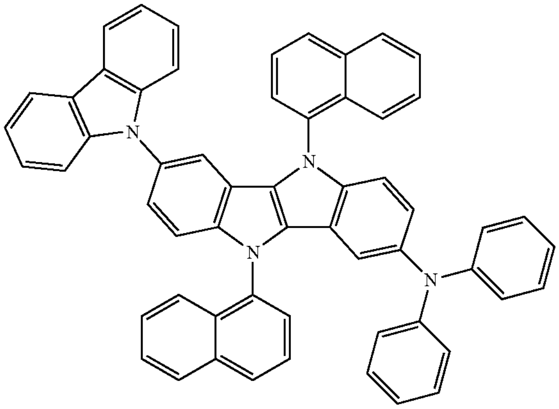
33
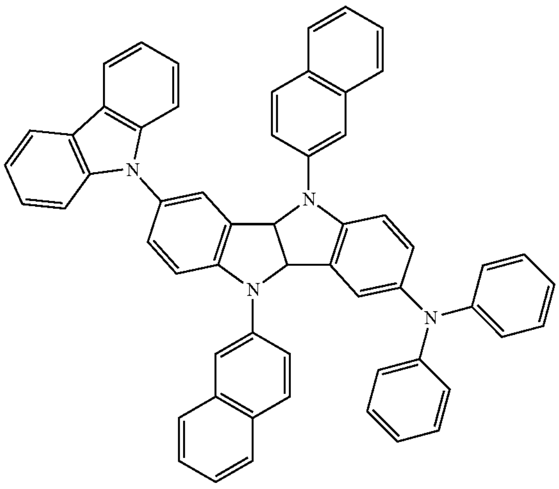

-continued
34
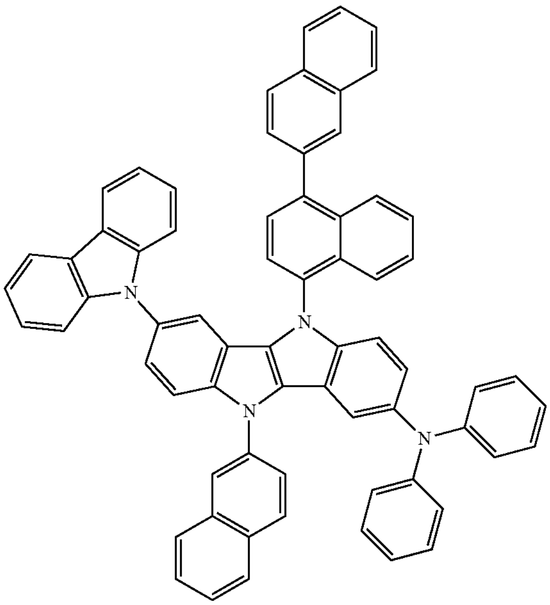
35
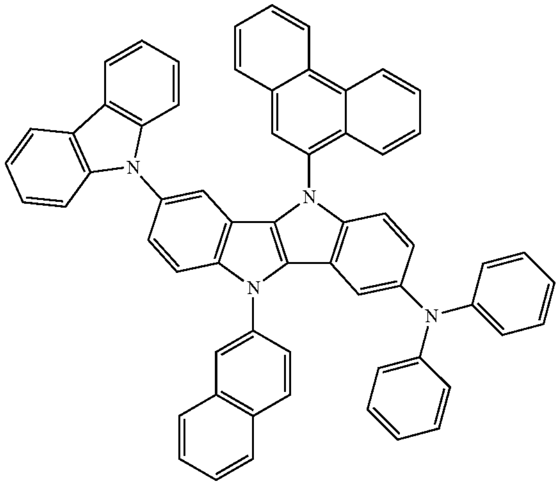
-continued
36
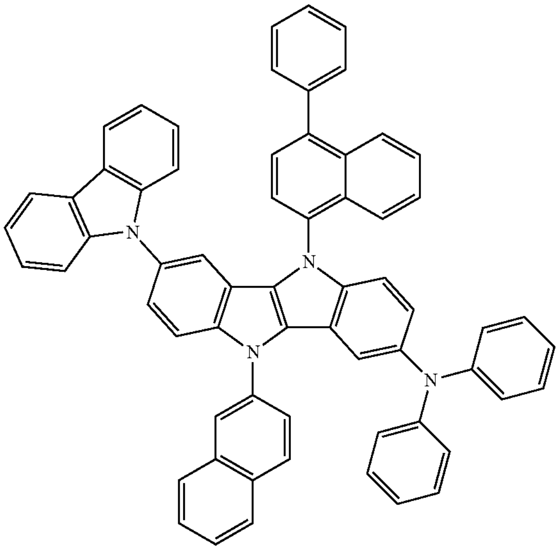
37
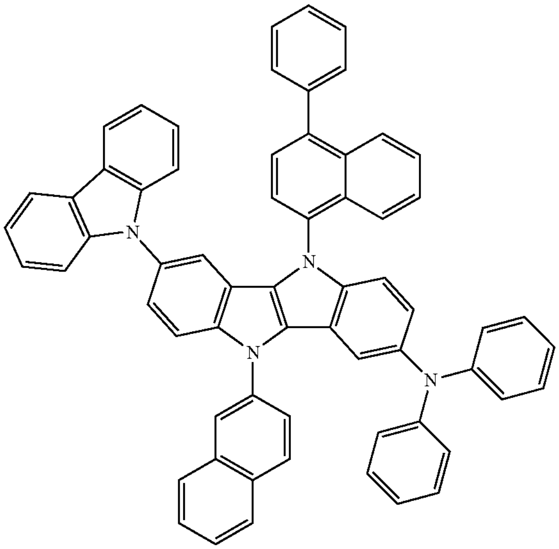

-continued
38
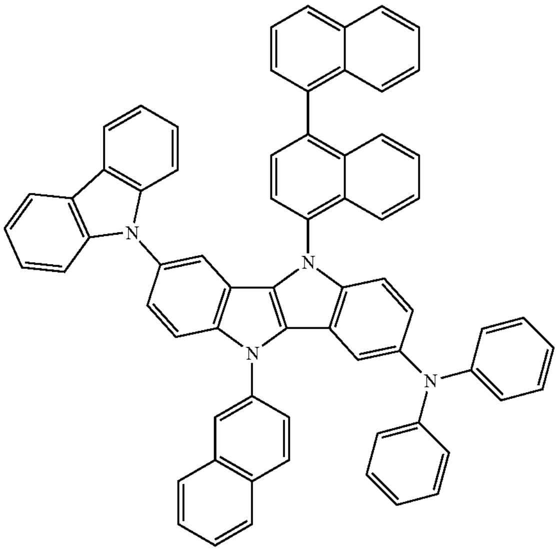
39
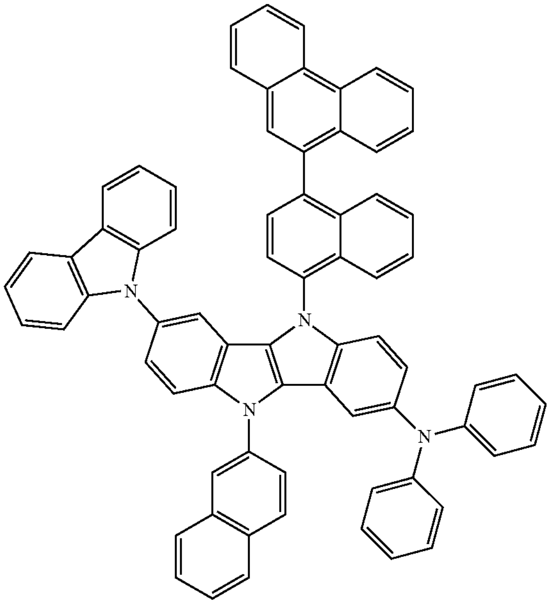
-continued
40
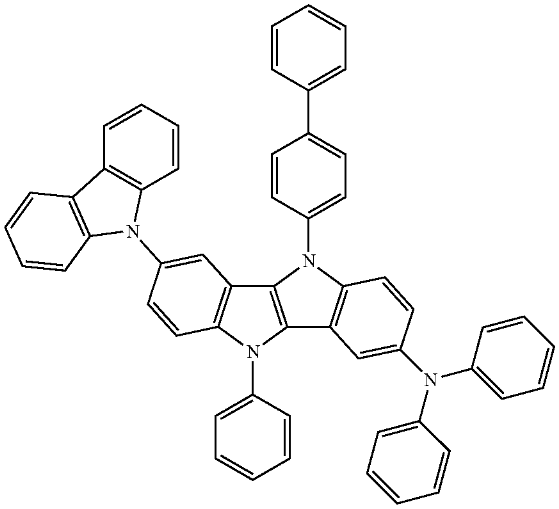
41
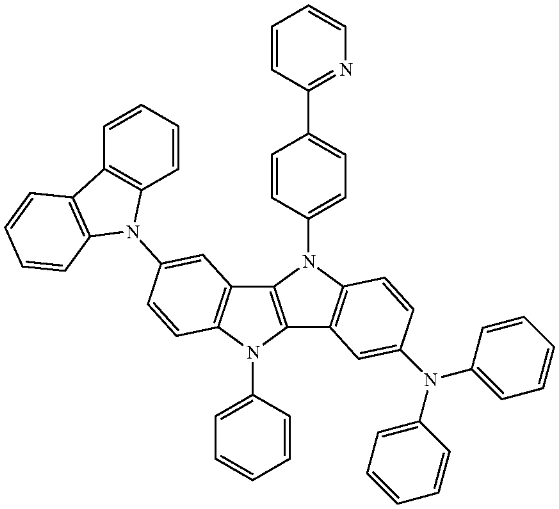
42
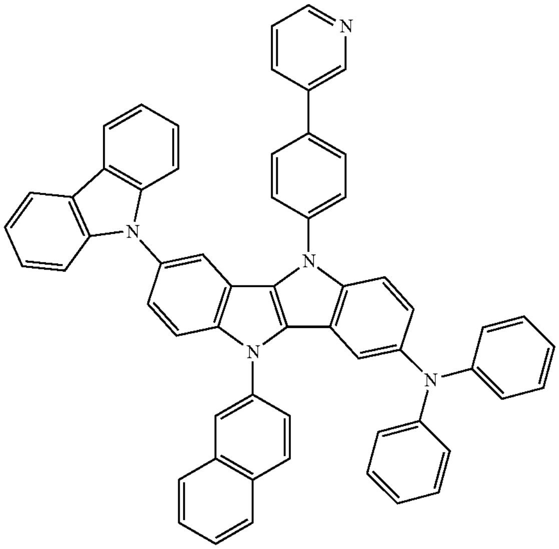

-continued
43
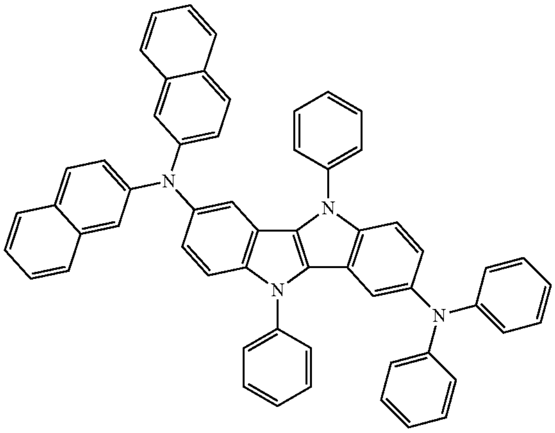
44
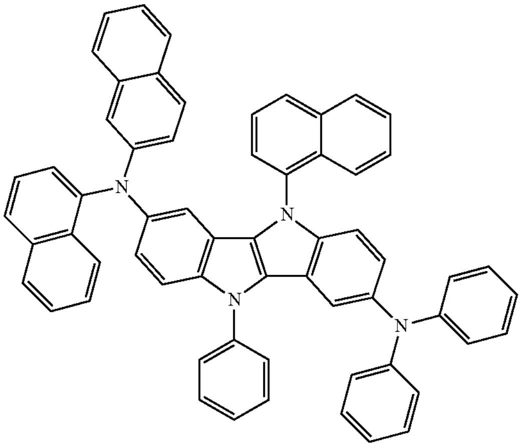
45
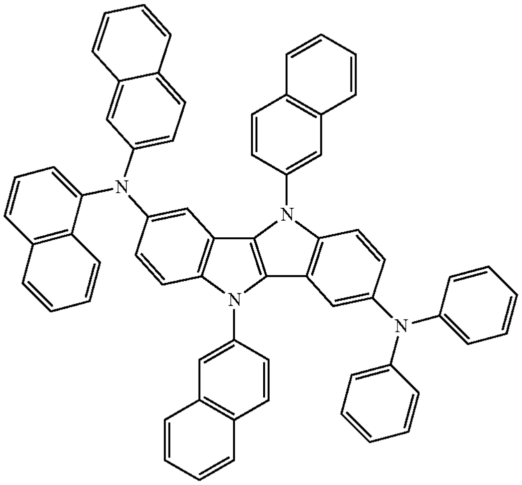
-continued
46
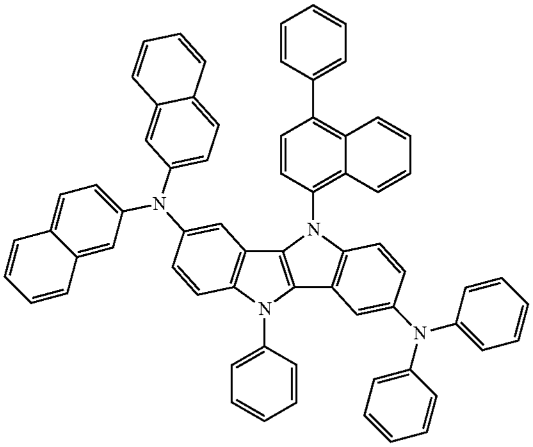
47
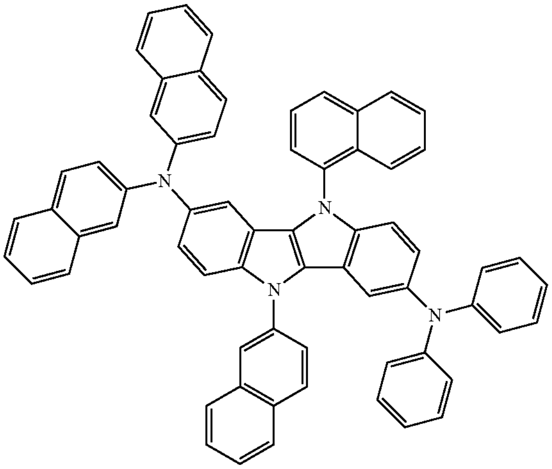
48
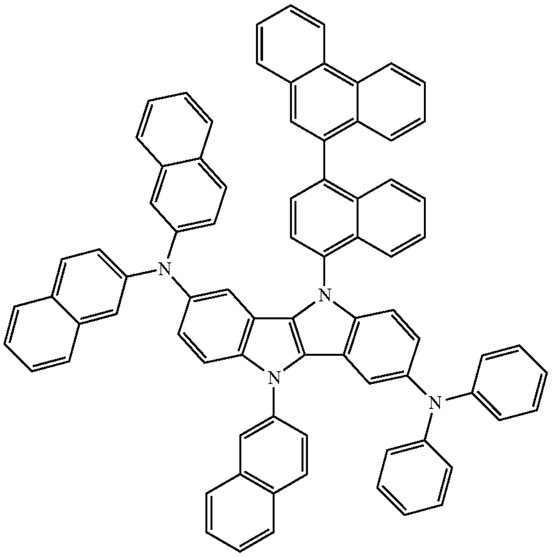

-continued
49
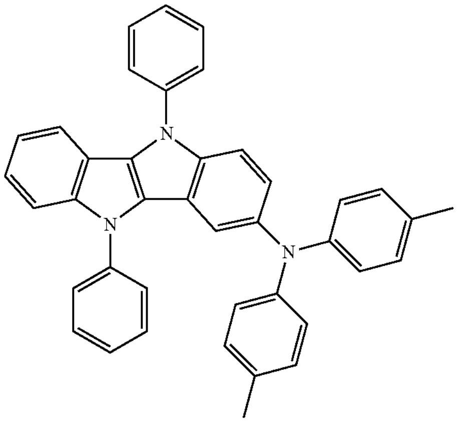
50
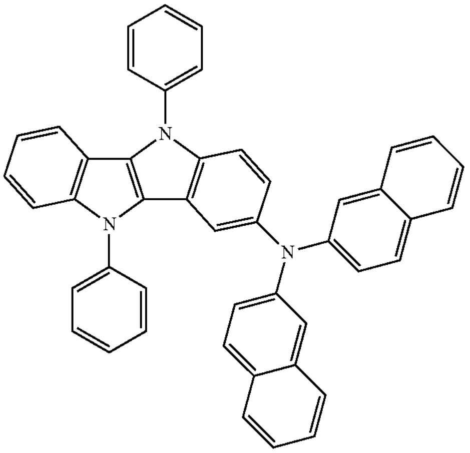
51
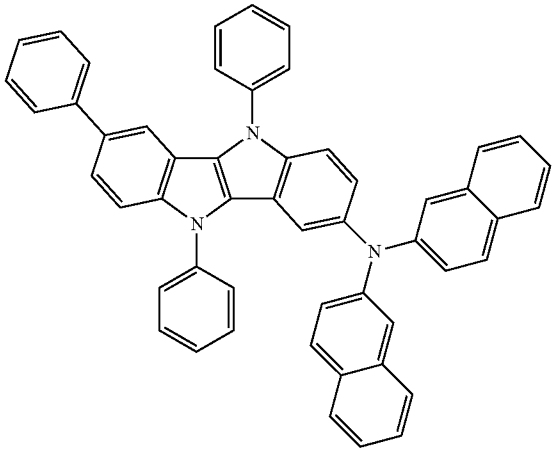
-continued
52
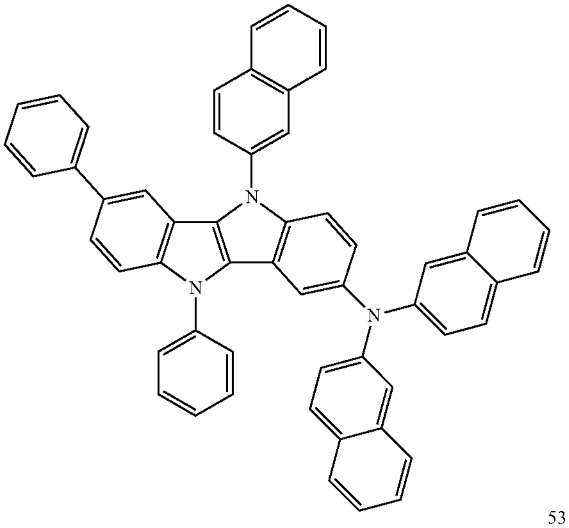
53
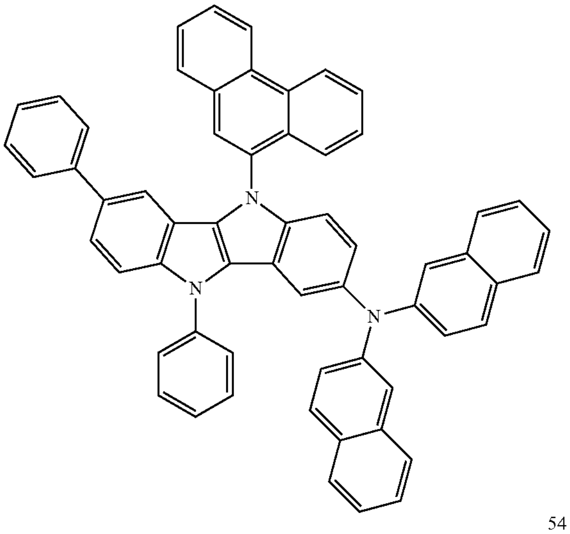
54
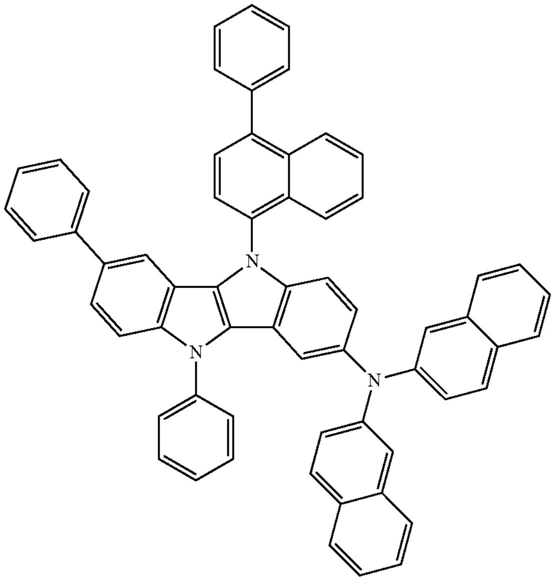
.

11. The organic light-emitting device of claim 7, the compound of Formula 2 being any one of following compounds:
55
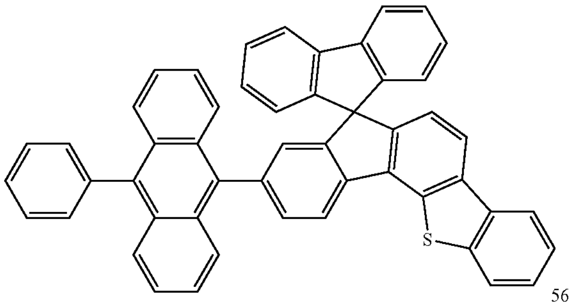
56
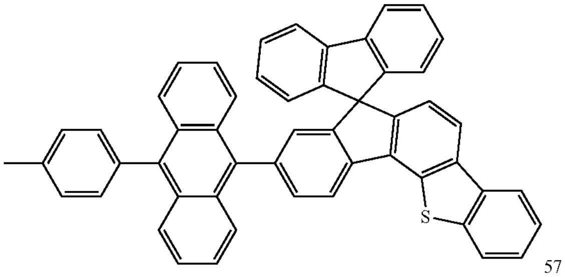
57
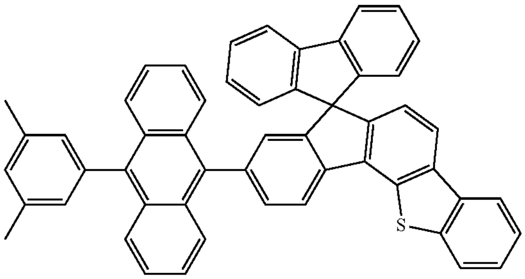
58
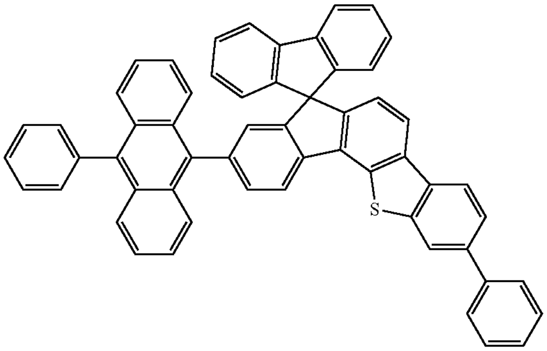
59
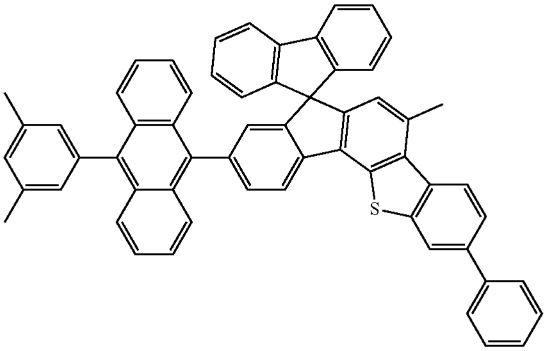
-continued
60
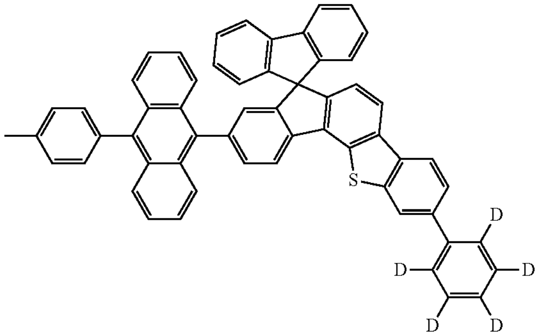
61
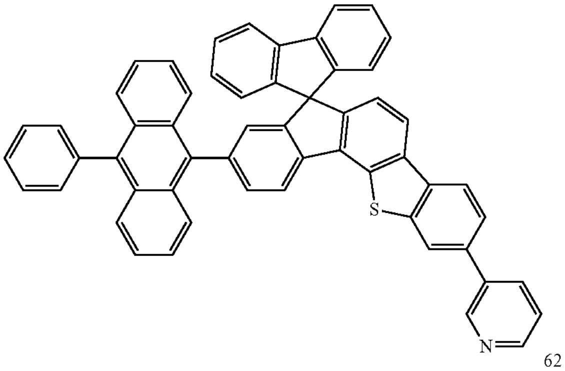
62
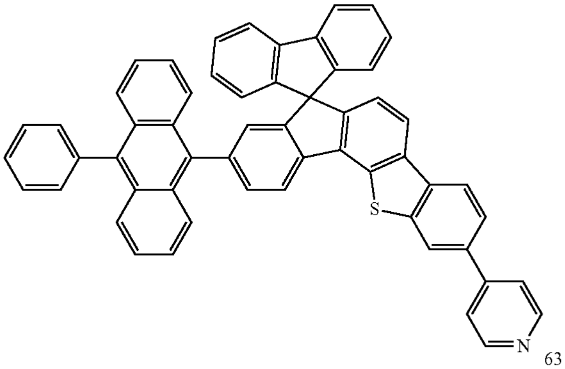
63
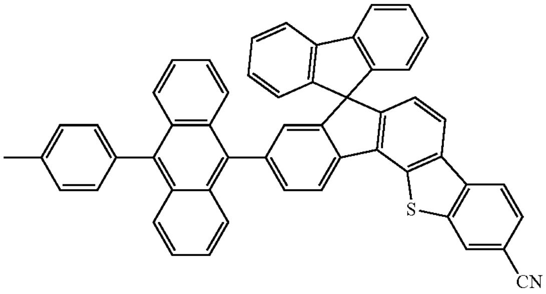
64
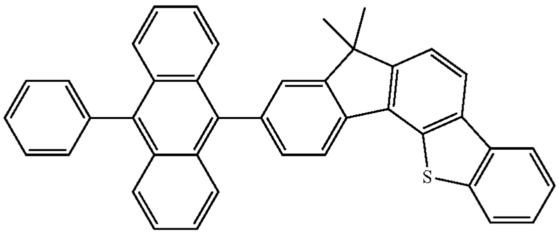

-continued
65
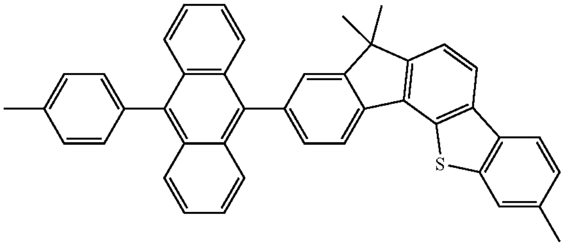
66
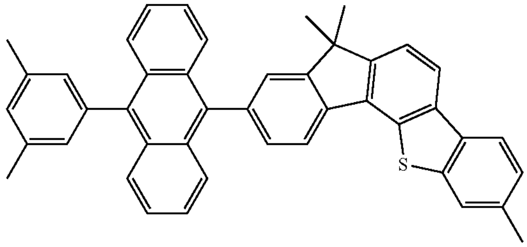
67
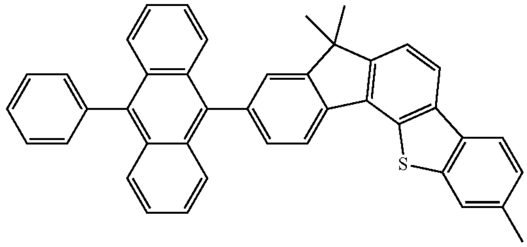
68
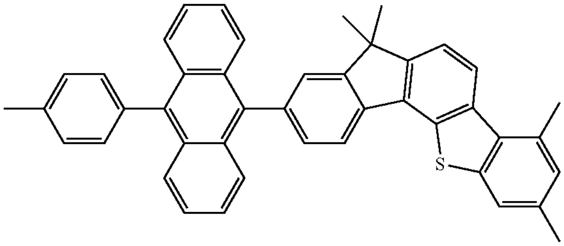
69
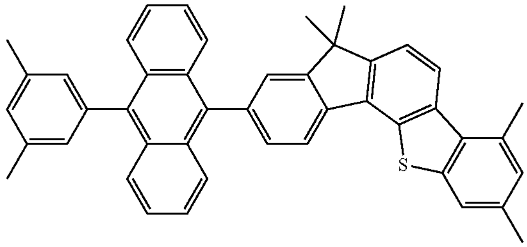
70
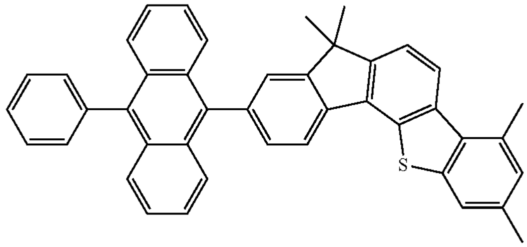
-continued
71
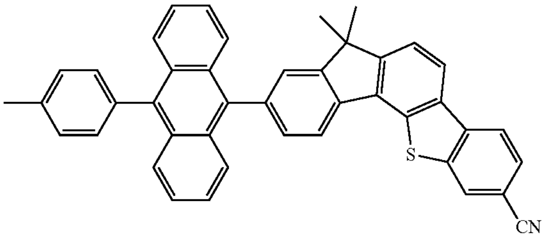
72
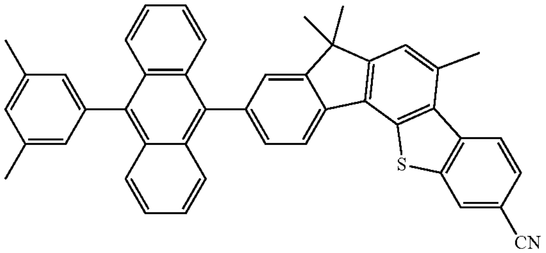
73
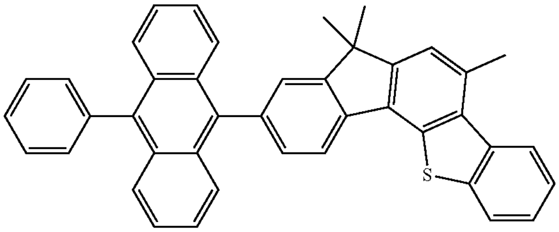
74
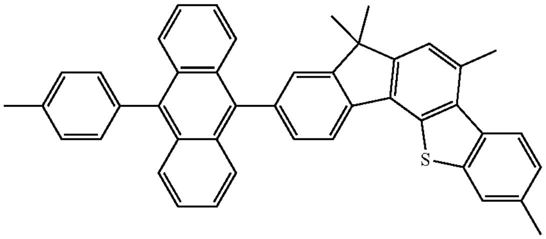
75
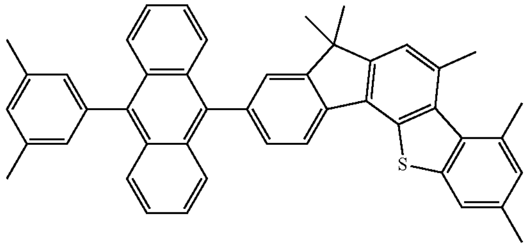
76
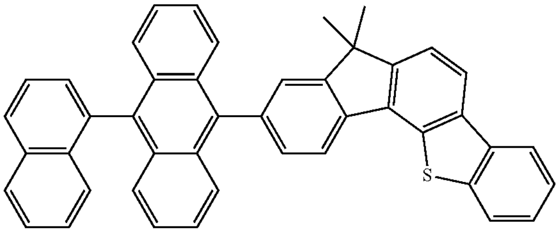

-continued
77
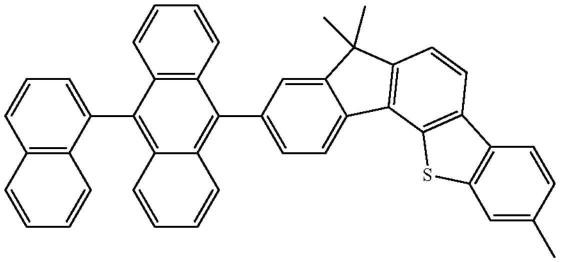
78
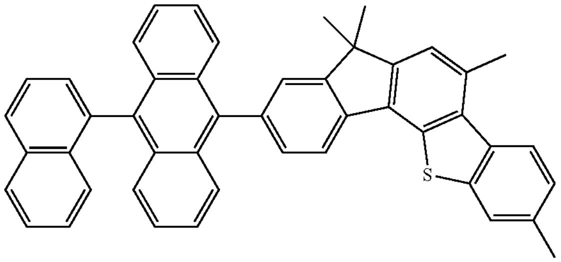
79
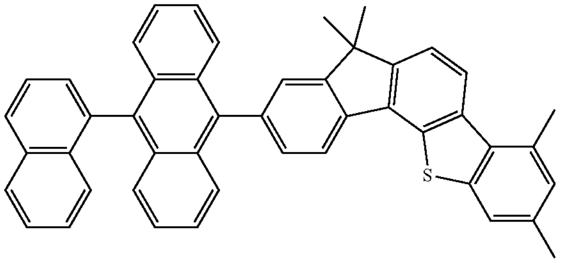
80
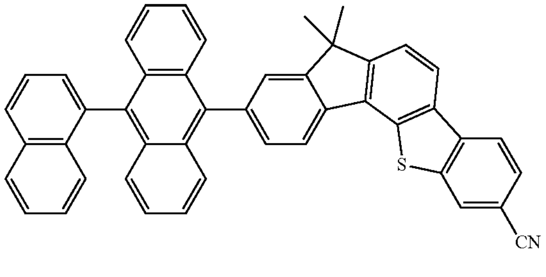
81
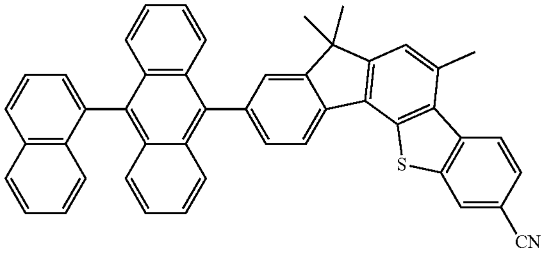
-continued
82
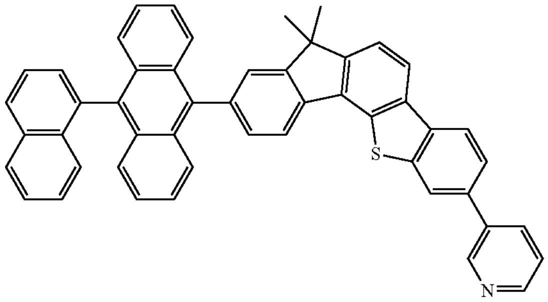
83
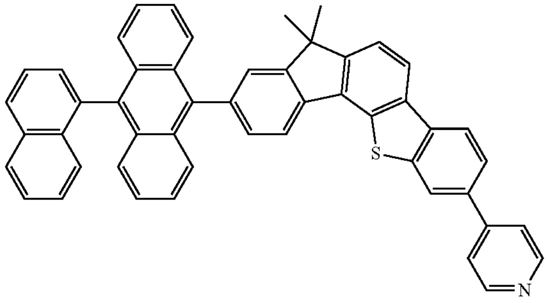
84
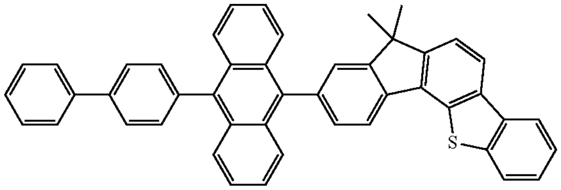
85
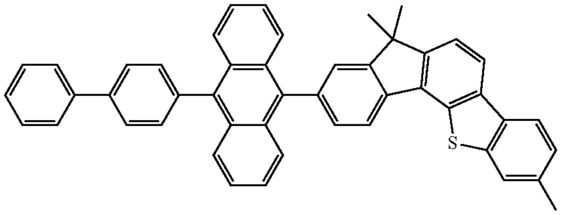
86
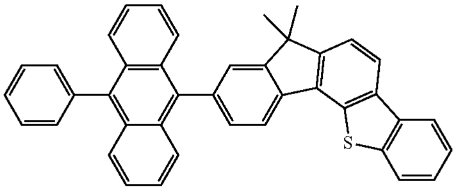
87
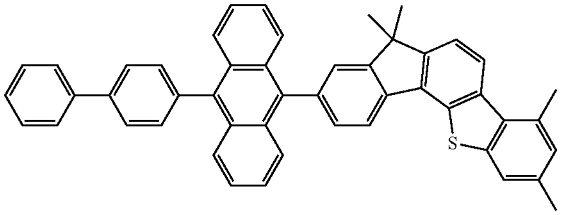

-continued
88
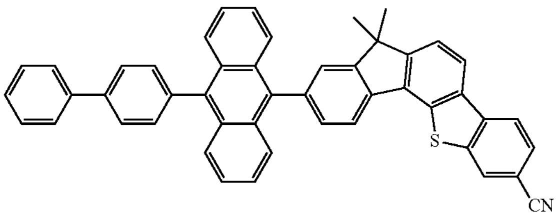
89
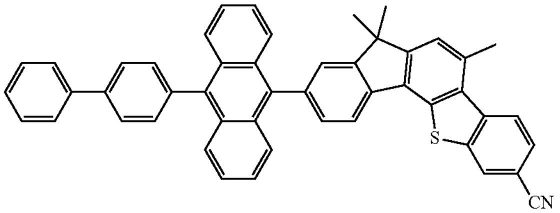
90
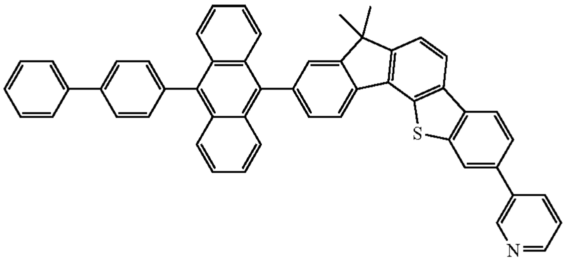
91
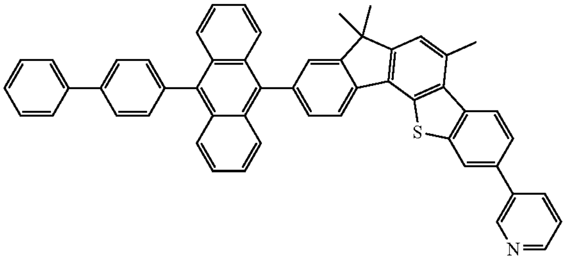
92
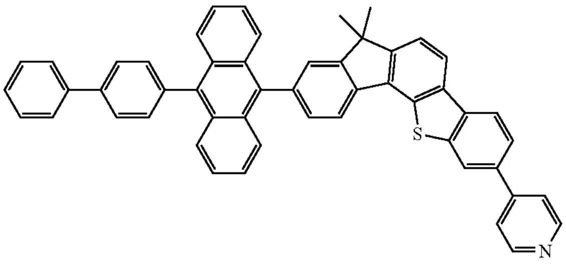
93
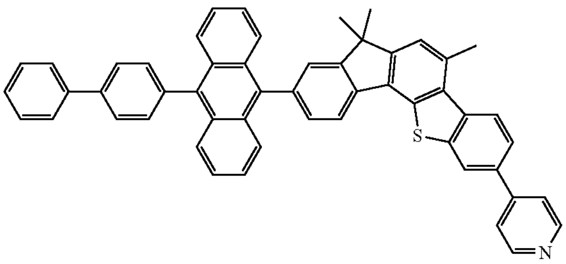
-continued
94
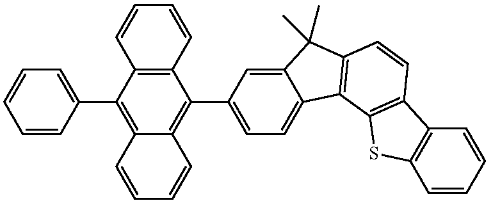
95
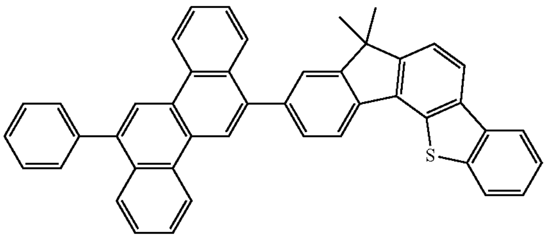
96
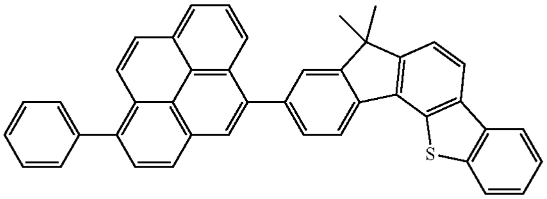
97
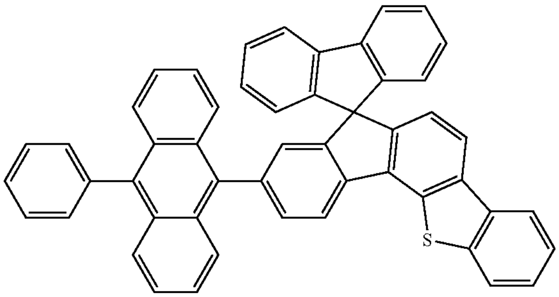
98
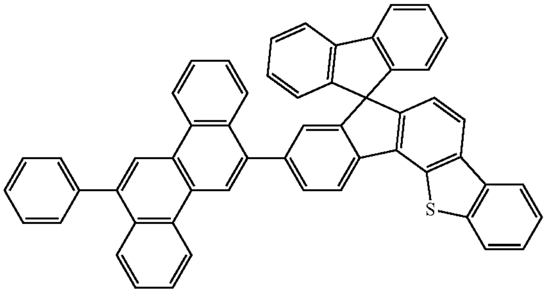

-continued

99

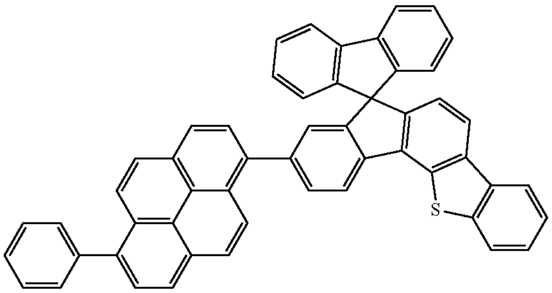

100

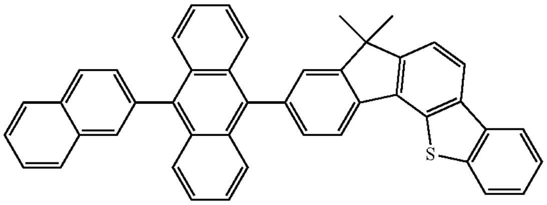

101

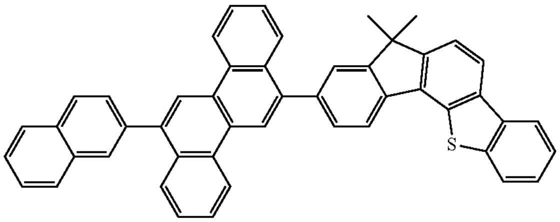

102

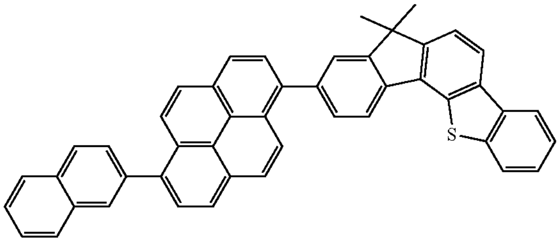

103

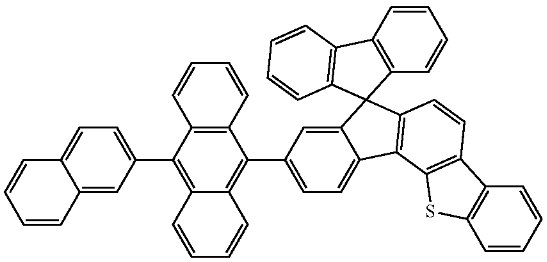

-continued

104

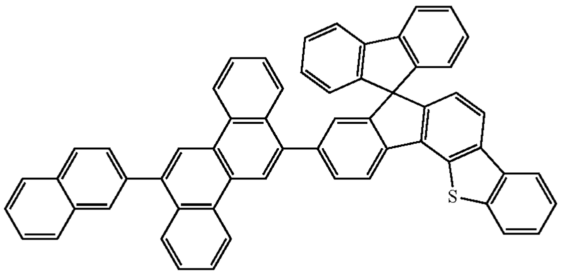

105

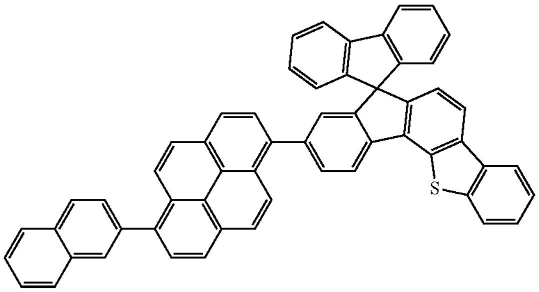

.

12. The organic light-emitting device of claim 6, the organic layer being an emission layer.

13. The organic light-emitting device of claim 6, the organic layer comprising an emission layer, an electron injection layer, an electron transport layer, a functional layer having both electron injection and electron transport capabilities, a hole injection layer, a hole transport layer, or a functional layer having both hole injection and hole transport capabilities, and the emission layer comprising one of an anthracene-based compound, an arylamine-based compound and a styryl-based compound.

14. The organic light-emitting device of claim 6, the organic layer comprising an emission layer, an electron injection layer, an electron transport layer, a functional layer having both electron injection and electron transport capabilities, a hole injection layer, a hole transport layer, or a functional layer having both hole injection and hole transport capabilities, and at least one of a red color layer, a green color layer, a blue color layer, and a white color layer of the emission layer comprising a phosphorescent compound.

15. The organic light-emitting device of claim 14, one of the hole injection layer, the hole transport layer and the functional layer having both hole injection and hole transport capabilities comprising a charge-generating material.

16. The organic light-emitting device of claim 15, the charge-generating material comprising a p-dopant.

17. The organic light-emitting device of claim 16, the p-dopant being one of a quinone derivative, a metal oxide and a cyano group-containing compound.

18. The organic light-emitting device of claim 6, the organic layer comprising an electron transport layer, the electron transport layer comprising a metal complex.

19. The organic light-emitting device of claim 6, the organic layer being formed through a wet method by using the compound comprised in the organic layer.

20. A flat display device comprising the organic light-emitting device of claim 6, a first electrode of the organic light-emitting device being electrically connected to one of a source electrode and a drain electrode of a thin film transistor.

* * * * *